(12) United States Patent
Ellinger et al.

(10) Patent No.: US 11,732,020 B2
(45) Date of Patent: Aug. 22, 2023

(54) T CELL RECEPTORS AND USES THEREOF

(71) Applicant: MEDIGENE IMMUNOTHERAPIES GMBH, Planegg-Martinsried (DE)

(72) Inventors: Christian Ellinger, Munich (DE); Carina Wehner, Munich (DE); Manon Weis, Sankt Wolfgang (DE); Susanne Wilde, Germering (DE); Dolores Schendel, Munich (DE)

(73) Assignee: MEDIGENE IMMUNOTHERAPIES GMBH, Planegg-Martinsried (DE)

( * ) Notice: Subject to any disclaimer, the term of this patent is extended or adjusted under 35 U.S.C. 154(b) by 472 days.

(21) Appl. No.: 16/309,902

(22) PCT Filed: Jun. 16, 2017

(86) PCT No.: PCT/EP2017/064729
§ 371 (c)(1),
(2) Date: Dec. 13, 2018

(87) PCT Pub. No.: WO2017/216324
PCT Pub. Date: Dec. 21, 2017

(65) Prior Publication Data
US 2019/0169261 A1 Jun. 6, 2019

(30) Foreign Application Priority Data

Jun. 17, 2016 (LU) .......................................... 93112
Mar. 10, 2017 (EP) .................................... 17160260

(51) Int. Cl.
| | | |
|---|---|---|
| C07K 14/725 | (2006.01) | |
| C07K 14/735 | (2006.01) | |
| C07K 14/74 | (2006.01) | |
| C07K 16/30 | (2006.01) | |
| C07K 14/47 | (2006.01) | |
| A61K 39/00 | (2006.01) | |
| A61P 35/00 | (2006.01) | |
| A61K 35/17 | (2015.01) | |

(52) U.S. Cl.
CPC .......... *C07K 14/7051* (2013.01); *A61K 35/17* (2013.01); *A61K 39/00119* (2018.08); *A61P 35/00* (2018.01); *C07K 14/4748* (2013.01); *C07K 14/70539* (2013.01); *C07K 16/3053* (2013.01); *A61K 2039/5154* (2013.01); *C07K 2317/34* (2013.01); *C07K 2317/73* (2013.01)

(58) Field of Classification Search
None
See application file for complete search history.

(56) References Cited

FOREIGN PATENT DOCUMENTS

| EP | 2 746 393 A1 | 6/2014 |
|---|---|---|
| WO | 2001/52614 A2 | 7/2001 |
| WO | 2009/026116 A2 | 2/2009 |
| WO | 2013/002086 A1 | 1/2013 |

OTHER PUBLICATIONS

Knapp et al (PLOS Computational Biology PCBI.1007338: pp. 1/17-17/17, 2019) (Year: 2019).*
Qiu et al (Bioconjugate Chem. 2020, 31: 2767-2778) (Year: 2020).*
HLA Nomenclature 2015 (Year: 2015).*
Singh et al (J. Immunol. 2017, 199: 2203-2213) (Year: 2017).*
Ramakrishna et al. (Expert Opinion on Biological Therapy, 2020, 20(5): 503- 516) (Year: 2020).*
Zhang et al (Nature Medicine, 2022, 28: 1421-1431) (Year: 2022).*
Kim et al., A novel multiparametric flow cytometry-based cytotoxicity assay simultaneously immunophenotypes effector cells: Comparisons to a 4 h 51Cr-release assay. J Immunol Methods. Aug. 31, 2007; 325(1-2): 51-66.
Vigano et al., Functional Avidity: A Measure to Predict the Efficacy of Effector T Cells? Clin Dev Immunol. 2012;2012:153863 (14 pages).
Van Loenen et al., "Milti-cistronic vector encoding optimized safety switch for adoptive therapy with T-cell receptor-modified T cells", Gene Therapy, Nature Publishing Group, GB, vol. 20, No. 8, Aug. 1, 2013 (Aug. 1, 2013), pp. 861-867.
Amir et al., "PRAME-specific Allo-HLA-restricted T cells with potent antitumor reactivity useful for therapeutic T-cell receptor gene transfer", Clinical Cancer Research, The American Association for Cancer Research, US, vol. 17, No. 17, Sep. 1, 2011 (Sep. 1, 2011), pp. 5615-5625.
Kessler et al., "Efficient identification of novel HLA-A(*)0201-presented cytotoxic T lymphocyte epitopes in the widely expressed tumor antigen PRAME by proteasome-mediated digestion analysis", The Journal of Experimental Medicine, Rockefeller University Press, US, vol. 193, No. I, Jan. 1, 2001 (Jan. 1, 2001), pp. 73-88.
Mosquera et al., "In vitro and in vivo characterization of a novel antibody-like single-chain TCR human IgGI fusion protein", The Journal of Immunology, The American Association of Immunologists, US, vol. 174, No. 7, Apr. 1, 2005 (Apr. 1, 2005), pp. 4381-4388.

(Continued)

*Primary Examiner* — Michael Szperka
*Assistant Examiner* — Marianne DiBrino
(74) *Attorney, Agent, or Firm* — Acuity Law Group, PC; Michael A. Whittaker

(57) ABSTRACT

The present invention relates to the field of biotechnology. Specifically, the invention provides antigen-specific T-cell receptors (TCRs). Further, the invention encompasses polynucleotides encoding the same and vectors comprising said polynucleotides. Host cells comprising the molecules of the invention are also provided. Moreover, the invention provides means and methods for diagnostics and therapy, in particular of cancer.

13 Claims, 15 Drawing Sheets

Specification includes a Sequence Listing.

(56) References Cited

OTHER PUBLICATIONS

Emmet McCormack et al., "Bi-specific TCR-anti CD3 redirected T-cell targeting of NY-ES0-1- and LAGE-1-positive tumors", Cancer Immunology, Immunotherapy, vol. 62, No. 4, Dec. 22, 2012 (Dec. 22, 2012), pp. 773-785.
International Search Report issued in PCT/EP2017/064729 dated Sep. 14, 2017 (3 pages).
Altschul et al., Basic Local Alignment Search Tool. J Mol Biol. Oct. 5, 1990;215(3):403-410.
Altschul et al., Gapped BLAST and PSI-BLAST: a new generation of protein database search programs. Nucleic Acids Res. Sep. 1, 1997;25(17):3389-3402.
Chen et al., Fusion Protein Linkers: Property, Design and Functionality. Adv Drug Deliv Rev. Oct. 2013;65(10):1357-1369.
Gargett and Brown, The inducible caspase-9 suicide gene system as a "safety switch" to limit on-target, off-tumor toxicities of chimeric antigen receptor T cells. Front Pharmacol. Oct. 28, 2014,5:235.
Gertner-Dardenne et al., Human Vγ9Vδ2 T Cells Specifically Recognize and Kill Acute Myeloid Leukemic Blasts. J Immunol May 1, 2012;188(9):4701-4708 (incl suppl material).
Kieback et al., A safeguard eliminates T cell receptor gene-modified autoreactive T cells after adoptive transfer. Proc Natl Acad Sci USA Jan. 15, 2008;105(2):623-628.
Kim and Kim, A Guide to Genome Engineering With Programmable Nucleases. Nat Rev Genet. May 2014;15 (5):321-334.
Kuball et al., Facilitating matched pairing and expression of TCR chains introduced into human T cells. Blood. Mar. 15, 2007;109(6):2331-2338.
Leisegang et al., T-cell Receptor Gene-Modified T Cells With Shared Renal Cell Carcinoma Specificity for Adoptive T-cell Therapy Clin Cancer Res Apr. 15, 2010;16(8):2333-2343.
Schmitt et al., T Cell Receptor Gene Therapy for Cancer. Hum Gene Ther. Nov. 2009;20(11):1240-1248.
Smith and Waterman, Identification of Common Molecular Subsequences. J Mol Biol. Mar. 25, 1981;147(1):195-197.
Sommermeyer and Uckert, Minimal Amino Acid Exchange in Human TCR Constant Regions Fosters Improved Function of TCR Gene-Modified T Cells. J Immunol. Jun. 1, 2010;184(11):6223-6231 (incl suppl material).
Walseng et al., Soluble T-cell Receptors Produced in Human Cells for Targeted Delivery. PLoS One. Apr. 13, 2015;10(4):e0119559.
Wilde et al., Human Antitumor CD8+ T Cells Producing Th1 Polycytokines Show Superior Antigen Sensitivity and Tumor Recognition J Immunol. Jul. 15, 2012;189(2):598-605 (incl suppl material).
Xue et al., Exploiting T cell receptor genes for cancer immunotherapy. Clin Exp Immunol. Feb. 2005; 139(2): 167-172.

* cited by examiner

- HLA-2 is an endogenous gene

Figure 8
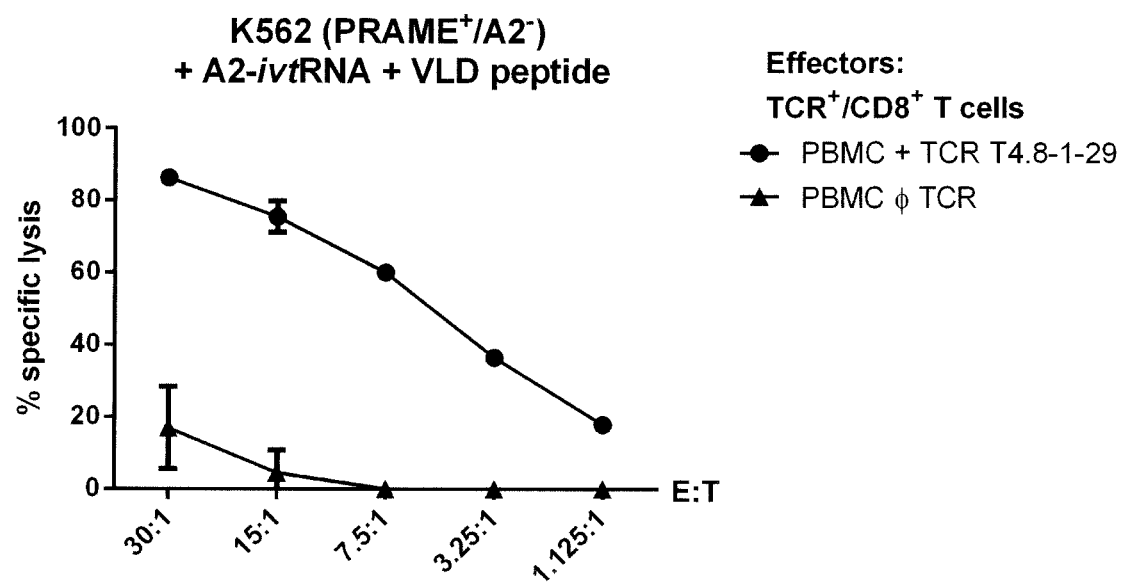
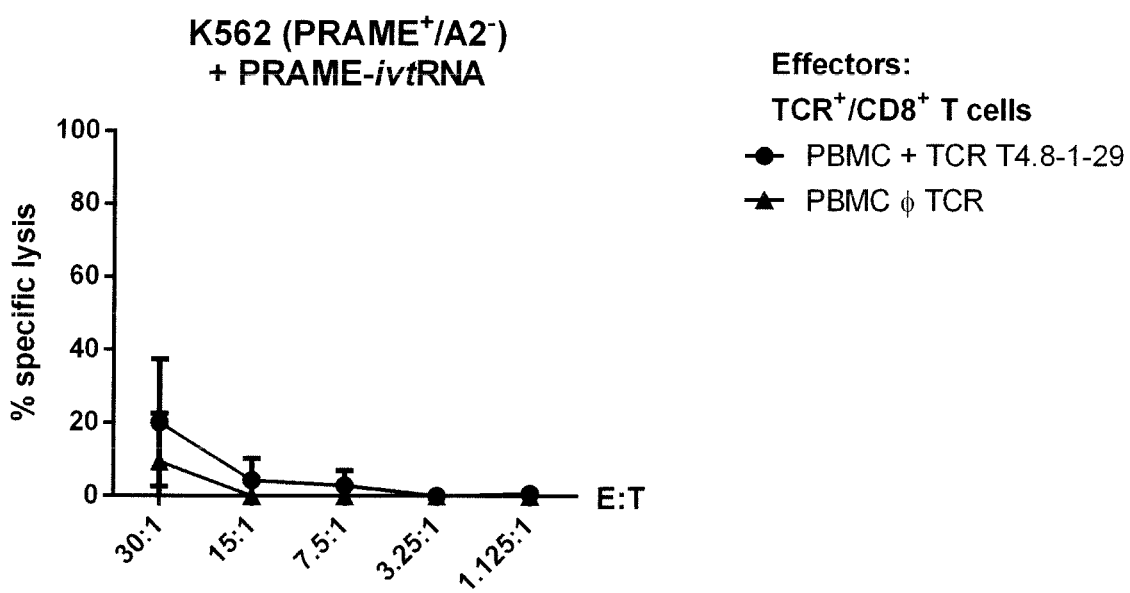

Figure 8 (continued)
C
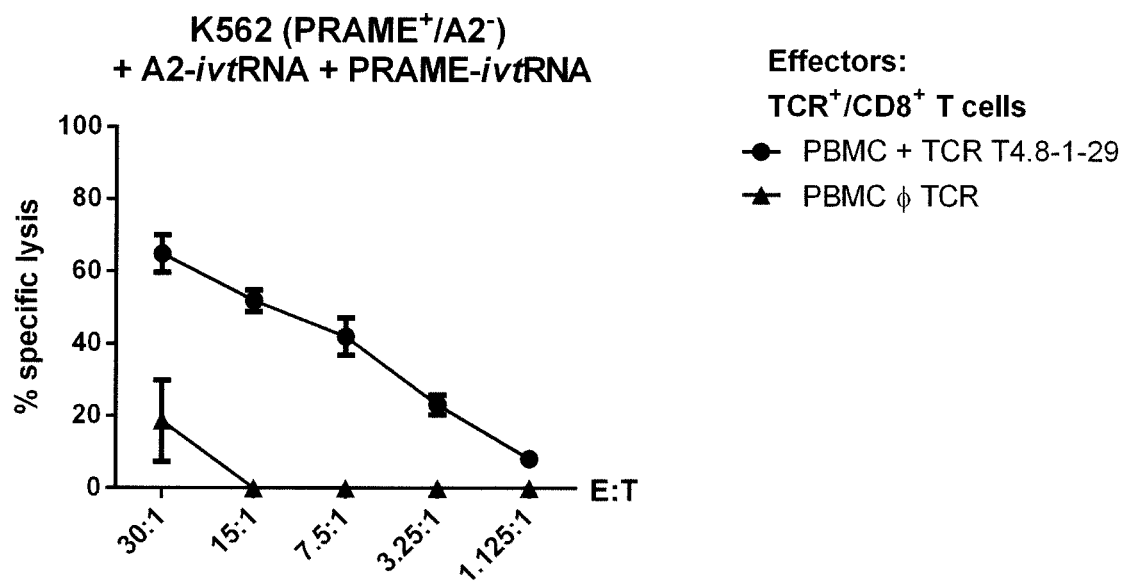
D
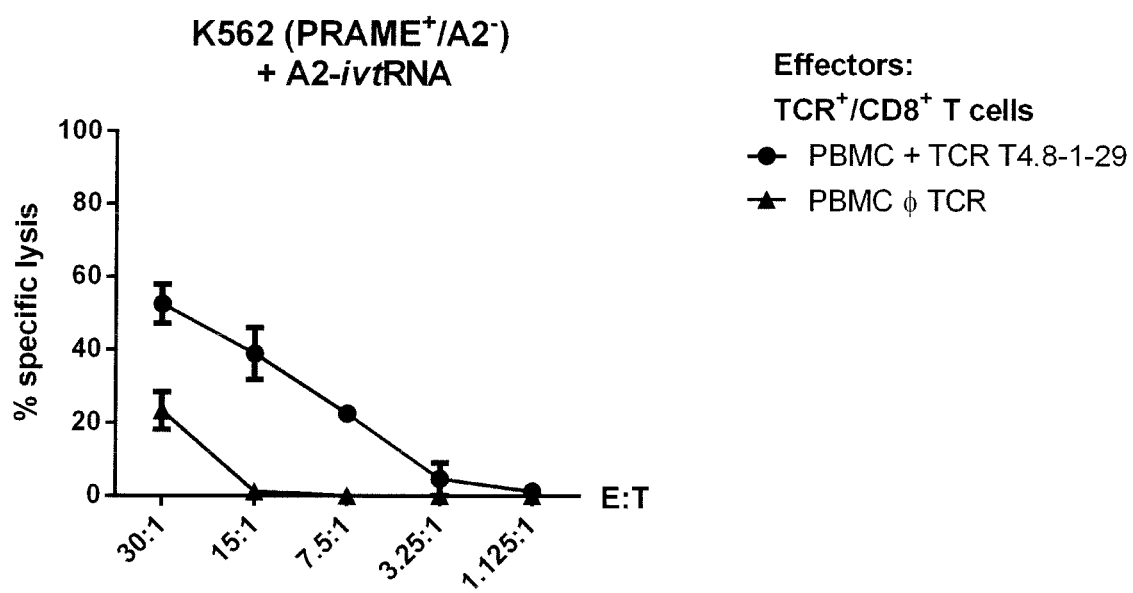

Figure 9

SEQ ID NO: 11 TCR alpha

| | | | | | | |
|---|---|---|---|---|---|---|
| MEKMLECAFI | VLWLQLGWLS | GEDQVTQSPE | ALRLQEGESS | SLNCSYTVSG | LRGLFWYRQD | 60 |
| PGKGPEFLFT | LYSAGEEKEK | ERLKATLTKK | ESFLHITAPK | PEDSATYLCA VHSTAQAGTA | | 120 |
| LIFGKGTTLS | VSSNIQNPDP | AVYQLRDSKS | SDKSVCLFTD | FDSQTNVSQS | KDSDVYITDK | 180 |
| CVLDMRSMDF | KSNSAVAWSN | KSDFACANAF | NNSIIPEDTF | FPSSDVPCDV | KLVEKSFETD | 240 |
| TNLNFQNLSV | IGFRILLLKV | AGFNLLMTLR | LWSS | | | 274 |

SEQ ID NO: 12 TCR beta

| | | | | | | |
|---|---|---|---|---|---|---|
| MGFRLLCCVA | FCLLGAGPVD | SGVTQTPKHL | ITATGQRVTL | RCSPRSGDLS | VYWYQQSLDQ | 60 |
| GLQFLIQYYN | GEERAKGNIL | ERFSAQQFPD | LHSELNLSSL | ELGDSALYFC ASSTHRGQTN | | 120 |
| YGYTFGSGTR | LTVVEDLNKV | FPPEVAVFEP | SKAEIAHTQK | ATLVCLATGF | FPDHVELSWW | 180 |
| VNGKEVHSGV | CTDPQPLKEQ | PALNDSRYCL | SSRLRVSATF | WQNPRNHFRC | QVQFYGLSEN | 240 |
| DEWTQDRAKP | VTQIVSAEAW | GRADCGITSA | SYHQGVLSAT | ILYEILLGKA | TLYAVLVSAL | 300 |
| VLMAMVKRKD | F | | | | | 311 |

SEQ ID NO: 33 (PRAME)

```
       10         20         30         40         50
MERRRLWGSI QSRYISMSVW TSPRRLVELA GQSLLKDEAL AIAALELLPR
       60         70         80         90        100
ELFPPLFMAA FDGRHSQTLK AMVQAWPFTC LPLGVLMKGQ HLHLETFKAV
      110        120        130        140        150
LDGLDVLLAQ EVRPRRWKLQ VLDLRKNSHQ DFWTVWSGNR ASLYSFPEPE
      160        170        180        190        200
AAQPMTKKRK VDGLSTEAEQ PFIPVEVLVD LFLKEGACDE LFSYLIEKVK
      210        220        230        240        250
RKKNVLRLCC KKLKIFAMPM QDIKMILKMV QLDSIEDLEV TCTWKLPTLA
      260        270        280        290        300
KFSPYLGQMI NLRRLLLSHI HASSYISPEK EEQYIAQFTS QFLSLQCLQA
      310        320        330        340        350
LYVDSLFFLR GRLDQLLRHV MNPLETLSIT NCRLSEGDVM HLSQSPSVSQ
      360        370        380        390        400
LSVLSLSGVM LTDVSPEPLQ ALLERASATL QDLVFDECGI TDDQLLALLP
      410        420        430        440        450
SLSHCSQLTT LSFYGNSISI SALQSLLQHL IGLSNLTHVL YPVPLESYED
      460        470        480        490        500
IHGTLHLERL AYLHARLREL LCELGRPSMV WLSANPCPHC GDRTFYDPEP

ILCPCFMPN
```

T CELL RECEPTORS AND USES THEREOF

SEQUENCE LISTING

The instant application contains a Sequence Listing which has been submitted in ASCII format via EFS-Web and is hereby incorporated by reference in its entirety. Said ASCII copy, created on Sep. 17, 2021, is named SCH-4700-US_SeqListing.txt and is 73 kilobytes in size.

BACKGROUND

T lymphocytes (or T cells) which form part of the cell mediated immune system play a major role in the eradication of pathogens. T cells develop in the thymus and express T cell receptor molecules on their surface that allow the recognition of peptides presented on major histocompatibility complex (MHC) molecules which are expressed on nucleated cells (antigen presentation). Antigens of pathogens, i.e. foreign antigens presented by MHC molecules will elicit a powerful T cell response whereas self-antigens usually do not lead to a T cell response due to a negative selection of self-antigen specific T cells in the thymus during the development of such T cells. The immune system can thus discriminate between nucleated cells presenting foreign- or self-antigens and specifically target and eradicate infected cells via potent cytokine release and cellular cytotoxicity mechanisms of the T cells.

The power of the immune system has been recognized as a promising tool for future cancer therapies. In the last decade, research has begun to exploit the unique properties of T cells by using adoptive cell transfer (ACT), which involves the administration of donor-derived lymphocytes, expanded ex vivo. ACT is an attractive concept for the treatment of cancer because it does not require immune-competence of patients, and the specificity of transferred lymphocytes can be targeted against non-mutated and thus poorly immunogenic tumor antigens that typically fail to effectively trigger autologous T cell responses. Although ACT has been shown to be a promising treatment for various types of cancer, its broad application as clinical treatment has been hampered by the need for custom isolation and characterization of tumor-specific T cells from each patient—a process that can be not only difficult and time-consuming but also often fails to yield high-avidity T cells (Xue et al. Clin Exp Immunol. 2005 February; 139(2): 167-172; Schmitt et al., Hum Gene Ther. 2009 November; 20(11): 1240-1248.

The genetic transfer of tumor antigen-specific T-cell receptors (TCRs) into primary T cells can overcome some of the current limitations of ACT, as it allows for the rapid generation of tumor-reactive T lymphocytes with defined antigen specificity even in immunocompromised patients. However, the identification of suitable T cell clones bearing TCRs that specifically recognize tumor antigens and exhibit the desired anti-tumor effects in vivo is still the topic of ongoing research. Considering that in 2012 about 14.1 million new cases of cancer occurred globally and that cancer currently is the cause of about 14.6% of all human deaths worldwide, novel and efficient treatment options are urgently needed. It is the object of the present invention to comply with the needs set out above.

SUMMARY

The present invention provides antigen-specific T cell receptors as well as nucleic acids, vectors, host cells comprising the same; and various uses and applications thereof.

In a first aspect, the invention relates to a T-cell receptor (TCR) comprising (i) a complementarity determining region 3 (CDR3) of the TCR alpha chain variable region comprising or consisting of the amino acid sequence of CAVHSTAQAGTALIF (SEQ ID NO: 1) or an amino acid sequence having at least 80% identity to SEQ ID NO:1, more preferably at least 85% identity, more preferably 90% or 95% and/or (ii) a CDR3 of the TCR beta chain variable region comprising or consisting of the amino acid sequence of CASSTHRGQTNYGYTF (SEQ ID NO. 2) or an amino acid sequence having at least 80% identity to SEQ ID NO: 2, more preferably at least 85% identity, more preferably 90% or 95% identity.

The TCRs provided herein are capable of binding to an epitope comprised within the amino acid sequence of X1LX2GLDX3LL (SEQ ID NO: 31) or its HLA-A*02 bound form, preferably to the epitope comprised within the amino acid sequence of VLDGLDVLL (SEQ ID NO: 32) or its MHC-bound form. The aforementioned amino acid sequence corresponds to amino acid positions 100 to 108 of PRAME (preferentially expressed antigen in melanoma) which is thought to be expressed by a multitude of different cancers.

TCRs, according to the invention, may for instance comprise (i) a TCR alpha chain variable region comprising or consisting of the amino acid sequence depicted in SEQ ID NO: 15, and/or (ii) a TCR beta chain variable region comprising or consisting of the amino acid sequence depicted in SEQ ID NO: 16. TCRs of the invention may also comprise a constant region in the TCR alpha and/or the TCR beta chain.

In particular, the TCRs provided herein may comprise (i) a TCR alpha chain comprising or consisting of an amino acid sequence selected from any one of SEQ ID NOs: 7, 9, 11 or 13 or an amino acid sequence having at least 80% identity, more preferably at least 85% identity, more preferably 90% or 95% to SEQ ID NO: 7, 9, 11 or 13; and/or (ii) a TCR beta-chain comprising or consisting of an amino acid sequence selected from any one of SEQ ID NOs: 8, 10, 12 or 14 or an amino acid sequence having at least 80% identity, more preferably at least 85% identity, more preferably 90% or 95% to SEQ ID NO: 8, 10, 12 or 14.

TCRs of the invention can have a variety of forms, e.g. the TCR can be a native TCR, a TCR variant, a TCR fragment, or a TCR construct. Heterodimers and multimers comprising TCR alpha and beta chains covalently linked to each other are envisaged herein as well as TCR constructs comprising one or more fusion components. A useful TCR construct comprises for instance a TCR alpha chain, a TCR beta chain (both covalently linked to each other) and an antibody or antibody fragment, such as a svFv, which is directed against an antigen or epitope on the surface of lymphocytes (e.g. CD3, CD28, CD5, CD16 or CD56) and is fused to the TCR chains via a linker.

Other useful moieties that can be covalently linked to the inventive TCRs comprise various labels. The TCRs of the invention can also be provided in soluble form.

Further, the invention provides a nucleic acid encoding any of the TCRs provided herein, said nucleic acid for instance comprising or consisting of the nucleic acid sequence of any one of SEQ ID NOs: 23, 24, 25, 26, 27, 28, 29 or 30.

Further provided herein is a vector, comprising the nucleic acid according to the invention. Exemplary vectors include viral vectors, e.g. lentiviral or gamma-retroviral vectors.

Host cells comprising the TCR, the nucleic acid, or the vector of the invention are also provided herein. Useful host cells include lymphocytes such as cytotoxic T lymphocytes (CTLs), CD8+ T cells, CD4+ T cells, natural killer (NK) cells, natural killer T (NKT) cells, gamma/delta-T-cells.

Moreover, the invention provides a method for obtaining the TCR of the invention.

A pharmaceutical or diagnostic composition comprising the TCR, nucleic acid, vector and/or host cell of the invention is also provided herein. Use of the inventive TCR, nucleic acid, vector, host cell and/or pharmaceutical composition as a medicament or diagnostic agent, and in particular detection, diagnosis, prognosis, prevention and/or treatment of cancer is also envisaged. A useful way of preventing or treating cancer includes the following steps: (a) providing one or more of the TCR, nucleic acid, vector, host cell and/or pharmaceutical composition disclosed herein; and (b) administering one or more of the aforementioned to a subject in need thereof. The invention also envisages the following: (a) providing a sample of a subject, said sample comprising lymphocytes; (b) providing one or more of the TCR, nucleic acid, vector, host cell and/or pharmaceutical composition disclosed herein, and (c) introducing the same into the lymphocytes obtained in step (a) and, thereby, obtaining modified lymphocytes, (d) administering the modified lymphocytes of step (c) to a subject or patient in need thereof.

The invention further relates to an in vitro method of detecting the presence of a cancer in a subject in vitro, comprising (a) providing a sample of a subject, said sample comprising one or more cells; (b) contacting said sample with the TCR, nucleic acid, vector or host cell of the invention, thereby forming a complex, and (c) detecting the complex, wherein detection of the complex is indicative of the presence of the cancer in the subject.

DESCRIPTION OF THE FIGURES

FIG. 8 shows lysis of PRAME$_{100-108}$-expressing target cells by human PBMC expressing the PRAME$_{100-108}$-specific TCR T4.8-1-29. (A) lysis of HLA-A*02:01-transfected, endogenously PRAME positive human K562 tumor cells, additionally loaded with PRAME$_{100-108}$-peptide ("VLD peptide"). (B) HLA-A*02 negative, endogenously PRAME positive human K562 cells additionally transfected with ivtRNA coding for PRAME as negative control are not lysed. (C) shows lysis of HLA-A*02-transfected, endogenously PRAME positive human K562 cells additionally transfected with ivtRNA coding for PRAME. (D) shows lysis of HLA-A*02-transfected, endogenously PRAME positive human K562.

FIG. 9 shows the amino acid sequences of a useful example of a T cell receptor alpha and beta chain (SEQ ID NOs 11 and 12) and the amino acid sequence of human PRAME (SEQ ID NO. 33). In the alpha and beta chain, CDR1 and CDR2 sequences are underlined, CDR3 sequences are in grey and bold, variable regions in regular font, constant region in italics.

(HLA-A-positive and PRAME-positive) and 647-V (HLA-A2-positive and PRAME-negative).

Figure 15:
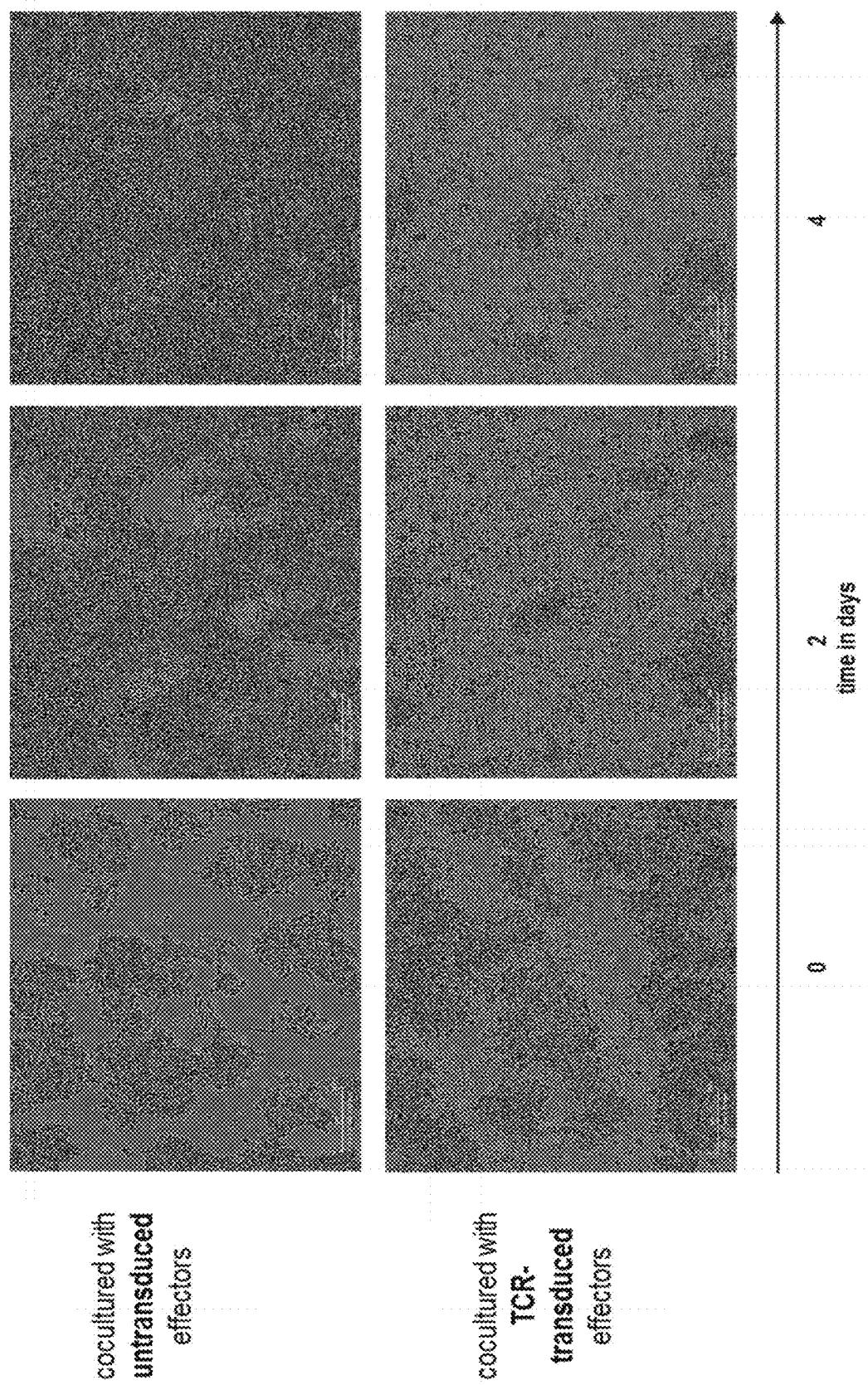

FIG. 15 shows the analysis of cytotoxic activity of T4.8-1-29-transduced effectors against tumor cells using the IncuCyte ZOOM®—Live Cell Analysis System (Essenbiosciences), a microscope-based system that allows live imaging of cells.

Figure 16:
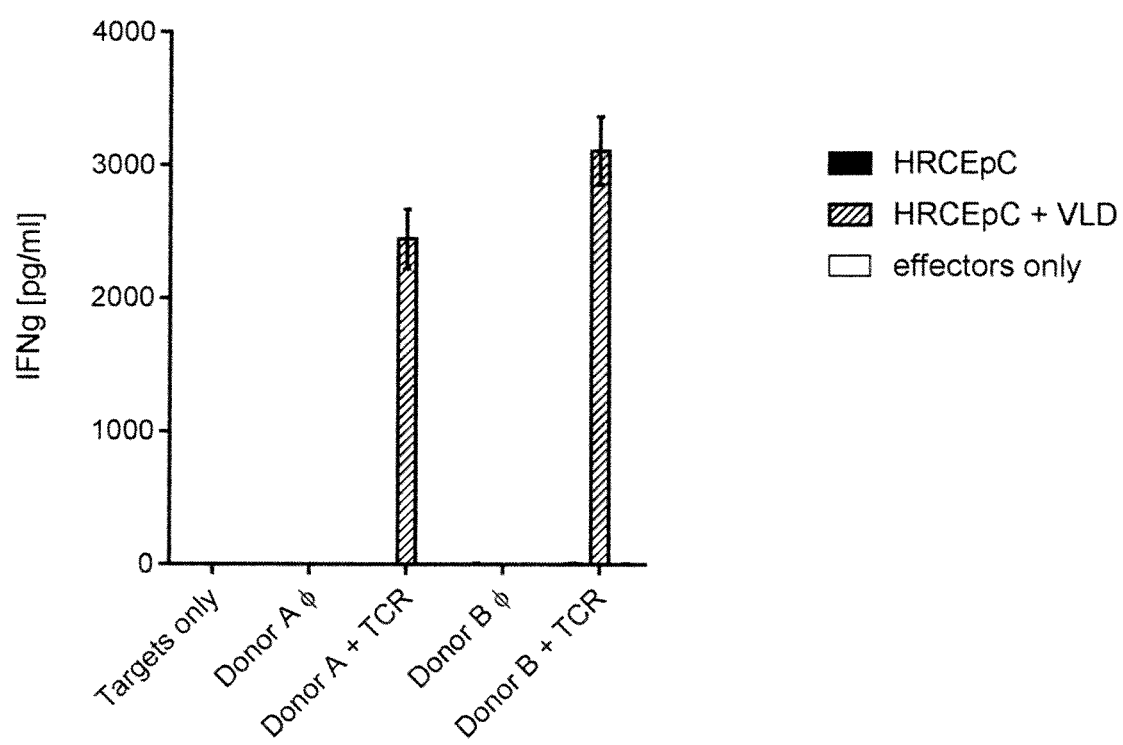

FIG. 16 shows the analysis of the safety profile of T4.8-1-29-expressing PBMC

DETAILED DESCRIPTION

The present inventors have identified T cell clones that are capable of specifically recognizing cells expressing the tumor-associated antigen (TAA) PRAME; and that exhibit advantageous effector functions such as cytokine production and cytolysis of target cells. Said T cell clones and their T cell receptors are therefore promising tools for highly specific and effective cancer treatment. The identified PRAME-specific TCRs are thus suitable for adoptive T cell therapy of cancer. The identification of a TCR that is capable of binding to PRAME in a highly specific manner thus allows for "arming" T cells ex vivo and re-introducing them into the donor where they can effectively recognize and specifically eliminate PRAME expressing cancer cells. Moreover, the antigen binding regions of the novel TCR provided herein can be used to design soluble constructs comprising further functional moieties (such as drugs, labels or further binding domains attracting other immune cells) that are readily available for direct administration.

Variable Region
CDR3 Domains

In a first aspect, the present invention thus relates to a T-cell receptor (TCR) comprising (i) a T cell receptor alpha-chain CDR3 comprising or consisting of the sequence of CAVHSTAQAGTALIF (SEQ ID NO: 1) and/or (ii) a T-cell receptor beta-chain CDR3 comprising or consisting of the amino acid sequence of CASSTHRGQTNYGYTF (SEQ ID NO. 2)

Further envisaged herein are TCR sequence variants comprising a CDR3 alpha comprising or consisting of an amino acid sequence having at least 80% identity, more preferably at least 85% identity, more preferably 90% or 95% to SEQ ID NO: 1 and/or CDR3beta comprising or consisting of an amino acid sequence having at least 80% identity, more preferably at least 85% identity, more preferably 90% or 95% to SEQ ID NO: 2; provided that the TCR retains the advantageous capabilities of the TCR evaluated in the appended examples, i.e. is capable of binding to the antigenic target specified herein.

The term "T cell receptor" or "TCR" as used herein includes native TCRs as well as TCR variants, fragments and constructs. The term thus includes heterodimers comprising TCR alpha and beta chains as well as multimers and single chain constructs; optionally comprising further domains and/or moieties.

In its native form, the TCR exists as a complex of several proteins on the surface of T cells. The T cell receptor is composed of two (separate) protein chains, which are produced from the independent T cell receptor alpha and beta (TCR α and TCR β) genes and are called alpha (α-) and beta (β-) chains. Each chain of the TCR possesses one N-terminal immunoglobulin-like (Ig)-variable (V) domain/region, one Ig-constant-like (C) domain/region, a transmembrane/cell membrane-spanning region anchoring the chain in the plasma membrane, and a short cytoplasmic tail at the C-terminal end.

Antigen specificity is conferred by the variable regions of the alpha and beta chain. Both variable domains of the TCR alpha chain and beta chain comprise three hypervariable or complementarity determining regions (CDR1alpha/beta, CDR2alpha/beta and CDR3 alpha/beta) surrounded by framework (FR) regions. CDR3 is the prime determinant of antigen recognition and specificity (i.e. the ability to recognize and interact with a specific antigen), whereas CDR1 and CDR2 mainly interact with the MHC molecule presenting the antigenic peptide.

Native TCRs recognize antigenic peptides bound to ("presented/displayed on") major histocompatibility complex (MHC) molecules at the surface of an antigen presenting cell. An antigenic peptide presented on a MHC molecule is also referred to as a "peptide:MHC complex" herein. There are two different classes of MHC molecules: MHC I and MHC II, which present peptides from different cellular compartments. MHC class I molecules are expressed on the surface of all nucleated cells throughout the human body and display peptide or protein fragments from intracellular compartments to cytotoxic T cells. In humans, the MHC is also called the human leukocyte antigen (HLA). There are three major types of MHC class I: HLA-A, HLA-B and HLA-C. Once a TCR binds to its specific peptide:MHC complex, the T cell is activated and exerts biological effector functions.

The TCRs provided herein are advantageously capable of (specifically) recognizing PRAME, in particular $PRAME_{100-108}$ in its MHC bound form as will be discussed below in detail. An antigenic peptide is said to be present in its "MHC bound form" when it forms a complex with an MHC molecule (which may be present on the surface of an antigen presenting cell such as a dendritic cell or a tumor cell, or it may be immobilized by for example coating to a bead or plate.)

CDR1 and CDR2 Domains

As set out previously, the TCRs of the invention are particularly envisaged to recognize their antigenic target $PRAME_{100-108}$ when being presented on an MHC molecule, specifically an MHC-1 molecule, and in particular HLA-A, preferably HLA-A*02 and specifically HLA-A2 molecules encoded by the allele HLA-A*02:01 (the T cell or TCR is said to be "restricted" to a particular MHC molecule). It is also conceivable that the TCRs of the invention recognize their antigenic target presented on other HLA-A*02 alleles. As noted previously, CDR1 and CDR2 of the TCR alpha and beta chains are thought to be mainly involved in MHC recognition. There is a limited "pool" of CDR1 and CDR2 sequences known to be involved in HLA-A*02-restricted antigen recognition, and it is envisaged that the CDR3 domains of the present invention can in principle be combined with any of the CDR1 and CDR2 domains depicted in SEQ ID NO: 34-224, provided that the TCR retains its ability to recognize its antigenic target, preferably in its HLA-A*02 bound form, to a similar, the same or even a higher extent as the TCR evaluated in the appended examples. Useful examples of CDR1 and CDR2 domains include the CDR1 alpha comprising or consisting of the sequence VSGLRG as depicted in SEQ ID NO: 5, the CDR2 alpha comprising or consisting of the sequence LYSAGEE as depicted in SEQ ID NO: 3, the CDR1 beta comprising or consisting of the sequence SGDLS as depicted in SEQ ID NO: 6, and the CDR2 beta comprising or consisting of the sequence YYNGEE as depicted in SEQ ID NO: 4. Said CDR sequences are also shown in FIG. 9.

In accordance with the foregoing, the present invention inter alia provides TCRs comprising two polypeptide chains, each of which comprises a human variable region comprising at least one complementarity determining region (i.e. in particular CDR3, and preferably a CDR1, and/or CDR2) of a TCR. A TCR with particular advantageous properties (as shown in the appended examples) comprises a first polypeptide chain comprising a CDR1 comprising or consisting of the amino acid sequence of SEQ ID NO: 5 (CDR1 alpha), a CDR2 comprising or consisting of the amino acid sequence of SEQ ID NO: 3 (CDR2 alpha), and a CDR3 comprising or consisting of the amino acid sequence of SEQ ID NO: 1 (CDR3 alpha), and second polypeptide chain comprising a CDR1 comprising or consisting of the amino acid sequence of SEQ ID NO: 6 (CDR1 beta), a CDR2 comprising or consisting of the amino acid sequence of SEQ ID NO: 4 (CDR2 beta), and a CDR3 comprising or consisting of the amino acid sequence of SEQ ID NO: 2 (CDR3 beta).

Complete Variable Regions

The present invention further provides a TCR comprising a TCR alpha chain variable region comprising or consisting of an amino acid sequence as depicted in SEQ ID NO: 15 and/or a TCR beta chain variable region comprising or consisting of an amino acid sequence as depicted in SEQ ID NO: 16. Said alpha and beta chain sequences are also shown in FIG. 9 (normal font).

TCR sequence variants comprising alpha chain variable regions comprising an amino acid sequence having at least 80% identity, more preferably at least 85% identity, more preferably 90% or 95% to SEQ ID NO: 15 and/or a TCR beta chain variable region comprising or consisting of an amino acid sequence having at least 80% identity, more preferably at least 85% identity, more preferably 90% or 95% to SEQ ID NO: 16 are also envisaged herein; provided that the TCR retains the advantageous capabilities of the TCR evaluated in the appended examples, i.e. is capable of binding to the antigenic target specified herein.

Constant Region

The TCR may further comprise a constant (C) region in its alpha and/or beta chain. The constant region can be a human constant region or derived from another species, yielding a "chimeric" TCR. For instance, human alpha and/or beta chains can be replaced by their murine counterparts ("murinization") which has been found to enhance surface expression of human TCRs by supporting preferential pairing of the TCR alpha and beta chains, and a more stable association with the CD3 co-receptor. Suitable constant regions of the alpha chain can for instance be selected from SEQ ID NOs: 17 (human), 19 (minimal murinized) and 21 (murine). Suitable constant regions of the beta chain can be selected from SEQ ID NOs: 18 (human), 20 (minimal murinized) and 22 (murine). Instead of replacing complete human constant regions by their murine counterparts, it is also possible to exchange only some amino acids in the human constant regions for the corresponding amino acids of the murine constant region ("minimal murinization"), as further explained in the section "TCR sequence variants" herein.

Alpha and Beta Chains

Useful examples of TCRs of the invention include those comprising an alpha chain comprising or consisting of an amino acid sequence as depicted in SEQ ID NO: 7, 9, 11 or 13 and a beta chain comprising or consisting of an amino acid sequence as depicted in SEQ ID NO: 8, 10, 12 or 14. The present invention thus provides, inter alia, a TCR comprising or consisting of an alpha chain comprising or consisting of an amino acid sequence as depicted in SEQ ID NO: 7 and a beta chain comprising or consisting of an amino acid sequence as depicted in SEQ ID NO: 8; a TCR comprising or consisting of an alpha chain comprising or consisting of an amino acid sequence as depicted in SEQ ID NO: 9 and a beta chain comprising or consisting of an amino acid sequence as depicted in SEQ ID NO: 10; a TCR comprising or consisting of an alpha chain comprising or consisting of an amino acid sequence as depicted in SEQ ID NO: 11 and a beta chain comprising or consisting of an amino acid sequence as depicted in SEQ ID NO: 12 (both also shown in FIG. 9); and a TCR comprising or consisting of an alpha chain comprising or consisting of an amino acid sequence as depicted in SEQ ID NO: 13 and a beta chain comprising or consisting of an amino acid sequence as depicted in SEQ ID NO: 14.

TCR sequence variants comprising alpha chains comprising an amino acid sequence having at least 80% identity, more preferably at least 85% identity, more preferably 90% or 95% to SEQ ID NO: 7, 9, 11 or 13 and/or a TCR beta chain comprising or consisting of an amino acid sequence having at least 80% identity, more preferably at least 85% identity, more preferably 90% or 95% to SEQ ID NO: 8, 10, 12 or 14 are also envisaged herein; provided that the TCR retains the advantageous capabilities of the TCR evaluated in the appended examples, i.e. is capable of binding to the antigenic target specified herein.

Antigenic Target

The TCRs provided herein are advantageously capable of binding to (human) PRAME. PRAME (Melanoma antigen preferentially expressed in tumors, Uniprot Acc. No. P78395), also referred to as MAPE (melanoma antigen preferentially expressed in tumors) and OIP4 (OPA-interacting protein 4), has been reported a cancer-testis antigen (CTA) with unknown function.

In particular, the present invention provides TCRs that are capable of (specifically) binding to an epitope comprised within an amino acid sequence corresponding to amino acid positions 100-108 of the PRAME amino acid sequence as depicted in SEQ ID NO: 33 (FIG. 9) in bold, The PRAME peptide consisting of the amino acid sequence as depicted in SEQ ID NO: 32 is also referred to as $PRAME_{100-108}$ or the "antigenic target" or "VLD peptide" herein. As set out elsewhere herein, the TCR—of the invention will preferably recognize $PRAME_{100-108}$ when bound by MHC, in particular HLA-A*02.

The term "position" when used in accordance with the disclosure means the position of either an amino acid within an amino acid sequence depicted herein or the position of a nucleotide within a nucleic acid sequence depicted herein. The term "corresponding" as used herein also includes that a position is not only determined by the number of the preceding nucleotides/amino acids, but is rather to be viewed in the context of the circumjacent portion of the sequence. Accordingly, the position of a given amino acid or nucleotide in accordance with the disclosure may vary due to deletion or addition of amino acids or nucleotides elsewhere in the sequence. Thus, when a position is referred to as a "corresponding position" in accordance with the disclosure it is understood that nucleotides/amino acids may differ in terms of the specified numeral but may still have similar neighboring nucleotides/amino acids. In order to determine whether an amino acid residue (or nucleotide) in a given sequence corresponds to a certain position in the amino acid sequence of a "parent" amino acid/nucleotide sequence, the skilled person can use means and methods well-known in the art, e.g., sequence alignments, either manually or by using computer programs such as exemplified herein.

The term "epitope" in general refers to a site on an antigen, typically a (poly-) peptide, which a binding domain recognizes. The term "binding domain" in its broadest sense refers to an "antigen binding site", i.e. characterizes a domain of a molecule which binds/interacts with a specific epitope on an antigenic target. An antigenic target may comprise a single epitope, but typically comprises at least two epitopes, and can include any number of epitopes depending on the size, conformation, and type of antigen. The term "epitope" in general encompasses linear epitopes and conformational epitopes. Linear epitopes are contiguous epitopes comprised in the amino acid primary sequence and typically include at least 2 amino acids or more. Conformational epitopes are formed by non-contiguous amino acids juxtaposed by folding of the target antigen, and in particular target (poly-) peptide.

In the context of the present invention the term "binding domain" in particular refers to the variable region of the TCR alpha and/or beta chain and specifically the CDR3alpha and CDR3beta of the TCR.

The present inventors have found that the minimal amino acid sequence recognized by the TCRs of the invention corresponds to the amino acid sequence X1LX2GLDX3LL (SEQ ID NO: 31), with X being selected from any amino acid. Specifically, the inventive TCRs has been shown to (specifically) recognize the amino acid sequence comprising or consisting of the amino acid sequence VLDGLDVLL (SEQ ID NO: 32), as shown in the appended examples. The TCRs of the invention are thus capable of binding to an amino acid sequence comprising or consisting of the amino acid sequence X1LX2GLDX3LL (SEQ ID NO: 31), preferably comprising or consisting of the amino acid sequence VLDGLDVLL (SEQ ID NO: 32) or its MHC bound form. For instance, it is envisaged that the recognized peptide may comprise further C amino acids located C- and/or N-terminal of the recognition motif depicted in SEQ ID NO: 31 and in particular SEQ ID NO: 32. Specifically, the TCR described herein is envisaged to recognize at least one epitope within the aforementioned amino acid sequences. The terms "binding to" and "recognizing" in all grammatical forms are used interchangeably herein. The antigenic target is particularly envisaged to be recognized by the inventive TCR when being bound by a MHC class I molecule, specifically a HLA-A molecule, and preferably a HLA-A*02 molecule, in particular a HLA-A*02:01 molecule. Said MHC molecule, in particular HLA-A and HLA-A*02 molecule, can be present on the surface of a cell, for instance a tumor cell, or on a (solid) carrier.

Preferably, the inventive TCRs specifically bind to their antigenic target. The term "specific(ally) binding" generally indicates that a TCR binds via its antigen binding site more readily to its intended antigenic target than to a random, unrelated non-target antigen. Particularly the term "specifically binds" indicates that the binding specificity of the TCR will be at least about 5-fold, preferably 10-fold, more preferably 25-fold, even more preferably 50-fold, and most preferably 100-fold or more, greater for its antigenic target than its binding specificity for a non-target antigen.

Effector host cells expressing a native TCR as described herein are envisaged to bind to their antigenic target (i.e. preferably $PRAME_{100-108}$ presented on HLA-A*02 by antigen presenting cells) with a high functional avidity. The term "functional avidity" refers to the capability of TCR expressing cells (in particular T-cells expressing native TCRs as described herein) to respond in vitro to a given concentration of a ligand and is thought to correlate with the in vivo effector capacity of TCR expressing cells. By definition, TCR expressing cells with high functional avidity respond in in vitro tests to very low antigen doses, while such cells of lower functional avidity require higher amounts of antigen before they mount an immune response similar to that of high-avidity TCR expressing cells. The functional avidity can be therefore considered as a quantitative determinant of the activation threshold of a TCR expressing cell. It is determined by exposing such cells in vitro to different amounts of cognate antigen. TCR expressing cells with high functional avidity respond to low antigen doses. For example, a TCR expressing cell will typically be considered to bind with "high" functional avidity to its antigenic target if it secretes at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, or 20,000 pg/mL or more) of interferon gamma (IFN-gamma) upon co-culture with antigen-negative HLA-A*02 expressing target cells loaded with a low concentration of the $PRAME_{100-108}$ peptide ranging from about $10^{-5}$ to about $10^{-11}$ M (i.e., about 0.05 ng/mL to about 5 ng/mL, 0.05 ng/mL, 0.1 ng/mL, 0.5 ng/mL, 1 ng/mL, or 5 ng/mL) with a molecular weight of the $PRAME_{100-108}$ peptide of 956 g/mol.

Other methods to determine specific binding of the inventive TCRs include the $^{51}$Cr-release assay described by Gertner-Dardenne et al. J Immunol 188(9): 4701-4708, CD107a/b mobilization described by Leisegang et al., Clin. Cancer Res 2010. 16: 2333-2343 and peptide:MHC multimer binding analyses described by Wilde et al., J Immunol 2012; 189:598-605.

Variants

As noted previously, the term "TCR" encompasses TCR variants, which include TCR sequence variants, fragments and constructs. All TCR variants are envisaged to be functional variants of the inventive TCR. The term "functional variant" as used herein refers to a TCR, polypeptide, or protein having substantial or significant sequence identity or similarity to a parent TCR, its variable regions or its antigen-binding regions and shares its biological activity, i.e. its ability to specifically bind to the antigenic target for which the parent TCR of the invention has antigenic specificity to a similar, the same or even a higher extent as the TCR disclosed herein and evaluated in the appended examples.

Sequence Variants

The term "TCR variants" includes "sequence variants" of the TCRs disclosed herein, i.e. variants substantially comprising the amino acid sequence of the inventive TCR as described above (also referred to as the "parent" TCR) but containing at least one amino acid modification (i.e. a substitution, deletion, or insertion) as compared to the "parent" TCR amino acid sequence, provided that the variant preferably retains the antigenic specificity of the inventive "patent" TCR. TCR sequence variants of the invention are typically prepared by introducing appropriate nucleotide changes into the nucleic acids encoding the "parent" TCR, or by peptide synthesis. Generally, the aforementioned amino acid modifications may be introduced into, or present in, the variable region or the constant region of the TCR, and may serve to modulate properties like binding strength and specificity, post-translational processing (e.g. glycosylation), thermodynamic stability, solubility, surface expression or TCR assembly.

As set out previously, amino acid modifications include, for example, deletions from, and/or insertions into, and/or substitutions of, residues within the amino acid sequences of the parent TCR. Exemplary insertional variants of a TCR of the invention include fusion products of said TCR and an enzyme or another functional polypeptide. Exemplary substitutional variants of a TCR of the invention are those including amino acid substitutions in variable regions or CDRs of the alpha and/or beta chain, the framework region or the constant region. Particularly envisaged herein are conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be in an acidic amino acid substituted for another acidic amino acid (e.g., Asp or Glu), an amino acid with a nonpolar side chain substituted for another amino acid with a nonpolar side chain (e.g., Ala, Gly, Val, He, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gin, Ser, Thr, Tyr, etc.), etc. that may be made, for instance, on the basis of similarity in polarity, charge, solubility, hydrophobicity, hydrophilicity, and/or the amphipathic nature of the residues involved.

Cysteine Modification

The addition of a disulfide bond in the constant region has been reported to foster correct pairing of the TCR alpha and beta chains (Kuball J et al. Blood. 2007 Mar. 15; 109(6): 2331-8). Thus, the addition of one or more cysteine bonds in the constant region is also envisaged herein.

Murinization

As noted previously, murinization of TCRs (i.e. exchanging the human constant regions in the alpha and beta chain by their murine counterparts) is a technique that is commonly applied in order to improve cell surface expression of TCRs in host cells. Without wishing to be bound by specific theory, it is thought that murinized TCRs associate more effectively with CD3 co-receptors; and/or that preferentially pair with each other and are less prone to form mixed TCRs on human T cells engineered ex vivo to express the TCRs of desired antigenic specificity, but still retaining and expressing their "original" TCRs.

Recently nine amino acids responsible for the improved expression of murinized TCRs have been identified (Sommermeyer and Uckert, J Immunol. 2010 Jun. 1; 184(11): 6223-31) and it is envisaged to substitute one or all of the amino acid residues in the TCRs alpha and/or beta chain constant region for their murine counterpart residues. This technique is also referred to as "minimal murinization", and offers the advantage of enhancing cell surface expression while, at the same time, reducing the number of "foreign" amino acid residues in the amino acid sequence and, thereby, the risk of immunogenicity.

In general, TCR sequence variants are envisaged to comprise at least one of the CDR1, CDR2, CDR3, alpha chain variable regions, beta chain variable regions, alpha chains and/or beta chains as disclosed herein, or comprising or consisting of an amino acid sequence that is at least about 80%, about 85%, about 90%, about 95%, about 96%, about 97%, about 98%, about 99%, or identical to the amino acid sequences disclosed herein, provided that said variants exhibit comparable, the same or improved binding characteristics as compared to TCR evaluated in the appended examples.

As used herein the term "sequence identity" indicates the extent to which two (nucleotide or amino acid) sequences have identical residues at the same positions in an alignment, and is often expressed as a percentage. Preferably, identity is determined over the entire length of the sequences being compared. Thus, two copies of exactly the same sequence have 100% identity, but sequences that are less highly conserved and have deletions, additions, or replacements, may have a lower degree of identity. Those skilled in the art will recognize that several algorithms are available for determining sequence identity using standard parameters, for example Blast (Altschul, et al. (1997) Nucleic Acids Res. 25:3389-3402), Blast2 (Altschul, et al. (1990) J. Mol. Biol. 215:403-410), Smith-Waterman (Smith, et al. (1981) J. Mol. Biol. 147:195-197) and ClustalW.

Accordingly, the amino acid sequences of SEQ ID Nos: 1 or 2, can for instance serve as "subject sequence" or "reference sequence", while the amino acid sequence of a CDR3 different therefrom can serve as "query sequence".

Constructs and Fragments

The term "TCR" as used herein further comprises TCR constructs. The term "construct" includes proteins or polypeptides comprising at least one antigen binding domain of the inventive TCRs, but do not necessarily share the basic structure of a native TCR (i.e. variable domains incorporated into a TCR alpha chain and a TCR beta chain forming a heterodimer). TCR constructs and fragments are typically obtained by routine methods of genetic engineering and are often artificially constructed to comprise additional functional protein or polypeptide domains. In accordance with the foregoing, TCR constructs and fragments of the invention are envisaged to comprise at least one CDR3alpha and/or at least one CDR3beta as disclosed elsewhere herein. Further envisaged herein are constructs and fragments comprising at least one CDR1alpha, CDR2alpha, CDR1beta, CDR2beta, alpha chain variable region, beta chain variable region, alpha chain and/or beta chain, or combinations thereof, optionally in combination with further protein domains or moieties as exemplified herein. The TCR constructs and fragments provided herein are envisaged to be capable of specifically binding to the same antigenic target as the inventive TCRs described above and evaluated in the appended Examples.

Multimers

The term "TCR construct" encompasses heterodimers and multimers in which at least one TCR alpha chain variable region or TCR alpha-chain and at least one TCR beta-chain variable region are covalently linked to each other. In its simplest form a multivalent TCR construct according to the invention comprises a multimer of two or three or four or more TCRs associated (e. g. covalently or otherwise linked) with one another, preferably via a linker molecule.

Suitable linker molecules include, but are not limited to, multivalent attachment molecules such as avidin, streptavidin, neutravidin and extravidin, each of which has four binding sites for biotin. Thus, biotinylated TCRs can be formed into multimers having a plurality of TCR binding sites. The number of TCRs in the multimer will depend upon the quantity of TCR in relation to the quantity of linker molecule used to make the multimers, and also on the presence or absence of any other biotinylated molecules. Exemplary multimers are dimeric, trimeric, tetrameric or pentameric or higher-order multimer TCR constructs. Multimers of the invention may also comprise further functional entities such as labels or drugs or (solid) carriers.

The term "TCR construct" also encompasses TCR molecules which are linked via a suitable linker to a spheric body, preferably a uniform bead, more preferably a polystyrene bead, most preferably a bio-compatible polystyrene bead. Such TCR constructs can also be comprised of an inventive TCR and a bead having a pre-defined fluorescence dye incorporated into the bead.

Fusion Proteins

The term "TCR construct" also relates to fusion proteins or polypeptides comprising at least one TCR alpha chain, TCR alpha chain variable region or CDR3alpha and/or at least one TCR beta chain, TCR beta chain variable region or CDR3beta; and further one or more fusion component(s). Useful components include Fc receptors; Fc domains (derived from IgA, IgD, IgG, IgE, and IgM); cytokines (such as IL-2 or IL-15); toxins; antibodies or antigen-binding fragments thereof (such as anti-CD3, anti-CD28, anti-CD5, anti-CD16 or anti-CD56 antibodies or antigen-binding fragments thereof); CD247 (CD3-zeta), CD28, CD137, CD134 domains; or any combinations thereof.

Exemplary antibody fragments that can be used as fusion components include fragments of full-length antibodies, such as (s)dAb, Fv, Fd, Fab, Fab', F(ab')2 or "r IgG" ("half antibody"); modified antibody fragments such as scFv, di-scFv or bi(s)-scFv, scFv-Fc, scFv-zipper, scFab, Fab2, Fab3, diabodies, single chain diabodies, tandem diabodies (Tand-ab's), tandem di-scFv, tandem tri-scFv, minibodies, multibodies such as triabodies or tetrabodies, and single domain antibodies such as nanobodies or single variable domain antibodies comprising only one variable domain, which might be $V_HH$, $V_H$ or $V_L$.

TCR constructs of the invention may be fused to one or more antibody or antibody fragments, yielding monovalent, bivalent and polyvalent/multivalent constructs and thus monospecific constructs, specifically binding to only one target antigen as well as bispecific and polyspecific/multispecific constructs, which specifically bind more than one target antigens, e.g. two, three or more, through distinct antigen binding sites.

Optionally, a linker may be introduced between the one or more of the domains or regions of the TCR construct of the invention, i.e. between the TCR alpha chain CDR3, TCR alpha chain variable region, and/or a TCR alpha chain, the TCR beta chain CDR3, TCR beta chain variable region, and/or a TCR beta chain, and/or the one or more fusion component(s) described herein. Linkers are known in the art and have been reviewed, inter alia, by Chen et al. Adv Drug Deliv Rev. 2013 Oct. 15; 65(10): 1357-1369. In general, linkers include flexible, cleavable and rigid linkers and will be selected depending on the type of construct and intended use/application. For example, for therapeutic application, non-immunogenic, flexible linkers are often preferred in order to ensure a certain degree of flexibility or interaction between the domains while reducing the risk of adverse immunogenic reactions. Such linkers are generally composed of small, non-polar (e.g. Gly) or polar (e.g. Ser or Thr) amino acids and include "GS" linkers consisting of stretches of Gly and Ser residues. An example of the most widely used flexible linker which is also intended for use in the TCR construct of the present invention has the sequence of (Gly-Gly-Gly-Gly-Ser)$_n$ (SEQ ID NO: 225) Other suitable linkers include for instance KESGSVSSEQLAQFRSLD (SEQ ID NO: 226) and EGKSSGSGSESKST (SEQ ID NO: 227) and GSAGSAAGSGEF (SEQ ID NO: 228).

Particularly useful TCR constructs envisaged in accordance with the invention are those comprising at least one TCR alpha chain, TCR alpha chain variable region or CDR3 alpha as defined herein, at least one TCR beta chain, TCR beta chain variable region or CDR3 beta as defined herein, optionally linked to each other and fused, optionally via a liker, to at least one antibody or an antibody fragment (such as a single chain antibody fragment (scFv)) directed against an antigen or epitope on the surface of lymphocytes. Useful antigenic targets recognized by the antibody or antibody fragment (e.g. scFv) include CD3, CD28, CD5, CD16 and CD56. Said construct can in general have any structure as long the "TCR portion" (i.e. TCR alpha and beta chain or variable regions or CDR3s thereof) retains its ability to recognize the antigenic target defined herein, and the "antibody portion" binds to the desired surface antigen or epitope, thereby recruiting and targeting the respective lymphocyte to the target cell. Such constructs may advantageously serve as "adapters" joining an antigen presenting cell displaying the antigenic target (such as a tumor cell) and a lymphocyte (such as a cytotoxic T cell or NK cell) together. An example of such a fusion protein is a construct engineered according to the principle of a bi-specific T-cell engager (BiTE®) consisting of two single-chain variable fragments (scFvs) of different antibodies, on a single peptide chain of about 55 kilodaltons (kD). Accordingly, a TCR construct of the invention may comprise at least one TCR antigen binding domain as described herein (for instance a TCR variable alpha and variable beta chain fused to each other) linked to a scFv (or other binding domain) of the desired binding specificity, e.g. CD3 or CD56. The scFv (or other binding domain) binds to T cells such as via the CD3 receptor or to CD56 for NK cell activation, and the other to a tumor cell via an antigenic target specifically expressed on the tumor cell. Also envisaged herein are tribodies comprising at least one TCR antigen binding domain as described herein, an scFv (or other binding domain) and a further domain e.g. for targeting the construct to a site of action within the body (e.g. an Fc domain).

Isolated Form

The TCRs of the invention may be provided in "isolated" or "substantially pure" form. "Isolated" or "substantially pure" when used herein means that the TCRs have been identified separated and/or recovered from a component of its production environment, such that the "isolated" TCR is free or substantially free of other contaminant components from its production environment that might interfere with its therapeutic or diagnostic use. Contaminant components may include enzymes, hormones, and other proteinaceous or non-proteinaceous solutes. "Isolated" TCRs will thus be prepared by at least one purification step removing or substantially removing these contaminant components. The aforementioned definition is equally applicable to "isolated" polynucleotides/nucleic acids, mutatis mutandis.

Soluble Forms

The TCRs of the present invention can be provided in soluble form. Soluble TCRs are useful as diagnostic tools, and carriers or "adapters" that specifically target therapeutic agents or effector cells to, for instance, a cancer cell expressing the antigenic target recognized by the soluble TCR. Soluble TCRs (sTCRs) will typically be fragments or constructs comprising TCR alpha and/or beta chains, or variable regions or CDRs thereof and optionally stabilized via disulfide bonds or covalently linked via a suitable linker molecule, e.g. as described above in the context of TCR constructs of the invention. They will typically not comprise e.g. a transmembrane region. In some circumstances amino acid modifications in the polypeptide sequence may be introduced in order to enhance solubility of the molecules, and/or correct folding and pairing of the alpha and beta chains (if desired), in particular when produced in a recombinant host that does not provide for the aforementioned features. For instance, when using *E. coli* as production host cells, folding and pairing of the TCR alpha and beta chains is typically accomplished in vitro. TCRs according to the invention may therefore for instance comprise additional cysteine residues, as described elsewhere herein.

Besides additional cysteine bridges, other useful modifications include, for instance, the addition of leucine zippers and/or ribosomal skipping sequences, e.g. sequence 2A from picorna virus as described in Walseng et al. (2015), PLoS ONE 10(4): e0119559 to increase folding, expression and/or pairing of the TCR alpha and/or beta chains.

Modifications

The TCRs of the invention may further comprise one or more modifications as described in the following. The modifications described below will typically be covalent modifications and can be accomplished using standard techniques known in the art. In some circumstances, amino acid modifications in the TCRs may be required in order to facilitate the introduction of said modifications.

Labels

The TCRs, in particular (soluble) TCRs, of the invention can be labelled. Useful labels are known in the art and can be coupled to the TCR or TCR variant using routine methods, optionally via linkers of various lengths. The term "label" or "labelling group" refers to any detectable label. In general, labels fall into a variety of classes, depending on the assay in which they are to be detected—the following examples include, but are not limited to: isotopic labels, which may be radioactive or heavy isotopes, such as radioisotopes or radionuclides (e.g., $^{3}H$, $^{14}C$, $^{15}N$, $^{35}S$, $^{89}Zr$, $^{90}Y$, $^{99}Tc$, $^{111}In$, $^{125}I$, $^{131}I$); magnetic labels (e.g., magnetic particles); redox active moieties; optical dyes (including, but not limited to, chromophores, phosphors and fluorophores) such as fluorescent groups (e.g., FITC, rhodamine, lanthanide phosphors), chemiluminescent groups, and fluorophores which can be either "small molecule" fluorophores or proteinaceous fluorophores; enzymatic groups (e.g. horseradish peroxidase, β-galactosidase, luciferase, alkaline phosphatase; biotinylated groups; or predetermined polypeptide epitopes recognized by a secondary reporter (e.g., leucine zipper pair sequences, binding sites for secondary antibodies, metal binding domains, epitope tags, etc.). Labelling is particularly envisaged when the TCRs, TCR variants or especially soluble TCR constructs (such as those comprising at least one TCR alpha and/or TCR beta chain as described herein) are intended for diagnostic use.

Functional Moieties

The TCRs, in particular soluble TCRs, of the invention can be modified by attaching further functional moieties, e.g. for reducing immunogenicity, increasing hydrodynamic size (size in solution) solubility and/or stability (e.g. by enhanced protection to proteolytic degradation) and/or extending serum half-life.

Exemplary functional moieties for use in accordance with the invention include peptides or protein domains binding to other proteins in the human body (such as serum albumin, the immunoglobulin Fc region or the neonatal Fc receptor (FcRn), polypeptide chains of varying length (e.g., XTEN technology or PASylation®), non-proteinaceous polymers, including, but not limited to, various polyols such as polyethylene glycol (PEGylation), polypropylene glycol, polyoxyalkylenes, or copolymers of polyethylene glycol and polypropylene glycol, or of carbohydrates, such as hydroxyethyl starch (e.g., HESylation®) or polysialic acid (e.g., PolyXen® technology).

Other useful functional moieties include "suicide" or "safety switches" that can be used to shut off effector host cells carrying an inventive TCR in a patient's body. An example is the inducible Caspase 9 (iCasp9) "safety switch" described by Gargett and Brown Front Pharmacol. 2014; 5: 235. Briefly, effector host cells are modified by well-known methods to express a Caspase 9 domain whose dimerization depends on a small molecule dimerizer drug such as AP1903/CIP, and results in rapid induction of apoptosis in the modified effector cells. The system is for instance described in EP2173869 (A2). Examples for other "suicide" "safety switches" are known in the art, e.g. Herpes Simplex Virus thymidine kinase (HSV-TK), expression of CD20 and subsequent depletion using anti-CD20 antibody or myc tags (Kieback et al, Proc Natl Acad Sci USA. 2008 Jan. 15; 105(2):623-8).

Glycosylation

TCRs with an altered glycosylation pattern are also envisaged herein. As is known in the art, glycosylation patterns can depend on the amino acid sequence (e.g., the presence or absence of particular glycosylation amino acid residues, discussed below) and/or the host cell or organism in which the protein is produced. Glycosylation of polypeptides is typically either N-linked or O-linked. N-linked refers to the attachment of the carbohydrate moiety to the side chain of an asparagine residue. Addition of N-linked glycosylation sites to the binding molecule is conveniently accomplished by altering the amino acid sequence such that it contains one or more tri-peptide sequences selected from asparagine-X-serine and asparagine-X-threonine (where X is any amino acid except proline). O-linked glycosylation sites may be introduced by the addition of or substitution by, one or more serine or threonine residues to the starting sequence.

Another means of glycosylation of TCRs is by chemical or enzymatic coupling of glycosides to the protein. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine.

Similarly, deglycosylation (i.e., removal of carbohydrate moieties present on the binding molecule) may be accomplished chemically, e.g. by exposing the TCRs to trifluoromethanesulfonic acid, or enzymatically by employing endo- and exo-glycosidases.

Drug Conjugates

It is also conceivable to add a drug such as a small molecule compound to the TCRs, in particular soluble TCRs, of the invention. Linkage can be achieved via covalent bonds, or non-covalent interactions such as through electrostatic forces. Various linkers, known in the art, can be employed in order to form the drug conjugates.

Tags

The TCRs, in particular soluble TCRs, of the invention can be modified to introduce additional domains which aid in identification, tracking, purification and/or isolation of the respective molecule (tags). Non-limiting examples of such tags comprise peptide motives known as Myc-tag, HAT-tag, HA-tag, TAP-tag, GST-tag, chitin binding domain (CBD-tag), maltose binding protein (MBP-tag), Flag-tag, Strep-tag and variants thereof (e.g. Strep II-tag), His-tag, CD20, Her2/neu tags, myc-tag, FLAG-tag, T7-tag, HA(hemagglutinin)-tag, or GFP-tags.

Epitope tags are useful examples of tags that can be incorporated into the TCR of the invention. Epitope tags are short stretches of amino acids that allow for binding of a specific antibody and therefore enable identification and tracking of the binding and movement of soluble TCRs or host cells within the patient's body or cultivated (host) cells. Detection of the epitope tag, and hence, the tagged TCR, can be achieved using a number of different techniques. Examples of such techniques include: immunohistochemistry, immunoprecipitation, flow cytometry, immunofluorescence microscopy, ELISA, immunoblotting ("Western"), and affinity chromatography. The epitope tags can for instance have a length of 6 to 15 amino acids, in particular 9 to 11 amino acids. It is also possible to include more than one epitope tag in the TCR of the invention.

Tags can further be employed for stimulation and expansion of host cells carrying an inventive TCR by cultivating the cells in the presence of binding molecules (antibodies) specific for said tag. Nucleic acid The present invention further provides nucleic acids encoding the TCRs described herein. Specifically, polynucleotides encoding TCR alpha or beta chains, TCR alpha or beta chain variable regions, and TCR CDR3alpha and CDR3beta, as well as TCR variants, constructs and fragments of the invention are provided herein.

The term "polynucleotide" or "nucleic acid" as used herein comprises a sequence of polyribonucleotides and polydeoxyribonucleotides, e.g. modified or unmodified RNA or DNA, each in single-stranded and/or double-stranded form linear or circular, or mixtures thereof, including hybrid molecules. The nucleic acids according to this invention thus comprise DNA (such as dsDNA, ssDNA, cDNA), RNA (such as dsRNA, ssRNA, mRNA, ivtRNA), combinations thereof or derivatives (such as PNA) thereof.

A polynucleotide may comprise a conventional phosphodiester bond or a non-conventional bond (e.g., an amide bond, such as found in peptide nucleic acids (PNA)). The polynucleotides of the invention may also contain one or more modified bases, such as, for example, tritylated bases and unusual bases such as inosine. Other modifications, including chemical, enzymatic, or metabolic modifications, are also conceivable, as long as a binding molecule of the invention can be expressed from the polynucleotide. The polynucleotide may be provided in isolated form as defined elsewhere herein. A polynucleotide may include regulatory sequences such as transcription control elements (including promoters, enhancers, operators, repressors, and transcription termination signals), ribosome binding site, introns, or the like.

In particular, the present invention provides a polynucleotide comprising or consisting of a nucleic acid that is at least about 80%, about 85%, about 90%, about 91%, about 92%, about 93%, about 94%, about 95%, about 96%, about 97%, about 98%, about 99%, or 100% identical to a reference polynucleotide sequence selected from the group consisting of SEQ ID NOs: 23, 24, 25, 26, 27, 28, 29, or 30.

The polynucleotides described above may or may not comprise additional or altered nucleotide sequences encoding e.g., altered amino acid residues, a signal peptide to direct secretion of the encoded TCR, constant regions or other heterologous polypeptides as described herein. Such polynucleotides may thus encode fusion polypeptides, fragments, variants and other derivatives of the binding molecules described herein.

Also, the present invention includes compositions comprising one or more of the polynucleotides described above. Also provided herein are compositions, comprising a first polynucleotide and second polynucleotide wherein said first polynucleotide encodes a TCR alpha chain variable region as described herein and wherein said second polynucleotide encodes a TCR beta chain variable region as described herein.

The nucleic acid sequences of the present invention may be codon-optimized for optimal expression in the desired host cell, e.g. a human lymphocyte; or for expression in bacterial, yeast or insect cells that are particularly envisaged for the expression of soluble TCRs of the invention. Codon-optimization refers to the exchange in a sequence of interest of codons that are generally rare in highly expressed genes of a given species by codons that are generally frequent in highly expressed genes of such species, such codons encoding the same amino acids as the codons that are being exchanged. Selection of optimum codons thus depends on codon usage of the host genome and the presence of several desirable and undesirable sequence motifs.

Vector

Further provided herein is a vector, comprising one or more of the polynucleotides as described herein. A "vector" is a nucleic acid molecule used as a vehicle to transfer (foreign) genetic material into a host cell where it can for instance be replicated and/or expressed.

The term "vector" encompasses, without limitation plasmids, viral vectors (including retroviral vectors, lentiviral vectors, adenoviral vectors, vaccinia virus vectors, polyoma virus vectors, and adenovirus-associated vectors (AAV)), phages, phagemids, cosmids and artificial chromosomes (including BACs and YACs). The vector itself is generally a nucleotide sequence, commonly a DNA sequence that comprises an insert (transgene) and a larger sequence that serves as the "backbone" of the vector. Engineered vectors typically comprise an origin for autonomous replication in the host cells (if stable expression of the polynucleotide is desired), selection markers, and restriction enzyme cleavage sites (e.g. a multiple cloning site, MCS). Vector may additionally comprise promoters, genetic markers, reporter genes, targeting sequences, and/or protein purification tags. As known to those skilled in the art, large numbers of suitable vectors are known to those of skill in the art and many are commercially available. Examples of suitable vectors are provided in J. Sambrook et al., Molecular Cloning: A Laboratory Manual (4th edition), Cold Spring Harbor Laboratory, Cold Spring Harbor Laboratory Press, New York (2012) and include Targeting Vectors Targeting vectors can be used to integrate a polynucleotide into the host cell's chromosome by methods known in the art, such as described by J. Sambrook et al., Molecular Cloning: A Laboratory Manual (4th edition), Cold Spring Harbor Laboratory, Cold Spring Harbor Laboratory Press, New York (2012). Briefly, suitable means include homologous recombination or use of a hybrid recombinase that specifically targets sequences at the integration sites. Targeting vectors are typically circular and linearized before used for homologous recombination. As an alternative, the foreign polynucleotides may be DNA fragments joined by fusion PCR or synthetically constructed DNA fragments which are then recombined into the host cell. It is also possible to use heterologous recombination which results in random or non-targeted integration.

The present invention also provides a vector comprising the nucleic acid described herein.

Expression Vectors

The vector of the present invention can also be an expression vector. "Expression vectors" or "expression constructs" can be used for the transcription of heterologous polynucleotide sequences, for instance those encoding the TCRs of the invention, and translation of their mRNA in a suitable host cell. This process is also referred to as "expression" of the TCRs of the invention herein.

Besides an origin of replication, selection markers, and restriction enzyme cleavage sites, expression vectors typically include one or more regulatory sequences operably linked to the heterologous polynucleotide to be expressed.

The term "regulatory sequence" refers to a nucleic acid sequence necessary for the expression of an operably linked coding sequence of a (heterologous) polynucleotide in a particular host organism or host cell and thus include transcriptional and translational regulatory sequences. Typically, regulatory sequences required for expression of heterologous polynucleotide sequences in prokaryotes include a promoter(s), optionally operator sequence(s), and ribosome binding site(s). In eukaryotes, promoters, polyadenylation signals, enhancers and optionally splice signals are typically required. Moreover, specific initiation and secretory signals also may be introduced into the vector in order to allow for secretion of the polypeptide of interest into the culture medium.

A nucleic acid is "operably linked" when it is placed into a functional relationship with another nucleic acid sequence, in particular on the same polynucleotide molecule. For example, a promoter is operably linked with a coding sequence of a heterologous gene when it is capable of effecting the expression of that coding sequence. The promoter is typically placed upstream of the gene encoding the polypeptide of interest and regulates the expression of said gene.

Exemplary regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. As set out before, the expression vectors may also include origins of replication and selectable markers.

As mentioned previously, vectors of the invention may further comprise one or more selection markers. Suitable selection markers for use with eukaryotic host cells include, without limitation, the herpes simplex virus thymidine kinase (tk), hypoxanthine-guanine phosphoribosyltransferase (hgprt), and adenine phosphoribosyltransferase (aprt) genes. Other genes include dhfr (methotrexate resistance), gpt (mycophenolic acid resistance) neo (G-418 resistance) and hygro (hygromycin resistance). Vector amplification can be used to increase expression levels. In general, the selection marker gene can either be directly linked to the polynucleotide sequences to be expressed, or introduced into the same host cell by co-transformation.

In view of the above, the present invention thus further provides one or more of the nucleotide sequences described herein inserted into (i.e. comprised by) a vector. Specifically, the invention provides (replicable) vectors comprising a nucleotide sequence encoding a TCR of the invention, or an alpha or beta chain thereof, or an alpha or beta variable domain, or a CDR3 alpha or CDR3beta operably linked to a promoter.

The skilled person will readily be able to select a suitable expression vector based on, e.g., the host cell intended for TCR expression. Examples for suitable expression vectors are viral vectors, such as retroviral vectors e.g. MP71 vectors or retroviral SIN vectors; and lentiviral vectors or lentiviral SIN vectors. Viral vectors comprising polynucleotides encoding the TCRs of the invention are for instance capable of infecting lymphocytes, which are envisaged to subsequently express the heterologous TCR. Another example for a suitable expression vector is the Sleeping Beauty (SB) transposon transposase DNA plasmid system, SB DNA plasmid. The nucleic acids and/or in particular expression constructs of the invention can also be transferred into cells by transient RNA transfection.

Currently used viral vectors for native TCR expression typically link the TCR-alpha and TCR-beta chain genes in one vector with either an internal ribosomal entry site (IRES) sequence or the 2A peptide sequence derived from a porcine tschovirus, resulting in the expression a single messenger RNA (mRNA) molecule under the control of the viral promoter within the transduced cell.

Host Cell

The present invention further provides a host cell comprising the TCR, nucleic acid or the vector described herein.

A variety of host cells can be used in accordance with the invention. As used herein, the term "host cell" encompasses cells which can be or has/have been recipients of polynucleotides or vectors described herein and/or express (and optionally secreting) the TCR of the present invention. The terms "cell" and "cell culture" are used interchangeably to denote the source of a TCR unless it is clearly specified otherwise. The term "host cell" also includes "host cell lines".

In general, the term "host cell" includes prokaryotic or eukaryotic cells, and also includes without limitation bacteria, yeast cells, fungi cells, plant cells, and animal cells such as insect cells and mammalian cells, e.g., murine, rat, macaque or human cells.

In view of the above, the invention thus provides, inter alia, host cells comprising a polynucleotide or a vector, e.g. an expression vector comprising a nucleotide sequence encoding a TCR or TCR construct as described herein.

Polynucleotides and/or vectors of the invention can be introduced into the host cells using routine methods known in the art, e.g. by transfection, transformation, or the like.

"Transfection" is the process of deliberately introducing nucleic acid molecules or polynucleotides (including vectors) into target cells. An example is RNA transfection, i.e. the process of introducing RNA (such as in vitro transcribed RNA, ivtRNA) into a host cell. The term is mostly used for non-viral methods in eukaryotic cells. The term "transduction" is often used to describe virus-mediated transfer of nucleic acid molecules or polynucleotides. Transfection of animal cells typically involves opening transient pores or "holes" in the cell membrane, to allow the uptake of material. Transfection can be carried out using calcium phosphate, by electroporation, by cell squeezing or by mixing a cationic lipid with the material to produce liposomes, which fuse with the cell membrane and deposit their cargo inside. Exemplary techniques for transfecting eukaryotic host cells include lipid vesicle mediated uptake, heat shock mediated uptake, calcium phosphate mediated transfection (calcium phosphate/DNA co-precipitation), microinjection and electroporation.

The term "transformation" is used to describe non-viral transfer of nucleic acid molecules or polynucleotides (including vectors) into bacteria, and also into non-animal eukaryotic cells, including plant cells. Transformation is hence the genetic alteration of a bacterial or non-animal eukaryotic cell resulting from the direct uptake through the cell membrane(s) from its surroundings and subsequent incorporation of exogenous genetic material (nucleic acid molecules). Transformation can be effected by artificial means. For transformation to happen, cells or bacteria must be in a state of competence, which might occur as a time-limited response to environmental conditions such as starvation and cell density. For prokaryotic transformation, techniques can include heat shock mediated uptake, bacterial protoplast fusion with intact cells, microinjection and electroporation. Techniques for plant transformation include Agrobacterium mediated transfer, such as by *A. tumefaciens*, rapidly propelled tungsten or gold microprojectiles, electroporation, microinjection and polyethylene glycol mediated uptake.

In view of the above, the present invention thus further provides host cells comprising at least one polynucleotide sequence and/or vector as described herein.

For expression of the TCRs of the invention, a host cell may be chosen that modulates the expression of the inserted polynucleotide sequences, and/or modifies and processes the gene product (i.e. RNA and/or protein) as desired. Such modifications (e.g., glycosylation) and processing (e.g., cleavage) of gene products may be important for the function of the TCR. Different host cells have characteristic and specific mechanisms for the post-translational processing and modification of gene products. Appropriate cell lines or host systems can be chosen to ensure the correct modification and processing of the product. To this end, eukaryotic host cells that possess the cellular machinery for proper processing of the primary transcript, glycosylation, and phosphorylation of the gene product may be used.

It is envisaged herein to provide (a) host cells for expressing and obtaining TCRs of the invention, in particular in soluble form ("production host cells") and (b) host cells expressing a TCR of the invention and having effector function ("effector host cells"). Such "effector host cells" are particularly useful for therapeutic applications and are envisaged for administration to a subject in need thereof. Preferred "effector host cells" include lymphocytes such as cytotoxic T lymphocytes (CTLs), CD8+ T cells, CD4+ T cells, natural killer (NK) cells, natural killer T (NKT) cells, gamma/delta-T-cells.

"Production Host Cell"

Cells

"Production host cells" used for the expression of soluble TCRs of the invention are preferably capable of expressing high amounts of recombinant protein.

Exemplary mammalian host cells that can be used for as "production host cells" include Chinese Hamster Ovary (CHO cells) including DHFR minus CHO cells such as DG44 and DUXBI 1, NSO, COS (a derivative of CVI with SV40 T antigen), HEK293 (human kidney), and SP2 (mouse myeloma) cells. Other exemplary host cell lines include, but are not limited to, HELA (human cervical carcinoma), CVI (monkey kidney line), VERY, BHK (baby hamster kidney), MDCK, 293, W138, R1610 (Chinese hamster fibroblast) BALBC/3T3 (mouse fibroblast), HAK (hamster kidney line), P3×63–Ag3.653 (mouse myeloma), BFA-IcIBPT (bovine endothelial cells), and RAJI (human lymphocyte). Host cell lines are typically available from commercial services, the American Tissue Culture Collection (ATCC) or from published literature.

Non-mammalian cells such as bacterial, yeast, insect or plant cells are also readily available and can also be used as "production host cells" as described above. Exemplary bacterial host cells include enterobacteriaceae, such *Escherichia coli, Salmonella*; Bacillaceae, such as *Bacillus subtilis*; Pneumococcus; *Streptococcus*, and *Haemophilus* influenza. Other host cells include yeast cells, such as *Saccharomyces cerevisiae*, and *Pichia pastoris*. Insect cells include, without limitation, *Spodoptera frugiperda* cells.

In accordance with the foregoing, conceivable expressions systems (i.e. host cells comprising an expression vector as described above) include microorganisms such as bacteria (e.g., *E. coli, B. subtilis*) transformed with recombinant bacteriophage DNA, plasmid DNA or cosmid DNA expression vectors; yeast (e.g., *Saccharomyces, Pichia*) transformed with recombinant yeast expression vectors; insect cell systems infected with recombinant virus expression vectors (e.g., baculovirus); plant cell systems infected with recombinant virus expression vectors (e.g., cauliflower mosaic virus, CaMV; tobacco mosaic virus, TMV) or transformed with recombinant plasmid expression vectors (e.g., Ti plasmid). Mammalian expression systems harboring recombinant expression constructs containing promoters derived from the genome of mammalian cells (e.g., metallothionein promoter) or from mammalian viruses (e.g., the adenovirus late promoter; the vaccinia virus 7.5K promoter, the cytomegalovirus (CMV) major immediate-early promoter (MIEP) promoter) are often preferred. Suitable mammalian host cells can be selected from known cell lines (e.g., COS, CHO, BLK, 293, 3T3 cells), however it is also conceivable to use lymphocytes such as cytotoxic T lymphocytes (CTLs), CD8+ T cells, CD4+ T cells, natural killer (NK) cells, natural killer T (NKT) cells, gamma/delta-T-cells.

In accordance with the foregoing, the present invention also provides a method for producing and obtaining a TCR as described herein comprising the steps of (i) incubating a host cell (i.e., a production host cell) under conditions causing expression of said TCR and (ii) purifying said TCR.

Cultivation

The host cells harboring the expression vector are grown under conditions appropriate to the production of the TCRs provided herein, in particular alpha chains and/or beta chains as described elsewhere herein, and assayed for alpha and/or beta chain protein synthesis. For the expression of double-chained TCRs, vectors encoding both the alpha and beta chains may be co-expressed in the host cell for expression of the entire molecule.

Purification

Once a TCR of the invention has been expressed, it may be purified by any purification method known in the art, for example, by chromatography (e.g., ion exchange chromatography (e.g. hydroxylapatite chromatography), affinity chromatography, particularly Protein A, Protein G or lectin affinity chromatography, sizing column chromatography), centrifugation, differential solubility, hydrophobic interaction chromatography, or by any other standard technique for the purification of proteins. The skilled person will readily be able to select a suitable purification method based on the individual characteristics of the TCR to be recovered.

"Effector Host Cell"

As mentioned earlier, the present invention also provides for "effector host cells" comprising a nucleotide sequence, vector or TCR of the invention. Said effector host cells are modified using routine methods to comprise a nucleic acid sequence encoding the TCR of the invention, and are envisaged to express the TCR described herein, in particular on the cell surface. For the purposes of the present invention, "modified host cells expressing a TCR of the invention" generally refers to (effector or production) host cells treated or altered to express a TCR according to the present invention, for instance by RNA transfection as described in the appended Examples. Other methods of modification or transfection or transduction, such as those described elsewhere herein, are also envisaged. The term "modified host cell" thus includes "transfected", "transduced" and "genetically engineered" host cells preferably expressing the TCR of the present invention.

Preferably, such "(modified) effector host cells" (in particular "(modified) effector lymphocytes") are capable of mediating effector functions through intracellular signal transduction upon binding of the TCR to its specific antigenic target. Such effector functions include for instance the release of perforin (which creates holes in the target cell membrane), granzymes (which are proteases that act intracellularly to trigger apoptosis), the expression of Fas ligand (which activates apoptosis in a Fas-bearing target cell) and the release of cytokines, preferably Th1/Tc1 cytokines such as IFN-γ, IL-2 and TNF-α. Thus, an effector host cell engineered to express the TCR of the invention that is capable recognizing and binding to its antigenic target in the subject to be treated is envisaged to carry out the abovementioned effector functions, thereby killing the target (e.g. cancer) cells. Cytolysis of target cells can be assessed e.g. with the CTL fluorescent killing assay (CTL, USA) detecting the disappearance of fluorescently labeled target cells during co-culture with TCR-transfected recipient T cells.

In view of the above, effector host cells preferably express a functional TCR, i.e. that typically comprises a TCR alpha and beta chain described herein; and also the signal transducing subunits CD3 gamma, delta, epsilon and zeta (CD3 complex). Moreover, expression of co-receptors CD4 or CD8 may also be desired. Generally, lymphocytes harboring the required genes involved in antigen binding, receptor activation and downstream signalling (e.g. Lck, FYN, CD45, and/or Zap70), T cells are particularly suitable as effector host cells. However, effector host cells expressing the TCR of the invention as a "binding domain" without the CD3 signal transducing subunit and/or aforementioned downstream signalling molecules (i.e. being capable of recognizing the antigenic target described herein, but without effecting functions mediated by CD3 and/or the aforementioned downstream signalling molecules) are also envisaged herein. Such effector cells are envisaged to be capable of recognizing the antigenic target described herein, and optionally of effecting other functions not associated with CD3 signalling and/or signalling of the aforementioned downstream signalling molecules. Examples include NK or NKT cells expressing the inventive TCR and being capable of e.g. releasing cytotoxic granules upon recognition of their antigenic target.

Thus, cytotoxic T lymphocytes (CTLs), CD8+ T cells, CD4+ T cells, natural killer (NK) cells, natural killer T (NKT) cells, gamma/delta-T-cells are considered useful lymphocyte effector host cells. Such lymphocytes expressing the recombinant TCR of the invention are also referred to as "modified effector lymphocytes" herein. The skilled person will however readily acknowledge that in general any component of the TCR signalling pathway leading to the desired effector function can be introduced into a suitable host cell by recombinant genetic engineering methods known in the art.

Effector host cells in particular lymphocytes such as T cells can be autologous host cells that are obtained from the subject to be treated and transformed or transduced to express the TCR of the invention. Typically, recombinant expression of the TCR will be accomplished by using a viral vector as described in the appended Examples. Techniques for obtaining and isolating the cells from the patient are known in the art.

As mentioned earlier, the effector host cells provided herein are particularly envisaged for therapeutic applications. Further genetic modifications of the host cells may be desirable in order to increase therapeutic efficacy. E.g., when using autologous CD8+ T cells as "effector host cells" suitable additional modifications include downregulation of the endogenous TCR, CTLA-4 and/or PD-1 expression; and/or amplification of co-stimulatory molecules such as CD28, CD134, CD137. Means and methods for achieving the aforementioned genetic modifications have been described in the art.

Methods for targeted genome engineering of host cells are known in the art and include, besides gene knockdown with siRNA, the use of so-called "programmable nucleases" such as zinc-finger nucleases (ZFNs), transcription activator-like effector nucleases (TALENs) and RNA-guided engineered nucleases (RGENs) derived from the bacterial clustered regularly interspaced short palindromic repeat (CRISPR)-Cas (CRISPR-associated) system, as inter alia reviewed in Kim & Kim Nature Reviews Genetics 15, 321-334 (2014). For instance, programmable nucleases such as TALENs can be employed to cut the DNA regions that code for "unwanted" proteins, such as PD-1, CTLA-4 or an endogenous TCR, and thereby reducing their expression. When T cells are used as (effector) host cells, downregulation of the endogenous TCR has the benefit of reducing unwanted "mispairing" of endogenous and exogenous TCR alpha/beta chains.

Pharmaceutical Composition/Diagnostic

The present invention further provides a pharmaceutical composition as one or more active agents, the TCR, the nucleic acid, the vector and/or the host cell as described herein, and, optionally, one or more pharmaceutically excipient(s). Accordingly, the use of said TCR, nucleic acid, vector and host cell for the manufacture of a pharmaceutical composition or medicament is also envisaged herein.

The term "pharmaceutical composition" particularly refers to a composition suitable for administering to a human. However, compositions suitable for administration to non-human animals are generally also encompassed by the term.

The pharmaceutical composition and its components (i.e. active agents and optionally excipients) are preferably pharmaceutically acceptable, i.e. capable of eliciting the desired therapeutic effect without causing any undesirable local or systemic effects in the recipient. Pharmaceutically acceptable compositions of the invention may for instance be sterile. Specifically, the term "pharmaceutically acceptable" may mean approved by a regulatory agency or other generally recognized pharmacopoeia for use in animals, and more particularly in humans.

The active agent described in the foregoing (for instance the host cell or the TCR) is preferably present in the pharmaceutical composition in a therapeutically effective amount. By "therapeutically effective amount" is meant an amount of the active agent that elicits the desired therapeutic effect. Therapeutic efficacy and toxicity can be determined by standard procedures, e.g. in cell culture or in test animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $ED_{50}/LD_{50}$. Pharmaceutical compositions that exhibit large therapeutic indices are preferred.

Dosage

The exact dosage of the TCR polynucleotide, vector or host cell will be ascertainable by one skilled in the art using known techniques. Suitable dosages provide sufficient amounts of the active agent of the invention and are preferably therapeutically effective, i.e. elicit the desired therapeutic effect.

As is known in the art, adjustments for purpose of the treatment (e.g. remission maintenance vs. acute flare of disease), route, time and frequency of administration, time and frequency of administration formulation, age, body weight, general health, sex, diet, severity of the disease state, drug combination(s), reaction sensitivities, and tolerance/response to therapy may be necessary. Suitable dosage ranges, for instance for soluble TCRs as described herein, can be determined using data obtained from cell culture assays and animal studies and may include the $ED_{50}$. Typically, dosage amounts may vary from 0.1 to 100000 micrograms, up to a total dose of about 2 g, depending upon the route of administration. Exemplary dosages of the active agent of the invention are in the range from about 0.01 mg/kg to about 10 mg/kg, from about 0.1 mg/kg to about 10 mg/kg, from about 1 mg/kg to about 10 mg/kg, from about 1 mg/kg to about 5 mg/kg, from about 0.01 mg/kg to about 1 mg/kg, or from about 0.1 mg/kg to about 1 mg/kg. Guidance as to particular dosages and methods of delivery is provided in the literature. It is recognized that treatment may require a single administration of a therapeutically effective dose or multiple administrations of a therapeutically effective dose of the active agent of the invention. E.g., some pharmaceutical compositions might be administered every 3 to 4 days, every week, or once every two weeks, or once within a month depending on formulation, half-life and clearance rate of the particular composition.

As set out previously, the pharmaceutical composition may optionally comprise one or more excipients and/or additional active agents.

Excipients

The term "excipient" includes fillers, binders, disintegrants, coatings, sorbents, antiadherents, glidants, preservatives, antioxidants, flavoring, coloring, sweeting agents, solvents, co-solvents, buffering agents, chelating agents, viscosity imparting agents, surface active agents, diluents, humectants, carriers, diluents, preservatives, emulsifiers, stabilizers and tonicity modifiers. It is within the knowledge of the skilled person to select suitable excipients for preparing the desired pharmaceutical composition of the invention. Exemplary carriers for use in the pharmaceutical composition of the invention include saline, buffered saline, dextrose, and water. Typically, choice of suitable excipients will inter alia depend on the active agent used, the disease to be treated, and the desired formulation of the pharmaceutical composition.

Additional Active Agents

The present invention further provides pharmaceutical compositions comprising one or more of the inventive active agents specified above (for instance a host cell or a TCR construct), and one or more additional active agents that are suitable for treatment and/or prophylaxis of the disease to be treated. Preferred examples of active ingredients suitable for combinations include known anti-cancer drugs such as cisplatin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin; and peptide cytotoxins such as ricin, diphtheria toxin, *pseudomonas* bacterial exotoxin A, DNAase and RNAase; radio-nuclides such as iodine 131, rhenium 186, indium 111, yttrium 90, bismuth 210 and 213, actinium 225 and astatine 213; prodrugs, such as antibody directed enzyme pro-drugs; immuno-stimulants, such as IL-2, chemokines such as IL-8, platelet factor 4, melanoma growth stimulatory protein, etc., antibodies or fragments thereof such as anti-CD3 antibodies or fragments thereof, complement activators, xenogeneic protein domains, allogeneic protein domains, viral/bacterial protein domains and viral/bacterial peptides.

Administration

A variety of routes are applicable for administration of the pharmaceutical composition according to the present invention. Typically, administration will be accomplished parentally. Methods of parenteral delivery include topical, intra-arterial, intramuscular, subcutaneous, intramedullary, intrathecal, intraventricular, intravenous, intraperitoneal, intrauterine, intravaginal, sublingual or intranasal administration.

Formulation

The pharmaceutical compositions of the invention can be formulated in various forms, depending inter alia on the active agent used (e.g., soluble TCR), e.g. in solid, liquid, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts or in a form which is particularly suitable for the desired method of administration. Processes known per se for producing medicaments are indicated in 22nd edition of Remington's Pharmaceutical Sciences (Ed. Maack Publishing Co, Easton, Pa., 2012) and may include, for instance conventional mixing, dissolving, granulating, dragee-making, levigating, emulsifying, encapsulating, entrapping or lyophilizing processes. Pharmaceutical compositions comprising, for instance, host cells or soluble TCR as described herein will typically be provided in a liquid form, and preferably comprise a pharmaceutically acceptable buffer.

After pharmaceutical compositions of the invention have been prepared they can be placed in an appropriate container and labeled for treatment of an indicated condition. Such labeling would for instance include amount, frequency and method of administration.

Treatment

In view of the foregoing the present invention thus provides a TCR, nucleic acid, vector and/or host cell as described herein for use as a medicament.

The TCR, nucleic acid, vector and/or host cell can in general be employed for treatment detection, diagnosis, prognosis, prevention and/or treatment of diseases or disorders. The term "treatment" in all its grammatical forms includes therapeutic or prophylactic treatment of a subject in need thereof. A "therapeutic or prophylactic treatment" comprises prophylactic treatments aimed at the complete prevention of clinical and/or pathological manifestations or therapeutic treatment aimed at amelioration or remission of clinical and/or pathological manifestations. The term "treatment" thus also includes the amelioration or prevention of diseases.

The terms "subject" or "individual" or "animal" or "patient" are used interchangeably herein to refer to any subject, particularly a mammalian subject, for whom therapy is desired. Mammalian subjects generally include humans, non-human primates, dogs, cats, guinea pigs, rabbits, rats, mice, horses, cattle, cows, and the like. However, it will readily be understood that the TCRs, nucleic acids, vectors, host cells and pharmaceutical compositions provided herein are especially envisaged for treatment of human subjects, in particular those that are HLA-A2-positive.

Direct Administration

For therapy, TCRs—in particular soluble TCRs of the invention-, nucleic acids, vectors (such as viral vectors) or host cells of the invention can be administered directly to the subject in need thereof. Thus the present invention provides a TCRs, nucleic acid, vector or host cells for use in a method of detecting, diagnosing, prognosing, preventing and/or treating of cancer. Said method can comprise the steps of (a) providing one or more of (i) a TCR (ii), a nucleic acid, (iii) a vector, (iv) a host cell, and/or (v) a pharmaceutical composition of the present invention; and (b) administering one or more of (i)-(v) to the subject in need thereof. Optionally, the method can comprise a further step of cancer therapy, e.g. radiation, or administration of one or more anti-cancer agents.

Ex Vivo Treatment

Treatment according to the invention may also comprise the steps of (a) providing a sample of a subject, said sample comprising lymphocytes; (b) providing one or more of the TCR, nucleic acid, vector host cell and/or pharmaceutical composition of the invention (c) introducing of one or more of (i) to (v) of step (b) into the lymphocytes of step (a) and, thereby, obtaining modified lymphocytes, (d) administering the modified lymphocytes of step (c) to a subject or patient in need thereof.

The lymphocytes provided in step (a) are particularly envisaged to be "effector host cells" as described in the foregoing and are advantageously selected from T cells, NK cells and/or NKT cells, especially CD8+ T cells; and can be obtained in a previous step (a') from a sample—in particular a blood sample—of the subject by routine methods known in the art. It is however also conceivable to use other lymphocytes that are preferably capable of expressing the TCR of the present invention and exert the desired biological effector functions as described herein. Moreover, said lymphocytes will typically be selected for compatibility with the subject's immune system, i.e. they will preferably not elicit an immunogenic response. For instance, it is conceivable to use a "Universal Recipient Cells", i.e. universally compatible lymphocytes exerting the desired biological effector functions that can be grown and expanded in vitro. Use of such cells will thus obviate the need for obtaining and providing the subject's own lymphocytes in step (a).

The ex vivo introduction of step (c) can be carried out by introducing a nucleic acid or vector described herein via electroporation into the lymphocytes, or by infecting the lymphocytes with a viral vector, such as a lentiviral or retroviral vector as described previously in the context of the effector host cell. Other conceivable methods include the use of by transfection reagents, such as liposomes, or transient RNA transfection. The transfer of antigen-specific TCR genes into (primary) T cells by e.g. (retro-)viral vectors or transient RNA transfection represents a promising tool for generating tumor-associated antigen-specific T cells that can subsequently be re-introduced into the donor, where they specifically target and destroy tumor cells expressing said antigen. In the present invention, said tumor-associated antigen is $PRAME_{100-108}$, particularly in its HLA-A*02 bound form.

In view of the above, a further aspect of the present invention is thus the use of a TCR, a nucleic acid sequence, a vector and/or a host cell as described elsewhere herein for generating modified lymphocytes. Means and methods for introducing, e.g. a nucleic acid and a vector into the lymphocytes have been described elsewhere herein.

Diagnostic Composition

The present invention also provides a diagnostic composition comprising, as one or more diagnostic agent(s), the TCR, nucleic acid, the vector and/or the host cell as described herein. Typically, said diagnostic agent will comprise means for detecting its binding to its antigenic target, for instance a label as described in the context of the TCR constructs of the invention. As regards the host cell, it is for instance conceivable to use modified host cells comprising a dye or a contrast agent that is released (instead of cytotoxic granules) upon antigen recognition.

Use

The present invention envisages use of the diagnostic agents described in the foregoing for detecting, diagnosing and/or prognosing cancer in a subject which can be accomplished in vivo or in vitro.

Thus the invention provides a diagnostic composition for use in detecting, diagnosing and/or pronging cancer in a subject in vivo, said composition comprising, as a diagnostic agent, the TCR, the nucleic acid, the vector and/or the host cell of the invention. The method will typically comprise (a) administering said diagnostic agent to the subject and (b) detecting binding of said diagnostic agent to its antigenic target.

Moreover, the invention provides a method of detecting, diagnosing and/or prognosing cancer in a subject in vitro. In accordance the present invention also provides a method of detecting the presence of a cancer in a subject, comprising the steps of (a) providing a sample of a subject, said sample comprising one or more cells; (b) contacting said sample with the TCR, nucleic acid, vector and/or host cell of the invention; thereby forming a complex, and (c) detecting the complex. Said complex is envisaged to be indicative for binding of the diagnostic agent to its antigenic target and is of the presence of a (cancer) cell expressing said antigenic target.

In both methods binding of the diagnostic agent to its antigenic target is detectable by using routine methods known in the art and will inter alia depend on the specific diagnostic agent used. Suitable labels that can be coupled to the diagnostic agent of the invention are exemplified in the section relating to labeled TCR constructs. Use for generating modified lymphocytes It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., "about 20" includes 20.

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

A better understanding of the present invention and of its advantages will be obtained from the following example, offered for illustrative purposes only. The example is not intended to limit the scope of the present invention in any way.

The invention is also characterized by the following items:

1. A T-cell receptor (TCR) comprising:
   (i) a CDR3 of the TCR alpha chain variable region comprising or consisting of the amino acid sequence of CAVHSTAQAGTALIF (SEQ ID NO: 1) or an amino acid sequence having at least 80% identity to SEQ ID NO 1: more preferably at least 85% identity, more preferably 90% or 95% and/or
   (ii) a CDR3 of the TCR beta chain variable region comprising or consisting of the amino acid sequence of CASSTHRGQTNYGYTF (SEQ ID NO. 2) or an amino acid sequence having at least 80% identity to SEQ ID NO: 2, more preferably at least 85% identity, more preferably 90% or 95% identity.
2. The TCR according to item 1, said TCR being capable of binding to the epitope comprised within the amino acid sequence of X1LX2GLDX3LL (SEQ ID NO:31) or its MHC-bound form, preferably to the epitope comprised within the amino acid sequence of VLDGLDVLL (SEQ ID NO:32) or its MHC-bound form.
3. The TCR according to any one of items 1 or 2, comprising
   (i) a TCR alpha chain variable region comprising or consisting of the amino acid sequence depicted in SEQ ID NO: 15, and/or
   (ii) a TCR beta chain variable region comprising or consisting of the amino acid sequence depicted in SEQ ID NO: 16.
4. The TCR according to any one of the preceding items, further comprising
   (i) a TCR alpha chain constant region and/or
   (ii) a TCR beta chain constant region
5. The TCR according to any one of the preceding items, comprising
   (i) a TCR alpha chain comprising or consisting of an amino acid sequence selected from SEQ ID NO: 7; SEQ ID NO: 9, SEQ ID NO: 11, or SEQ ID NO: 13, or an amino acid sequence having at least 80% identity, more preferably at least 85% identity, more preferably 90% or 95% to SEQ ID NO: 7, 11, 9 or 13; and/or
   (ii) a TCR beta-chain comprising or consisting of an amino acid sequence selected from of SEQ ID NO: 8, SEQ ID NO: 10, SEQ ID NO: 12, or SEQ ID NO: 14 or an amino acid sequence having at least 80% identity, more preferably at least 85% identity, more preferably 90% or 95% to SEQ ID NO: 8, 10, 12 or 14.
6. The TCR according to any one of the preceding items, said TCR being selected from a native TCR, a TCR variant, a TCR fragment, or a TCR construct.
7. The TCR construct according to item 6, comprising at least one TCR alpha-chain(s) and at least one TCR beta-chain(s) covalently linked to each other to form TCR heterodimers or multimers.
8. The TCR according to any of the preceding items, further comprising one or more fusion component(s) optionally selected from Fc receptors; Fc domains, including IgA, IgD, IgG, IgE, and IgM; cytokines, including IL-2 or IL-15; toxins; antibodies or antigen-binding fragments thereof, including anti-CD3, anti-CD28, anti-CD5, anti-CD 16 or anti-CD56 antibodies or antigen-binding fragments thereof; CD247 (CD3-zeta), CD28, CD137, CD134 domain, or combinations thereof, optionally further comprising at least one linker.
9. The TCR according to any one of the preceding items, comprising
   (i) at least one TCR alpha-chain as defined in any one of items 1 to 4; and
   (ii) at least one TCR beta-chain as defined in any one of items 1 to 4
   (iii) an antibody or a single chain antibody fragment (scFv) which is directed against an antigen or epitope on the surface of lymphocytes, wherein the TCR alpha-chain(s) and TCR beta-chain(s) are linked to each other and fused, optionally via a linker, to said antibody or scFv.
10. The TCR according to item 9, wherein said antigen is selected from CD3, CD28, CD5, CD16 or CD56.
11. The TCR according to any one of the preceding items, further comprising at least one label.
12. The TCR according to any one of the preceding items which is soluble.
13. A nucleic acid encoding the TCR according to any one of the preceding items.
14. The nucleic acid according to item 13, comprising the nucleic acid sequence of SEQ ID NO: 23, 24, 25, 26, 27, 28, 29 or 30.
15. A vector comprising the nucleic acid according to any one of items 13 or 14.
16. A host cell comprising the TCR according to any one of items 1 to 12, the nucleic acid sequence according to item 12 or 13 or the vector according to item 14.
17. The host cell according to item 16 which is selected from lymphocytes including but not limited to cytotoxic T lymphocytes (CTLs), CD8+ T cells, CD4+ T cells, natural killer (NK) cells, natural killer T (NKT) cells, gamma/delta-T-cells.

18. A method for obtaining a TCR according to any one of items 1 to 12, comprising
    (i) incubating a host cell according to item 17 under conditions causing expression of said TCR
    (ii) purifying said TCR.
19. A pharmaceutical or diagnostic composition comprising one or more of:
    (i) the TCR according to any one of items 1 to 12;
    (ii) the nucleic acid according to any one of items 13 to 14
    (iii) the vector according to item 15; and/or
    (iv) the host cell according to any one of items 16 or 17,
    and, optionally, pharmaceutically excipient(s).
20. The TCR according to any one of items 1 to 12, the nucleic acid according to item 13 or 14, the vector according to item 15 and/or the host cell according to item 16 or 17 for use as a medicament.
21. The TCR according to any one of items 1 to 12, the nucleic acid according to item 13 or 14, the vector according to item 15 and/or the host cell according to item 16 or 17 for use as a medicament. for use in detection, diagnosis, prognosis, prevention and/or treatment of cancer.
22. The TCR, nucleic acid, vector and/or host cell for the use of item 21, wherein prevention and/or treatment of cancer comprises
    (a) providing or more of
        (i) the TCR according to any one of items 1 to 12;
        (ii) the nucleic acid according to any one of items 13 or 14
        (iii) the vector according to item 15; and/or
        (iv) the host cell according to any one of items 16 or 17,
        (v) the pharmaceutical composition according to item 19; and
    (b) administering at least one of (i) to (v) to a subject in need thereof.
23. The TCR, nucleic acid, vector and/or host cell for the use of item 21, wherein prevention and/or treatment of cancer comprises
    (a) providing a sample of a subject, said sample comprising lymphocytes;
    (b) providing one or more of
        (i) the TCR according to any one of items 1 to 12;
        (ii) the nucleic acid according to any one of items 13 or 14
        (iii) the vector according to item 15; and/or
        (iv) the host cell according to any one of items 16 or 17,
        (v) the pharmaceutical composition according to item 19;
    (c) introducing of one or more of (i) to (v) of step (b) into the lymphocytes of step (a) and, thereby, obtaining modified lymphocytes,
    (d) administering the modified lymphocytes of step (c) to a subject or patient in need thereof.
24. A method of detecting the presence of a cancer in a subject in vitro, comprising:
    (a) providing a sample of a subject, said sample comprising one or more cells;
    (b) contacting said sample with
        (i) the TCR according to any one of items 1 to 12;
        (ii) the nucleic acid according to any one of items 13 or 14
        (iii) the vector according to item 15; and/or
        (iv) the host cell according to any one of items 16 or 17,
        (v) the pharmaceutical composition according to item 19;
    thereby forming a complex, and
    (c) detecting the complex,
    wherein detection of the complex is indicative of the presence of the cancer in the subject.
25. Use of a TCR according to any one of items 1 to 12, a nucleic acid according to item 13 or 14 and/or a vector according to item 15 for generating modified lymphocytes.

EXAMPLES

| Abbreviations and Synonyms | |
|---|---|
| (m)DC | (mature) dendritic cell |
| ivtRNA | In vitro transcribed RNA |
| APC | antigen-presenting cell |
| $(X^{pos})$ or $(X)^+$ | expressing X |
| VLD or VLD peptide | $PRAME_{100\text{-}108}$ |
| E:T ratio | Ratio of effector cells to target cells |
| SLL or SLL peptide | Peptide, irrelevant, SLLQHLIGL (SEQ ID NO: 229) |
| ALY or ALY peptide | Peptide, irrelevant, ALYVDSLFFL (SEQ ID NO: 230) |
| ELA or ELA peptide | Peptide, irrelevant, ELAGIGILTV (SEQ ID NO: 231) |
| [M] | Concentration molar [mol/L] |
| PBMC | Peripheral blood mononuclear cell, i.e. nucleated cells in the peripheral blood; comprise PBL (peripheral blood lymphocytes) such as T cells. |

Example 1: Isolation of PRAME-Specific T Cell Clone

The present inventors used an in vitro priming approach to isolate T cell clones of any desired MHC restriction and antigen specificity. The priming system uses mature dendritic cells (mDCs) as antigen-presenting cells and autologous CD8$^+$-enriched T cells as responding cells. In vitro transcribed RNA (ivtRNA) encoding the full-length human PRAME amino acid sequence as referenced in SEQ ID NO: 33 serves as the source of specific antigen. After electroporation into the mDCs the ivtRNA is translated into full-length protein, which is subsequently processed and presented as peptides by the MHC molecules of the mDCs. In vitro co-cultures of T cells with the ivtRNA-transfected mDCs from the same donor leads to de novo induction of antigen-specific T cells that serve as the source of corresponding TCRs. Antigen-specific T cells can be enriched by a variety of methods and are cloned by limiting dilution or FACS-based single cell plating.

Example 1.1: Priming Approach Using Mature Dendritic Cells

Figure 1:
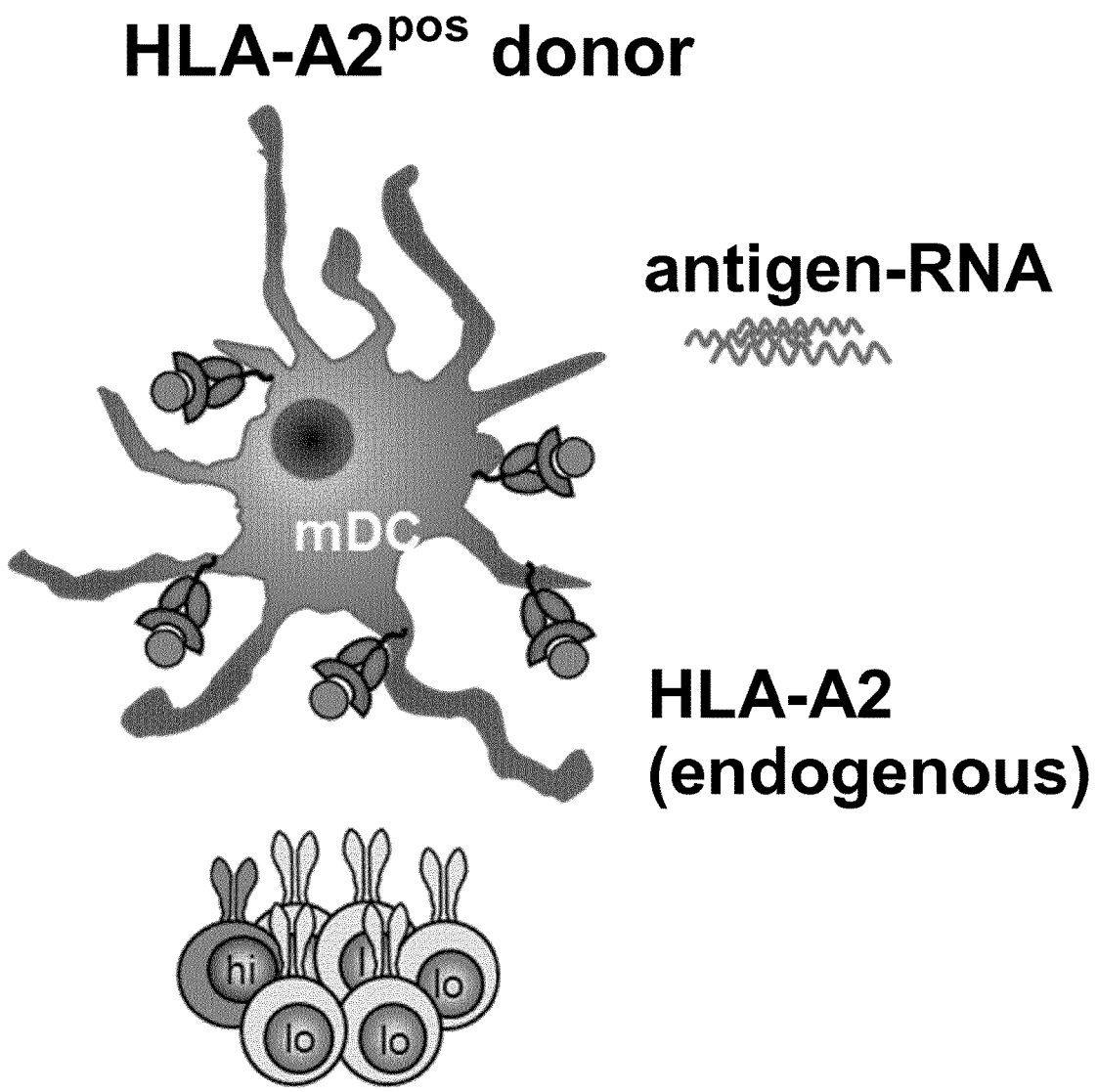
FIG. 1 shows a schematic overview of the priming approach using mature dendritic cells. PRAME-transfected mature dendritic cells were used to de-novo induce PRAME-specific CD8 T cells within the repertoire of the autologous healthy donor.

DC priming of T cells with high-affinity TCR was accomplished using peptide presentation by autologous MHC molecules according to the following protocol (FIG. 1):
HLA-A*02:01/PRAME priming
8 days mDCs produced using suitable maturation cocktails for DCs
APC loading: ivtRNA
Enrichment via HLA-A*02:01 $PRAME_{100\text{-}108}$ multimer
Single cell sorting using FACS technology Example 2: Function/Specificity Analyses Following identification of a candidate T cell clone (T cell clone T4.8-1-29) that recognizes the desired PRAME epitope ($PRAME_{100\text{-}108}$), full characterization regarding function and specificity was conducted. Analyses included the cytokine secretion pattern of the isolated T cell clone (T cell clone T4.8-1-29) in co-culture with various human tumor cell lines, the capacity of the clone to specifically recognize various target cells, the functional avidity of the clone and cytotoxicity towards T2 and tumor cells.

Example 2.1: Analysis of the Original T Cell Clone T4.8-1-29

Example 2.1.1: Poly-Cytokine Analysis

Experimental Layout: Stimulation by Peptide-Loaded T2 Cells

Cytokine release was measured according to the following protocol:

Multiplex® cytokine analysis was performed, detecting IFN-gamma, IL-2, TNF-alpha, IL-5, IL-10, IL-6, IL12p70, IL-4 and IL-1beta Stimulating cells: T2 cells (HLA-A*02$^{pos}$) loaded with saturating amounts ($10^{-5}$ M) of PRAME$_{100-108}$ peptide ("VLD peptide") or irrelevant PRAME$_{300-309}$, i.e. ALYVD-SLFFL peptide ("ALY peptide", SEQ ID NO: 230)

Supernatants of T cell co-cultures, with relevant or irrelevant peptide-loaded T2 cells, were harvested after 24 h and subsequently measured using Multiplex® cytokine analysis.

Results

Figure 2:
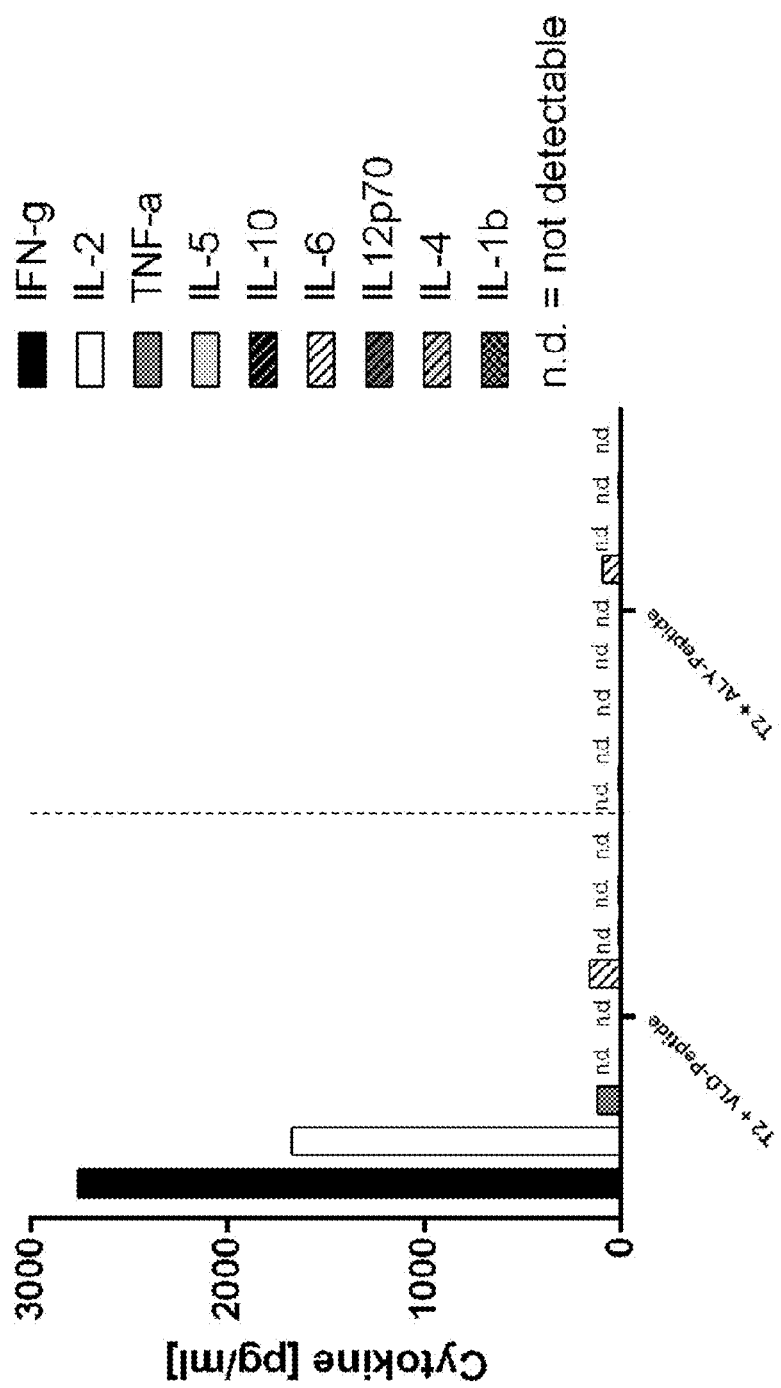
FIG. 2 shows multiplex cytokine secretion analysis (IFN-gamma, IL-2, TNF-alpha, IL-5, IL-10, IL-6, IL12p70, IL-4, IL-1beta) of PRAME$_{100-108}$-specific T cell clone T4.8-1-29 co-cultured with peptide-loaded T2 cells (PRAME$_{100-108}$ "VLD peptide" or PRAME$_{300-309}$ "ALY peptide" as negative control, n.d.=not detected). T4.8-1-29 is characterized by having a CDR3 of its TCR alpha chain variable region as shown in SEQ ID NO: 1 and/or by having a CDR3 of its TCR beta chain variable region as shown in SEQ ID NO: 2.

The candidate clone secreted IFN-gamma, IL-2 and TNF-alpha (Th1/Tc1 cytokines) above background levels. The cytokine expression pattern reflects a Th1 phenotype that is related to good anti-tumor effector function (FIG. 2).

IL-5 and IL-13 (Th2/Tc2 cytokines) secretion was not detected (n.d.).

Example 2.2: Recognition of Tumor Cells

Experimental Layout: Stimulation by Tumor Cell Lines

IFN-gamma ELISA was used to assess cytokine secretion after stimulation with a panel of human tumor cell lines (status of PRAME expression was detected by NanoString® nCounter® (Nanostring Technologies, Inc.) analysis).

Supernatants were harvested after up to 24 h of co-culture of T cell clone T4.8-1-29 with K562-A2, Mel-624.38, Colo-678, 647-V and SuDHL-6 (all HLA-A*02$^{pos}$). Specific IFN-gamma secretion was assessed using standard ELISA.

Target Cells:
K562-A2 (HLA-A*02$^{pos}$, PRAME$^{pos}$)
Mel-624.38 (HLA-A*02$^{pos}$, PRAME$^{pos}$)
Colo-678 (HLA-A*02$^{pos}$, PRAME$^{neg}$)
647-V (HLA-A*02$^{pos}$, PRAME$^{neg}$)
SuDHL-6 (HLA-A*02$^{pos}$, PRAME$^{neg}$)

Results

T cell clone T4.8-1-29 showed high IFN-gamma secretion in co-culture with PRAME$^{pos}$, HLA-A*02$^{pos}$ tumor cell lines K562-A2 and Mel-624.38 (positive control: peptide-pulsed T2 cells)

No PRAME$^{neg}$, HLA-A*02$^{pos}$ tumor cell lines were recognized by T cell clone T4.8 (negative controls; n.d., not detected).

Figure 3:
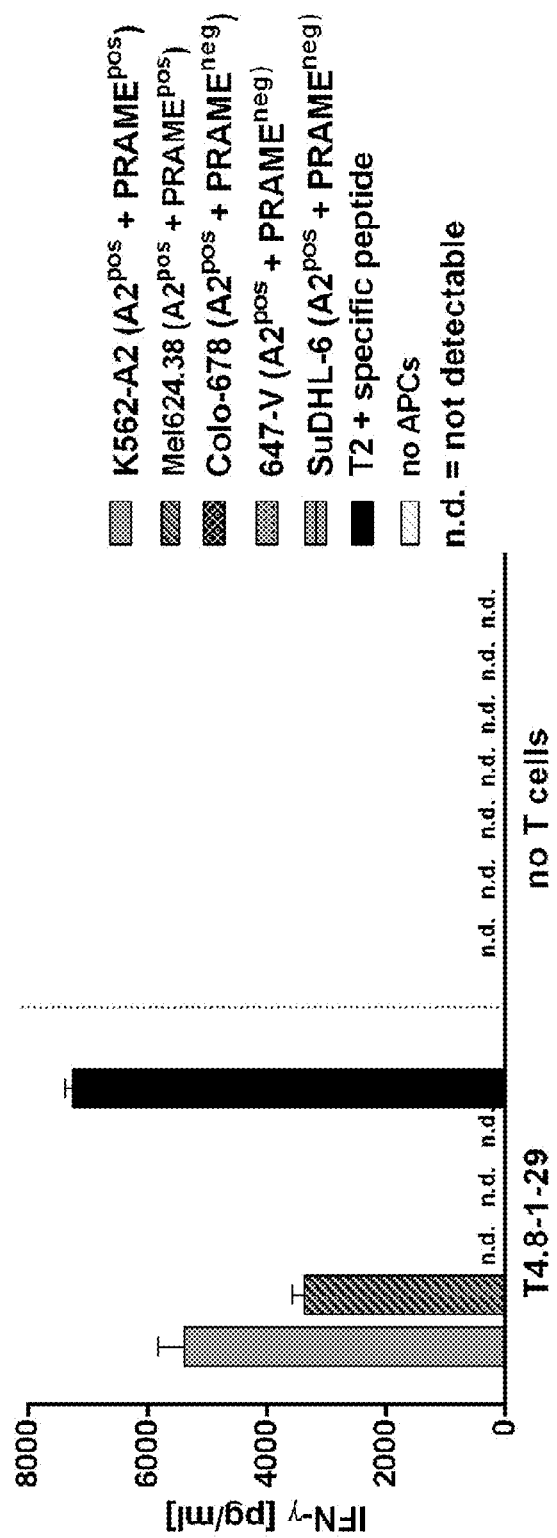
FIG. 3 shows IFN-gamma release from PRAME$_{100-108}$-specific T cell clone T4.8-1-29 co-cultured with various human tumor cell lines expressing HLA-A*02:01, wherein, as indicated in the legend of FIG. 3, some of the tumor cell lines express PRAME (green bars). Tumor cell lines not expressing PRAME serve as negative control (red bars). Positive control: T2 cells loaded with "VLD peptide" (black bar), background of the T cells without stimulation is indicated by white bars ("n.d.=not detected").

Only tumor cell lines expressing HLA-A*02 and PRAME were recognized by the self-restricted T cell clone T4.8-1-29, indicating antigen-specificity (FIG. 3).

Example 2.3: Functional Avidity

Experimental Layout: Stimulation with Peptide-Pulsed T2 Cells

Functional T cell avidity for PRAME$_{100-108}$ (VLD) peptide recognition was measured by detection of IFN-gamma secretion after co-culturing clone T4.8-1-29 with peptide-loaded T2 cells.

Target cells: T2 cells (HLA-A*02$^{pos}$, PRAME$^{neg}$) loaded with titrated amounts of exogenous PRAME$_{100-108}$ (VLD) peptide ($10^{-5}$ M to $10^{-12}$ M).

Effector-to-target ratio (E:T) of 1:1.

The relative IFN-gamma release is displayed in percentage of maximum release. The half-maximal IFN-gamma secretion defining the functional avidity is indicated by dashed lines.

Culture supernatants were harvested after ~24 h of co-culture and assessed by standard ELISA.

Results

Clone T4.8-1-29 showed half-maximal IFN-gamma secretion at between about $1\times10^{-9}$ and $1\times10^{-10}$ mol/L [M] concentration of PRAME$_{100-108}$ peptide (mean of two independent experiments), which lies within the physiological range of virus-specific T cells and is reported to represent the desired functional avidity for efficient anti-tumor efficacy (Aleksic, M et al. Eur. J. Immunol.; 42 (12):3174-3179).

Figure 4:
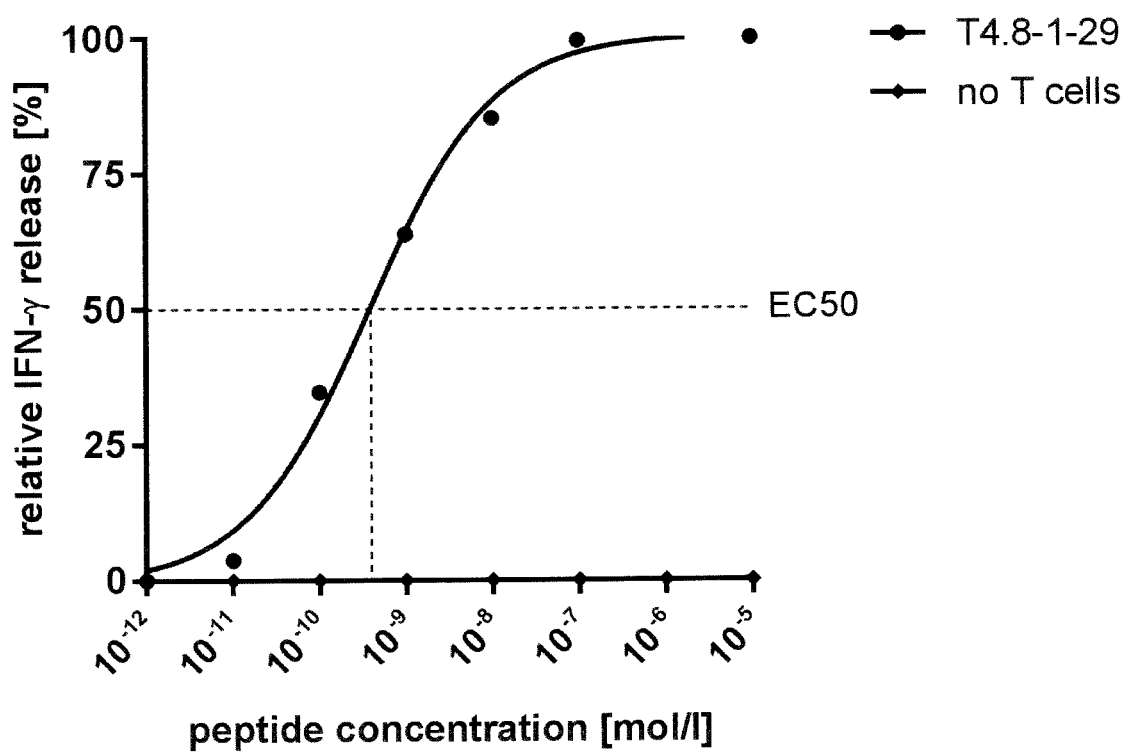
FIG. 4 shows IFN-gamma release of PRAME$_{100-108}$-specific T cell clone T4.8-1-29 co-cultured with T2 cells loaded with titrated amounts of PRAME$_{100-108}$-peptide. The dotted line indicates the peptide concentration leading to half-maximal IFN-gamma secretion between $10^{-9}$-$10^{-10}$ mol/L [M] as a measure for the functional avidity of the tested T cell clone.

→TCR T4.8-1-29:~$1\times10^{-9}$ mol/L[M]　　　　　　　(FIG. 4)

Example 2.3: Analysis of Transgenic T Cell Receptor: TCR T4.8-1-29

Having identified PRAME$^{100-108}$-specific T cell clone T4.8-1-29, next steps involved isolation of the DNA sequence information coding for the corresponding TCR chains, transfer of the cloned TCR into adequate recipient T cells and subsequent functional analysis of the TCR-engineered T cells.

Example 2.3.1: T Cell Receptor Sequence Analysis

DNA sequences of the original clone T4.8-1-29 TCR alpha and beta chains were analyzed in-house by next generation sequencing (NGS-TCRseq). Corresponding TCR alpha and beta DNA sequences were reconstructed by DNA gene synthesis (GeneArt, Regensburg) and cloned into pGEM vector backbones for ivtRNA production as well as retroviral vectors for stable transduction.

Example 2.3.2: Functional Validation of Transgenic TCR

Transfer of TCR Sequence of T Cell Clone T4.8-1-29 into Recipient Cells

TCR DNA sequences of original T cell clone T4.8-1-29 were either in vitro transcribed into RNA encoding the full T4.8-1-29 TCR sequences for transient transfection of recipient effector cells by electroporation, or used for stable transduction of effector cells by using retroviral vector constructs, also encoding the full TCR T4.8-1-29 sequence.

Experimental Layout: Stimulation by Peptide-Pulsed T2 Cells

Specific IFN-gamma secretion of TCR T4.8-1-29-transfected recipient T cells (CD8$^{pos}$ recipient T cell clone+T4.8-

1-29 ivtRNA) in co-culture with PRAME$_{100\text{-}108}$ (VLD) peptide-pulsed T2 cells was measured using standard ELISA.

Target cells: T2 cells (HLA-A*02$^{pos}$, PRAME$^{neg}$) pulsed with 10$^{-5}$ M VLD (relevant) or "ELA peptide" (irrelevant) peptide (ELAGIGILTV, MelanA, SEQ ID NO: 231).

Results

TCR T4.8-1-29-transfected recipient T cells showed good recognition of T2 cells loaded with relevant peptide but no recognition when T2 cells were loaded with irrelevant peptide.

Figure 5:
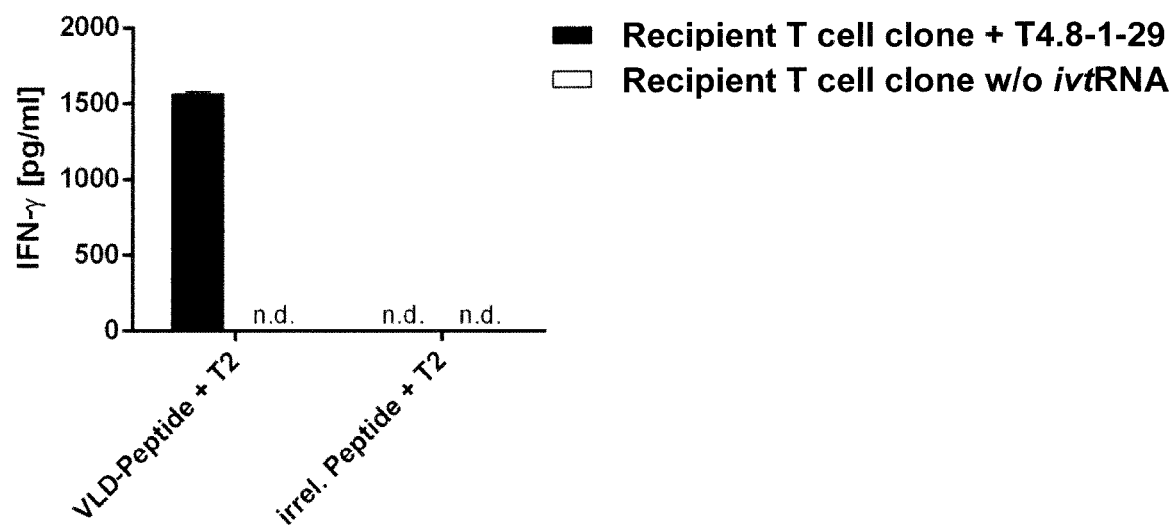
FIG. 5 To prove pairing and functionality of the transgenic TCR, specific IFN-gamma release of PRAME$_{100-108}$-specific TCR T4.8-1-29-transfected recipient CD8$^+$ T (Recipient T cell clone+T4.8-1-29 ivtRNA) cells in co-culture with PRAME$_{100-108}$ (VLD) peptide-loaded T2 cells or T2 cells loaded with irrelevant peptide was measured by standard ELISA.

T4.8-1-29 TCR alpha and beta chain DNA sequences were reconstructed correctly and showed good function as transgenes (FIG. 5)

Example 2.4: Analysis of Recognition of Self-Peptides

Experimental Layout: INF-Gamma Secretion of CD8$^+$ Enriched PBMC Expressing TCR T4.8-1-29 on Co-Culture with Peptide Loaded T2 Cells INF-gamma secretion of CD8+ enriched PBMC expressing the T cell receptor of clone T4.8-1-29.co-cultivated with T2 target cells (HLA-A*02$^{pos}$, PRAME$^{neg}$) loaded with 10$^{-5}$ M PRAME$_{100\text{-}108}$ VLD peptide or ubiquitous self-peptides eluted from HLA-A*02 (131 self-peptides) was determined using ELISA-assay.

Results

Figure 6:
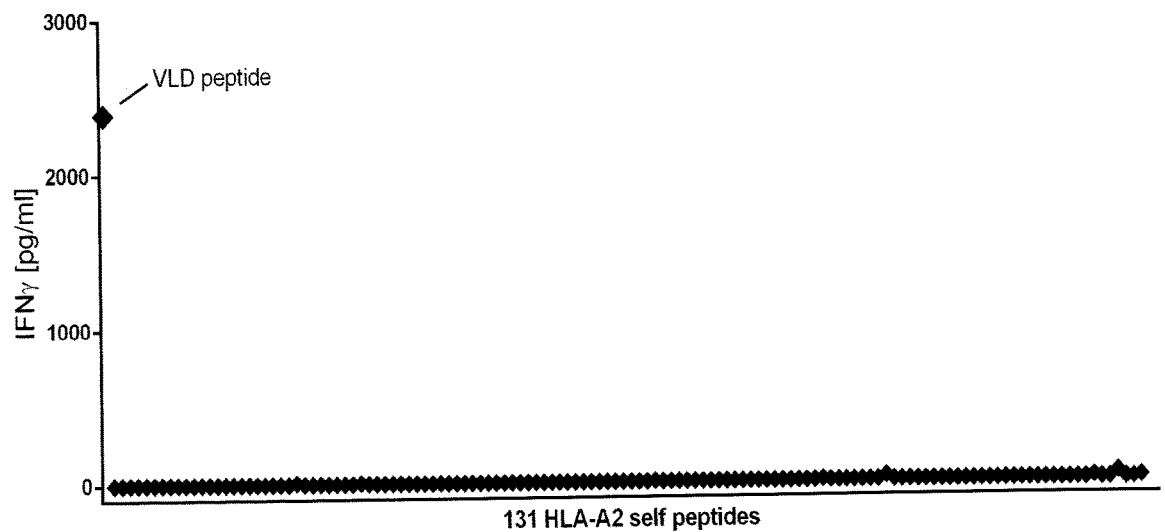
FIG. 6 shows specific IFN-gamma release from PRAME$_{100-108}$-specific CD8+ enriched PBMC engineered to express the PRAME$_{100-108}$-specific TCR T4.8-1-29 in co-culture with self-peptide-loaded (in total 131 ubiquitous self-peptides binding to HLA-A*02:01 encoded molecules) T2 cells measured using standard ELISA.

CD8+ enriched PBMC expressing T cell receptor of clone T4.8-1-29 show no secretion of INF-gamma if co-cultivated with T2 cells (HLA-A*02$^{pos}$, PRAME$^{neg}$) loaded with ubiquitous self-peptides (positive control: PRAME100-108 loaded T2 cells) reflecting high specificity of TCR 4.8-1-29 (FIG. 6).

Example 2.5: Cytotoxicity Analysis

Experimental Layout: Lysis of Peptide-Pulsed T2 Cells

Lysis of PRAME$_{100\text{-}108}$ (VLD) peptide-pulsed T2 cells was measured by using the TVA™ fluorescent killing assay (CTL, Cellular Technology Limited, USA) determining the disappearance of fluorescently labeled target cells during co-culture with CD8 enriched PBMC expressing T4.8-1-29 TCR.

Target cells: T2 cells (HLA-A*02$^{pos}$, PRAME$^{neg}$) pulsed with 10$^{-5}$ M PRAME$_{100\text{-}108}$ VLD (relevant) or SLL (SLLQHLIGL (SEQ ID NO: 229), PRAME, irrelevant) peptide co-cultured with TCR T4.8-1-29 expressing PBMC in graded E:T ratios Results T4.8-1-29 expressing PBMC show efficient lysis of relevant (VLD) peptide-loaded T2 cells even at low E:T ratios.

Figure 7:
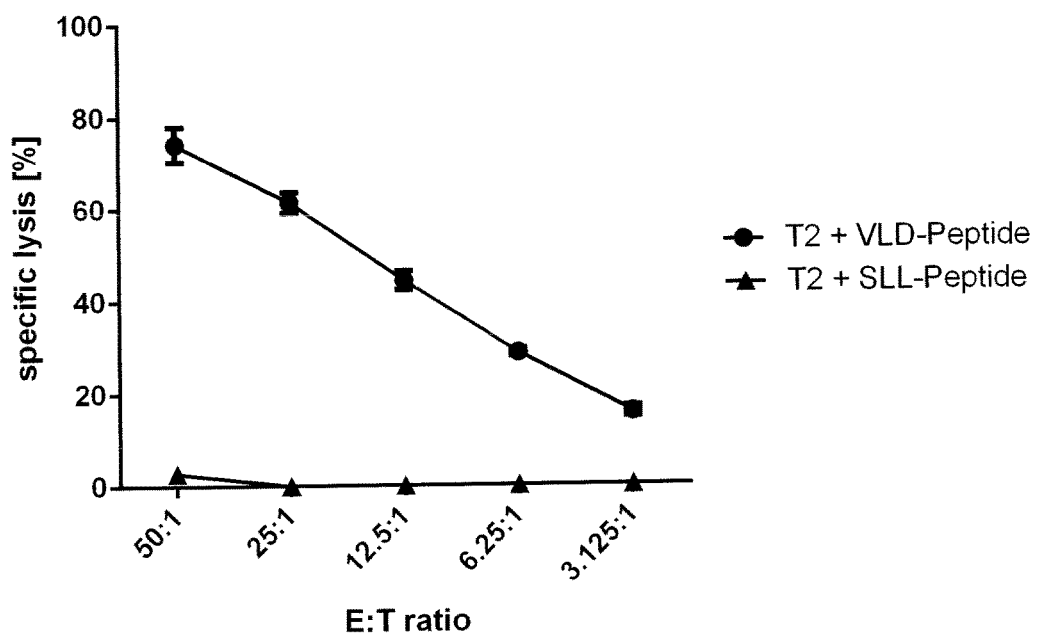
FIG. 7 shows lysis of T2 cells loaded either with PRAME$_{100-108}$-peptide ("VLD-Peptide") or irrelevant peptide SLLQHLIGL (SEQ ID NO: 229) ("SLL-Peptide") by CD8+ enriched PBMC engineered to express the PRAME$_{100-108}$-specific TCR T4.8-1-29.

T2 cells loaded with irrelevant SLL peptide (PRAME) were not lysed (negative control) at any E:T ratio (FIG. 7).

Experimental Layout: Lysis of Tumor Cells

Cytotoxic activity against tumor cells was analyzed using the TVA™ fluorescent killing assay (CTL, Cellular Technology Limited, USA) detecting the disappearance of fluorescently labeled target cells during co-culture with PBMC expressing transgenic TCR of T cell clone T4.8-1-29.

Target cells: Human tumor cell line K562 was used for experiments. K562 cells were transfected using ivtRNA coding for human HLA-A*02:01 and/or ivtRNA coding for human PRAME. Human K562 exhibits endogenous PRAME expression (as determined by Nanostring and reported in literature). In addition, PRAME expression was increased by transfection of K562 cells with ivtRNA coding for human PRAME or by exogenous loading of PRAME$_{100\text{-}108}$ VLD peptide.

K562 transfected with ivtRNA coding for HLA-A*02:01 and loaded with PRAME$_{100\text{-}108}$ (VLD) peptide: K562–(PRAME$^+$/A2$^-$)+A2-ivtRNA+VLD peptide (FIG. 8A)

K562 transduced with ivtRNA coding for PRAME: K562–(PRAME$^+$/A2$^-$)+PRAME-ivtRNA (FIG. 8B)

K562 transfected with ivtRNA coding for PRAME and ivtRNA coding for HLA-A*02: K562–(PRAME$^+$/A2$^-$)+A2-ivtRNA (FIG. 8C)

K562 transfected with ivtRNA coding for HLA-A*02 ivtRNA: K562–(PRAME$^+$/A2-)+A2-ivtRNA+PRAME ivtRNA (FIG. 8D)

Tumor cells were co-cultured with TCR T4.8-1-29-expressing PBMC in graded E:T ratios.

Results

Transfection with PRAME ivtRNA as well as VLD peptide loading of HLA-A*02:01-expressing K562 cells increased specific lysis by PBMC expressing transgenic TCR T4.8-1-29 (FIG. 8A-D).

Example 2.5: Recognition of Tumor Cells by CD8+ Enriched PBMC Expressing TCR T4.8-1-29

Experimental Layout: Stimulation by Tumor Cell Lines

IFN-gamma ELISA was used to assess cytokine secretion after stimulation with a panel of human tumor cell lines (status of PRAME expression was detected by NanoString® nCounter® (Nanostring Technologies, Inc.) analysis).

Supernatants were harvested after up to 24 h of co-culture of CD8$^+$ enriched PBMC expressing T cell receptor T4.8-1-29 with K562-B35, K562-A2, Mel-624.38, Colo-678 and SKMEL23. Specific IFN-gamma secretion was assessed using standard ELISA.

Target Cells:
K562-B35 (HLA-A*02$^{neg}$, PRAME$^{pos}$)
K562-A2 (HLA-A*02$^{pos}$, PRAME$^{pos}$)
K562-A2 (HLA-A*02$^{pos}$, PRAME$^{pos}$) loaded with VLD peptide
Mel-624.38 (HLA-A*02$^{pos}$, PRAME$^{pos}$)
SkMEL23 (HLA-A*02$^{pos}$, PRAME$^{pos}$)

Results

CD8+ enriched PBMC expressing T cell receptor T4.8-1-29 showed high IFN-gamma secretion in co-culture with PRAME$^{pos}$, HLA-A*02$^{pos}$ tumor cell lines K562-A2, K562-A2 additionally loaded with VLD peptide, intermediate INF-gamma secretion upon co-culture with PRAME$^{pos}$, HLA-A*02$^{pos}$ Mel-624.38 and SkMEL23

Figure 10:
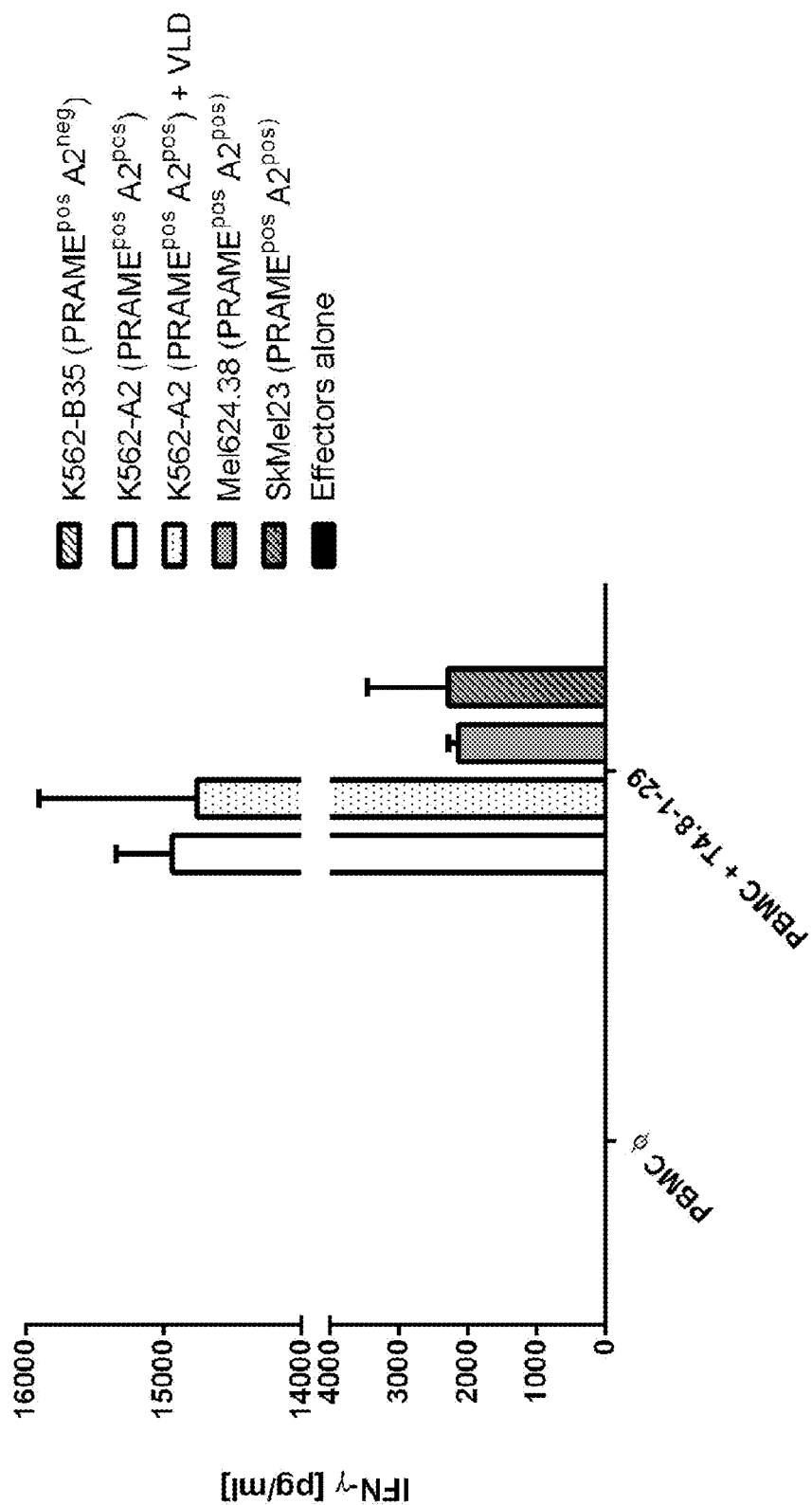
FIG. 10 shows recognition of different HLA-A*02 and PRAME positive tumor cell lines by CD8+ enriched PBMC expressing TCR T4.8-1-29HLA-A*02 as indicated by activation-induced IFN-gamma release and measured by standard ELISA.

PRAME$^{pos}$ K562 with HLA-B*35 expression did not induce INF-gamma secretion confirming HLA-A*02 restriction of TCR T4.8-1-29 (FIG. 10).

Example 2.6: Transduction of PBMC with TCR T4.8-1-29

Figure 11:
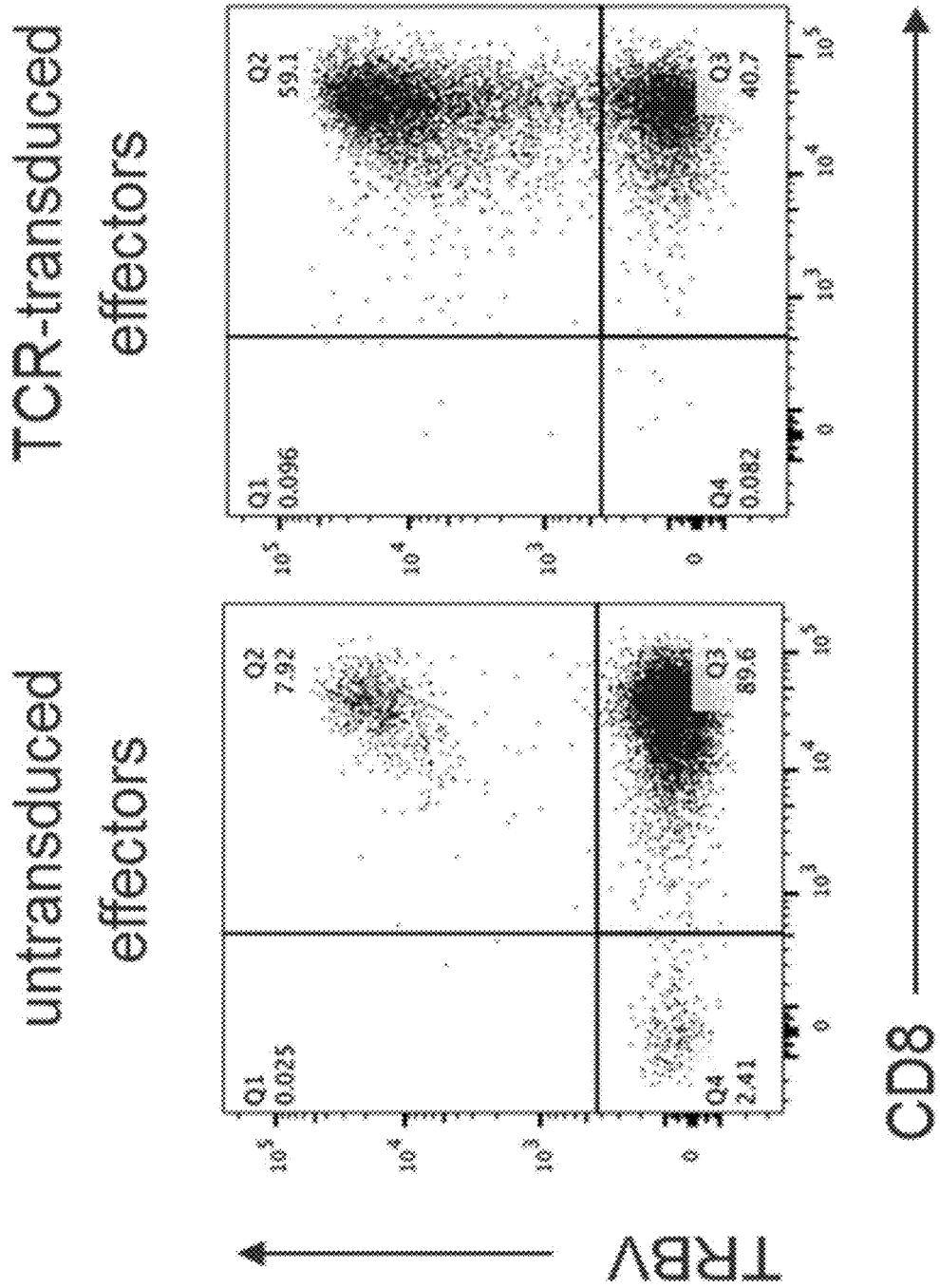
FIG. 11 shows non-transduced PBMC of a healthy donor and the same PBMC of the healthy donor transduced with a plasmid containing the TCT T4.8-1-29 construct described herein.

CD8 enriched PBMC of a healthy donor were transduced with a plasmid containing the TCR T4.8-1-29 construct. To analyze the TCR-transduction-efficiency, FACS analysis was performed after surface staining of untransduced and TCR T4.8-1-29-transduced PBMC. The cells were stained with antibodies specific for CD8 and the TCRs variable region of the TCR ß-chain (TRBV9). In the control effector cell population, there are 8% of endogenously TRBV9-expressing T cells present, while after transduction 60% of T cells expressed TRBV9. This indicates a transduction efficiency of more than 50% (FIG. 11).

Example 2.7: Functional T Cell Avidity for PRAME100-108 (VLD) Peptide by T Cell Clone T4.8-1-29 and PBMC Transduced with TCR T4.8-1-29

Figure 12:
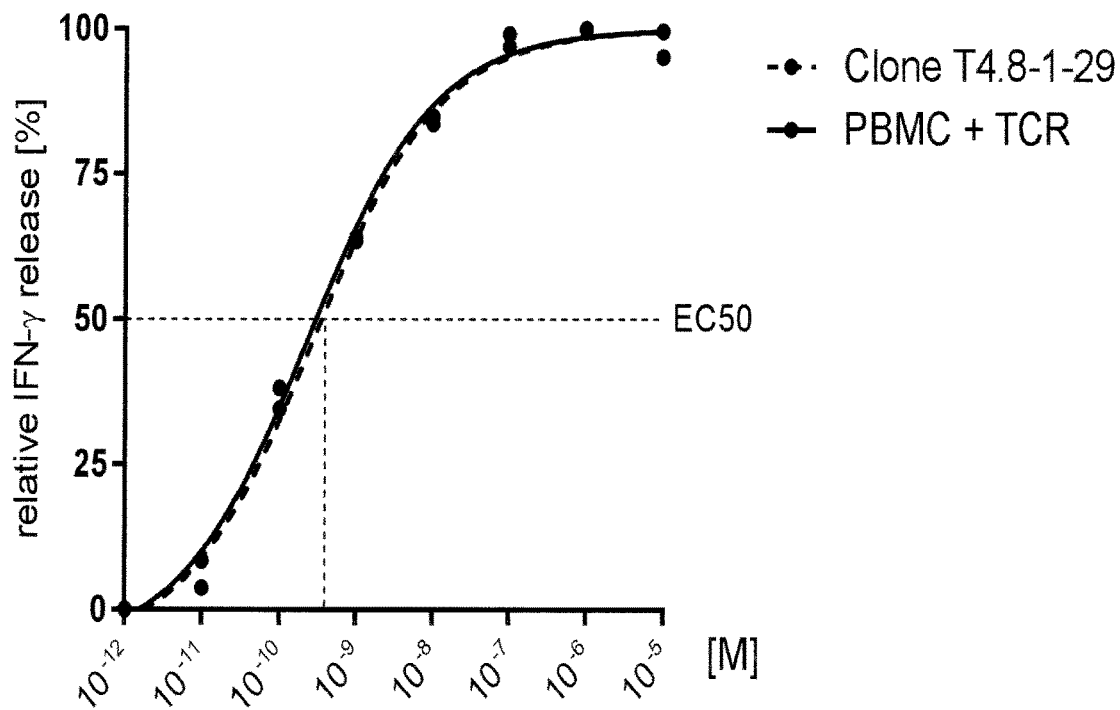
FIG. 12 shows functional T cell avidity for the PRAME$_{100-108}$ (VLD) peptide as measured by detection of IFN-gamma secretion after co-culturing either the T cell clone T4.8-1-29 (dotted curve) or effector PBMC transduced with T4.8-1-29 (solid curve) with peptide-loaded T2 cells.

The functional T cell avidity for the $PRAME_{100-108}$ (VLD) peptide recognition was measured by detection of IFN-gamma secretion after co-culturing either the T cell clone T4.8-1-29 (solid curve) or effector PBMC transduced with T4.8-1-29 (dotted curve) with peptide-loaded T2 cells. The T2 cells were loaded with titrated amounts of peptide, ranging from a concentration of $10^{-5}$ M till $10^{-12}$ M. The coculture-supernatants were harvested after ~24 h of coculture and assessed by standard ELISA, the relative IFN-gamma release is displayed in percentage of maximum release. The half-maximal IFN-gamma-secretion (EC50) defining the functional avidity is indicated by the dashed line. The functional avidity of the original T cell clone and the transgenic TCR are highly similar (FIG. 12).

Example 2.8: Analysis of Antigen Specificity of PBMC Transduced with TCR T4.8-1-29 and Untransduced Control PBMC with Different Target Cells (OPM-2 and U937)

Figure 13:
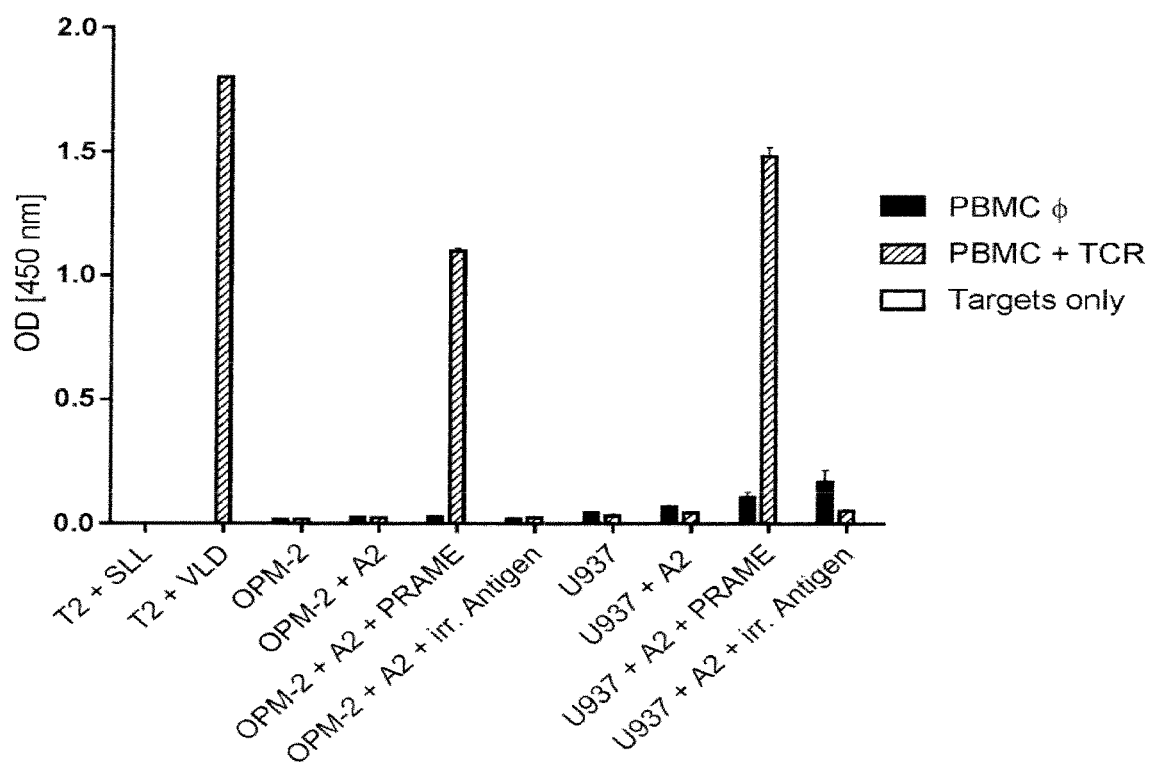
FIG. 13 shows the analysis of antigen specificity of T4.8-1-29-transduced effector PBMC and untransduced control PBMC. The tumor cell lines OPM-2 and U937 (HLA-A2-negative and PRAME-negative) were tested either unmodified, or transfected with ivtRNA encoding HLA-A2

To analyze antigen specificity, T4.8-1-29-transduced effector PBMC and untransduced control PBMC were cocultured with different target cells. The tumor cell lines OPM-2 and U937 (HLA-A2-negative and PRAME-negative) were tested either unmodified, or transfected with ivtRNA encoding HLA-A2. In addition, the cells were also tested after transfection with a combination of ivtRNA encoding for HLA-A2 and PRAME, or HLA-A2 and an irrelevant antigen. As control, the effectors were also cultured with T2 cells loaded with the $PRAME_{VLD}$ peptide ($10^{-5}$ M) or with the irrelevant $PRAME_{SLL}$ peptide ($10^{-5}$ M). After 24 h of coculture, the supernatants were harvested and secreted amounts of IFN-gamma were measured by standard ELISA. High amounts of IFN-gamma were measured for the TCR-transduced PMBC in coculture with the VLD-loaded T2 cells. Also both of the tumor cell lines transfected with HLA-A2 and the antigen PRAME induced IFN-gamma-secretion by the TCR-transduced PBMC. So only tumor cells expressing HLA-A2 as the MHC-restriction-element of need, in combination with the antigen PRAME were recognized and led to an activation of T4.8-1-29-expressing PBMC (FIG. 13), Example 2.9: Analysis of Antigen Specificity of PBMC Transduced with TCR T4.8-1-29 and Untransduced Control PBMC with Different Target Cells (K562, K562_A2 and Mel 624.38)

To analyze antigen specificity, T4.8-1-29-transduced effector PBMC and untransduced control PBMC were cocultured with different target cell lines. The tumor cell lines K562 (HLA-A2-negative and PRAME-positive) were tested as well as K562_A2 and Mel 624.38 (HLA-A-positive and PRAME-positive) and 647-V (HLA-A2-positive and PRAME-negative). As control, the effectors were also cultured with T2 cells loaded with the $PRAME_{VLD}$ peptide ($10^{-5}$ M) or with the irrelevant $PRAME_{SLL}$ peptide ($10^{-5}$ M). After 24 h of co-culture, the supernatants were harvested and secreted amounts of IFN-gamma were measured by standard ELISA. High amounts of IFN-gamma were measured for the TCR-transduced PMBC in coculture with the VLD-loaded T2 cells.

Figure 14:
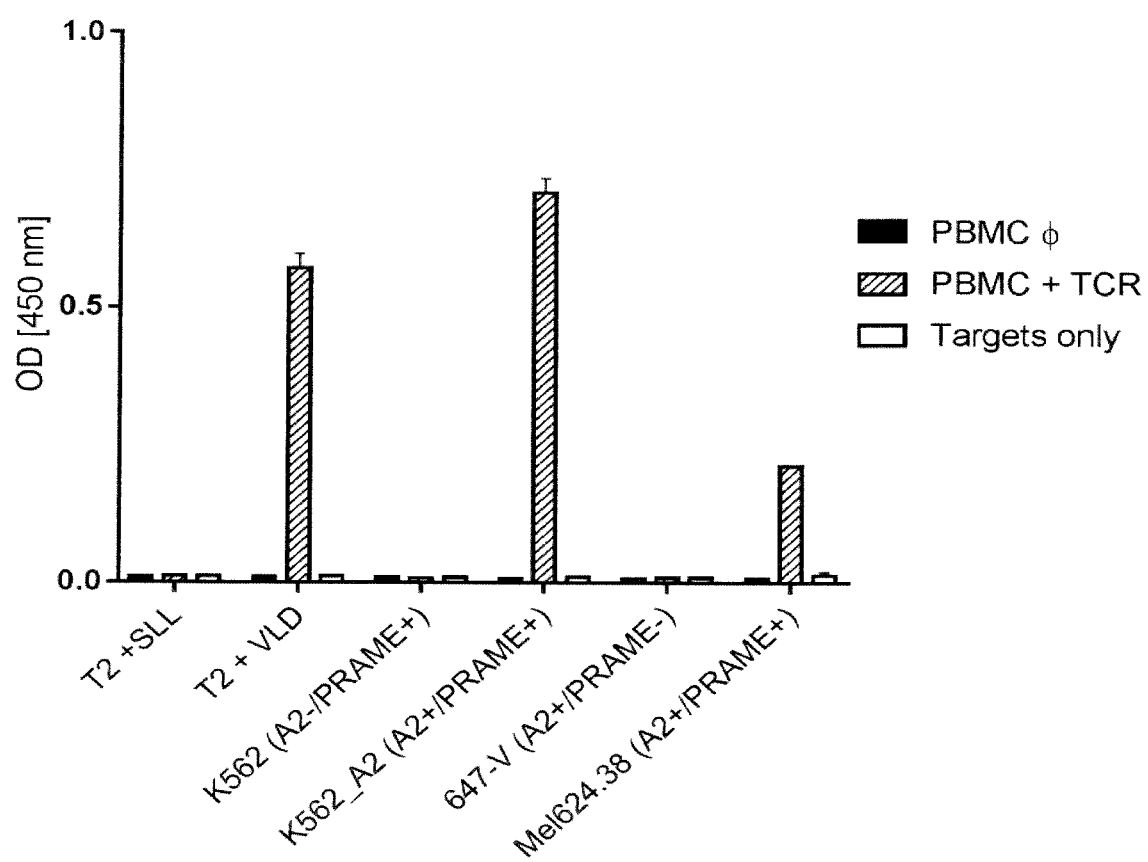
FIG. 14 shows the analysis of antigen specificity, T4.8-1-29-transduced effector PBMC and untransduced control PBMC were cocultured with different target cell lines. The tumor cell lines K562 (HLA-A2-negative and PRAME-positive) were tested as well as K562_A2 and Mel 624.38

Measured IFN-gamma-values indicated activation of TCR T4.8-1-29-transduced PBMC by T2 cells loaded with the VLD-peptide and the tumor cell lines K562_A2 and Mel624.38. So only HLA-A2-positive, endogenously PRAME-expressing tumor cell lines were recognized by the transduced PBMC, while absence of either HLA-A2 or the antigen prevented activation (FIG. 14).

Example 2.10: Analysis Cytotoxic Activity of T4.8-1-29-Transduced Effectors Against Tumor Cells The cytotoxic activity of T4.8-1-29-transduced effectors against tumor cells was analyzed using the IncuCyte ZOOM®—Live Cell Analysis System (Essenbiosciences), a microscope-based system that allows live imaging of cells.

TCR T4.8-1-29-transduced and untransduced effector PBMC were cocultured with the HLA-A2-positive, PRAME-positive melanoma cell line Mel624.38. The melanoma cells were seeded in a 96-well plate and upon reaching a confluency of ~60%, the effector cells were added. To visualize cell death, a red Annexin V-dye was added as well and images were taken on a daily basis for 4 days. Melanoma cell line Mel624.38 in coculture with untransduced effectors (upper row) expanded over time and only rare events of dead cells could be seen, whereas TCR-transduced effectors prevented outgrowth of tumor cells and led to the formation of cell clusters with a high amount of dying cells. This indicates, T4.8-1-29-expressing effector cells can efficiently lyse PRAME-expressing tumor cells and prevent outgrowth of tumor cells for several days.

Example 2.11: Analysis of the Safety Profile of T4.8-1-29-Expressing PBMC

To analyze the safety profile of T4.8-1-29-expressing PBMC, the recognition of healthy human tissues has to be excluded. Therefore, T4.8-1-29-transduced PBMC derived from two different donors, were cocultured with cells derived from healthy tissues of HLA-A2-positive donors. As an example, transduced as well as untransduced PBMC were cocultured with human renal capillary epithelial cells (HR-CEpC). As a control the HRCEp cells were additionally loaded with the VLD-peptide ($10^{-5}$ M). After 24 h of coculture, the supernatants were harvested and secreted amounts of IFN-gamma were measured by standard ELISA. The TCR-transduced PBMC were only activated upon coculture with the peptide loaded target cells, while there was no recognition of the unmodified HRCEp cells.

The invention claimed is:

1. A T-cell receptor (TCR) comprising:
   (i) a CDR alpha chain comprising a variable region having a CDR1 consisting of the amino acid sequence VSGLRG (SEQ ID NO: 5), a CDR2 consisting of the amino acid sequence of LYSAGEE (SEQ ID NO: 3), and a CDR3 consisting of the amino acid sequence of CAVHSTAQAGTALIF (SEQ ID NO: 1); and
   (ii) a CDR beta chain comprising a variable region having a CDR1 consisting of the amino acid sequence of SGDLS (SEQ ID NO: 6), a CDR2 consisting of the amino acid sequence YYNGEE (SEQ ID NO: 4), and a CDR3 consisting of the amino acid sequence of CASSTHRGQTNYGYTF (SEQ ID NO: 2),
   said TCR being capable of binding to the epitope comprised within the amino acid A sequence of VLDGLDVLL (SEQ ID NO:32) in its HLA-A*02:01-bound form.

2. The TCR according to claim 1, comprising
   (i) a TCR alpha chain variable region comprising or consisting of the amino acid sequence depicted in SEQ ID NO: 15, and
   (ii) a TCR beta chain variable region comprising or consisting of the amino acid sequence depicted in SEQ ID NO: 16.

3. The TCR according to claim 1, comprising
   (i) a TCR alpha chain comprising or consisting of an amino acid sequence selected from SEQ ID NO: 7; SEQ ID NO: 9, SEQ ID NO: 11, or SEQ ID NO: 13, and
   (ii) a TCR beta-chain comprising or consisting of an amino acid sequence selected from of SEQ ID NO: 8, SEQ ID NO: 10, SEQ ID NO: 12, or SEQ ID NO: 14.

4. The TCR according to claim 1, wherein said TCR is a TCR construct.

5. The TCR construct according to claim 4, comprising at least one TCR alpha-chain(s) and at least one TCR beta-chain(s) covalently linked to each other to form TCR heterodimers or multimers.

6. The TCR according to claim 1, further comprising one or more fusion component(s) optionally selected from the group consisting of Fc receptors, Fc domains, cytokines, toxins, antibodies or antigen-binding fragments thereof, CD247 (CD3-zeta), CD28, CD137, CD134 domain, or combinations thereof, optionally further comprising at least one linker.

7. The TCR according to claim 1, comprising
   (i) at least one TCR alpha chain variable region comprising or consisting of the amino acid sequence depicted in SEQ ID NO: 15,
   (ii) at least one TCR beta chain variable region comprising or consisting of the amino acid sequence depicted in SEQ ID NO: 16, and (iii) an antibody or a single chain antibody fragment (scFv) which is directed against an antigen or epitope on the surface of lymphocytes, wherein the TCR alpha-chain(s) and TCR beta-chain(s) are linked to each other and fused, optionally via a linker, to said antibody or scFv.

8. The TCR according to claim 7, wherein said antigen is selected from CD3, CD28, CD5, CD16 or CD56.

9. The TCR according to claim 1, further comprising at least one label.

10. The TCR according to claim 1 which is soluble.

11. The TCR according to claim 6, wherein said Fc domain is selected from the group consisting of IgA, IgD, IgG, IgE, and IgM.

12. The TCR according to claim 6, wherein said cytokine is IL-2 or IL-15.

13. The TCR according to claim 6, wherein said antibody or antigen-binding fragments thereof is an anti-CD3, anti-CD28, anti-CD5, anti-CD16 or anti-CD56 antibody or antigen-binding fragment thereof.

* * * * *

SEQUENCE LISTING

<160> NUMBER OF SEQ ID NOS: 231

<210> SEQ ID NO 1
<211> LENGTH: 15
<212> TYPE: PRT
<213> ORGANISM: homo sapiens
<220> FEATURE:
<221> NAME/KEY: MISC_Feature
<223> OTHER INFORMATION: CDR3 alpha

<400> SEQUENCE: 1

Cys Ala Val His Ser Thr Ala Gln Ala Gly Thr Ala Leu Ile Phe
1               5                   10                  15

<210> SEQ ID NO 2
<211> LENGTH: 16
<212> TYPE: PRT
<213> ORGANISM: homo sapiens
<220> FEATURE:
<221> NAME/KEY: MISC_feature
<223> OTHER INFORMATION: CDR3 beta

<400> SEQUENCE: 2

Cys Ala Ser Ser Thr His Arg Gly Gln Thr Asn Tyr Gly Tyr Thr Phe
1               5                   10                  15

<210> SEQ ID NO 3
<211> LENGTH: 7
<212> TYPE: PRT
<213> ORGANISM: homo sapiens
<220> FEATURE:
<221> NAME/KEY: MISC_feature
<223> OTHER INFORMATION: CDR2 alpha

<400> SEQUENCE: 3

Leu Tyr Ser Ala Gly Glu Glu
1               5

<210> SEQ ID NO 4
<211> LENGTH: 6
<212> TYPE: PRT
<213> ORGANISM: homo sapiens
<220> FEATURE:
<221> NAME/KEY: MISC_feature
<223> OTHER INFORMATION: CDR2 beta

<400> SEQUENCE: 4

Tyr Tyr Asn Gly Glu Glu
1               5

<210> SEQ ID NO 5
<211> LENGTH: 6
<212> TYPE: PRT
<213> ORGANISM: homo sapiens
<220> FEATURE:
<221> NAME/KEY: MISC_feature
<223> OTHER INFORMATION: CDR1 alpha

<400> SEQUENCE: 5

Val Ser Gly Leu Arg Gly
1               5

<210> SEQ ID NO 6
<211> LENGTH: 5
<212> TYPE: PRT
<213> ORGANISM: homo sapiens

-continued

```
<220> FEATURE:
<221> NAME/KEY: MISC_feature
<223> OTHER INFORMATION: CDR1 beta

<400> SEQUENCE: 6

Ser Gly Asp Leu Ser
1               5

<210> SEQ ID NO 7
<211> LENGTH: 274
<212> TYPE: PRT
<213> ORGANISM: homo sapiens
<220> FEATURE:
<221> NAME/KEY: MISC_feature
<223> OTHER INFORMATION: TCR alpha wt full length

<400> SEQUENCE: 7

Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Leu Asn Cys Ser Tyr Thr Val
        35                  40                  45

Ser Gly Leu Arg Gly Leu Phe Trp Tyr Arg Gln Asp Pro Gly Lys Gly
    50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val His
            100                 105                 110

Ser Thr Ala Gln Ala Gly Thr Ala Leu Ile Phe Gly Lys Gly Thr Thr
        115                 120                 125

Leu Ser Val Ser Ser Asn Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 8
<211> LENGTH: 311
<212> TYPE: PRT
<213> ORGANISM: homo sapiens
```

```
<220> FEATURE:
<221> NAME/KEY: MISC_feature
<223> OTHER INFORMATION: TCR beta wt full length

<400> SEQUENCE: 8

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Thr His Arg Gly Gln Thr Asn Tyr Gly Tyr Thr Phe Gly Ser Gly
        115                 120                 125

Thr Arg Leu Thr Val Val Glu Asp Leu Asn Lys Val Phe Pro Pro Glu
    130                 135                 140

Val Ala Val Phe Glu Pro Ser Glu Ala Glu Ile Ser His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Pro Leu Lys Glu Gln Pro Ala Leu Asn Asp Ser Arg Tyr
        195                 200                 205

Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Phe Thr Ser Val Ser Tyr
            260                 265                 270

Gln Gln Gly Val Leu Ser Ala Thr Ile Leu Tyr Glu Ile Leu Leu Gly
        275                 280                 285

Lys Ala Thr Leu Tyr Ala Val Leu Val Ser Ala Leu Val Leu Met Ala
    290                 295                 300

Met Val Lys Arg Lys Asp Phe
305                 310

<210> SEQ ID NO 9
<211> LENGTH: 274
<212> TYPE: PRT
<213> ORGANISM: artificial
<220> FEATURE:
<223> OTHER INFORMATION: TCR alpha full length humC
```

-continued

<400> SEQUENCE: 9

```
Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Leu Asn Cys Ser Tyr Thr Val
        35                  40                  45

Ser Gly Leu Arg Gly Leu Phe Trp Tyr Arg Gln Asp Pro Gly Lys Gly
    50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val His
            100                 105                 110

Ser Thr Ala Gln Ala Gly Thr Ala Leu Ile Phe Gly Lys Gly Thr Thr
        115                 120                 125

Leu Ser Val Ser Ser Asn Ile Gln Asn Pro Asp Pro Ala Val Tyr Gln
130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Met Thr Leu Arg Leu Trp
            260                 265                 270

Ser Ser
```

<210> SEQ ID NO 10
<211> LENGTH: 311
<212> TYPE: PRT
<213> ORGANISM: artificial
<220> FEATURE:
<223> OTHER INFORMATION: TCR beta humC full length

<400> SEQUENCE: 10

```
Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80
```

```
Glu Arg Phe Ser Ala Gln Gln Phe Pro Asp Leu His Ser Glu Leu Asn
                85                  90                  95
Leu Ser Ser Leu Glu Leu Gly Asp Ser Ala Leu Tyr Phe Cys Ala Ser
            100                 105                 110
Ser Thr His Arg Gly Gln Thr Asn Tyr Gly Tyr Thr Phe Gly Ser Gly
            115                 120                 125
Thr Arg Leu Thr Val Val Glu Asp Leu Asn Lys Val Phe Pro Pro Glu
            130                 135                 140
Val Ala Val Phe Glu Pro Ser Glu Ala Glu Ile Ser His Thr Gln Lys
145                 150                 155                 160
Ala Thr Leu Val Cys Leu Ala Thr Gly Phe Phe Pro Asp His Val Glu
                165                 170                 175
Leu Ser Trp Trp Val Asn Gly Lys Glu Val His Ser Gly Val Ser Thr
                180                 185                 190
Asp Pro Gln Pro Leu Lys Glu Gln Pro Ala Leu Asn Asp Ser Arg Tyr
            195                 200                 205
Cys Leu Ser Ser Arg Leu Arg Val Ser Ala Thr Phe Trp Gln Asn Pro
            210                 215                 220
Arg Asn His Phe Arg Cys Gln Val Gln Phe Tyr Gly Leu Ser Glu Asn
225                 230                 235                 240
Asp Glu Trp Thr Gln Asp Arg Ala Lys Pro Val Thr Gln Ile Val Ser
                245                 250                 255
Ala Glu Ala Trp Gly Arg Ala Asp Cys Gly Phe Thr Ser Val Ser Tyr
                260                 265                 270
Gln Gln Gly Val Leu Ser Ala Thr Ile Leu Tyr Glu Ile Leu Leu Gly
            275                 280                 285
Lys Ala Thr Leu Tyr Ala Val Leu Val Ser Ala Leu Val Leu Met Ala
            290                 295                 300
Met Val Lys Arg Lys Asp Phe
305                 310

<210> SEQ ID NO 11
<211> LENGTH: 274
<212> TYPE: PRT
<213> ORGANISM: artificial
<220> FEATURE:
<223> OTHER INFORMATION: TCR alpha mmcys full length

<400> SEQUENCE: 11

Met Glu Lys Met Leu Glu Cys Ala Phe Ile Val Leu Trp Leu Gln Leu
1               5                   10                  15
Gly Trp Leu Ser Gly Glu Asp Gln Val Thr Gln Ser Pro Glu Ala Leu
            20                  25                  30
Arg Leu Gln Glu Gly Glu Ser Ser Leu Asn Cys Ser Tyr Thr Val
            35                  40                  45
Ser Gly Leu Arg Gly Leu Phe Trp Tyr Arg Gln Asp Pro Gly Lys Gly
            50                  55                  60
Pro Glu Phe Leu Phe Thr Leu Tyr Ser Ala Gly Glu Glu Lys Glu Lys
65                  70                  75                  80
Glu Arg Leu Lys Ala Thr Leu Thr Lys Lys Glu Ser Phe Leu His Ile
                85                  90                  95
Thr Ala Pro Lys Pro Glu Asp Ser Ala Thr Tyr Leu Cys Ala Val His
            100                 105                 110
Ser Thr Ala Gln Ala Gly Thr Ala Leu Ile Phe Gly Lys Gly Thr Thr
            115                 120                 125
```

```
Leu Ser Val Ser Ser Asn Ile Gln Asn Pro Asp Pro Ala Val Tyr Gln
            130                 135                 140

Leu Arg Asp Ser Lys Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                    165                 170                 175

Ile Thr Asp Lys Cys Val Leu Asp Met Arg Ser Met Asp Phe Lys Ser
                180                 185                 190

Asn Ser Ala Val Ala Trp Ser Asn Lys Ser Asp Phe Ala Cys Ala Asn
                195                 200                 205

Ala Phe Asn Asn Ser Ile Ile Pro Glu Asp Thr Phe Phe Pro Ser Ser
210                 215                 220

Asp Val Pro Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
                260                 265                 270

Ser Ser

<210> SEQ ID NO 12
<211> LENGTH: 311
<212> TYPE: PRT
<213> ORGANISM: artificial
<220> FEATURE:
<223> OTHER INFORMATION: TCR beta mmcys full length

<400> SEQUENCE: 12

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
                20                  25                  30

Ala Thr Gly Gln Arg Val Thr Leu Arg Cys Ser Pro Arg Ser Gly Asp
            35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
                100                 105                 110

Ser Thr His Arg Gly Gln Thr Asn Tyr Gly Tyr Thr Phe Gly Ser Gly
            115                 120                 125

Thr Arg Leu Thr Val Val Glu Asp Leu Asn Lys Val Phe Pro Pro Glu
        130                 135                 140

Val Ala Val Phe Glu Pro Ser Lys Ala Glu Ile Ala His Thr Gln Lys
145                 150                 155                 160

Ala Thr Leu Val Cys Leu Ala Thr Gly Phe Phe Pro Asp His Val Glu
                165                 170                 175

Leu Ser Trp Trp Val Asn Gly Lys Glu Val His Ser Gly Val Cys Thr
                180                 185                 190

Asp Pro Gln Pro Leu Lys Glu Gln Pro Ala Leu Asn Asp Ser Arg Tyr
            195                 200                 205
```

```
Cys Leu Ser Ser Arg Leu Arg Val Ser Ala Thr Phe Trp Gln Asn Pro
    210                 215                 220

Arg Asn His Phe Arg Cys Gln Val Gln Phe Tyr Gly Leu Ser Glu Asn
225                 230                 235                 240

Asp Glu Trp Thr Gln Asp Arg Ala Lys Pro Val Thr Gln Ile Val Ser
                245                 250                 255

Ala Glu Ala Trp Gly Arg Ala Asp Cys Gly Ile Thr Ser Ala Ser Tyr
                260                 265                 270

His Gln Gly Val Leu Ser Ala Thr Ile Leu Tyr Glu Ile Leu Leu Gly
            275                 280                 285

Lys Ala Thr Leu Tyr Ala Val Leu Val Ser Ala Leu Val Leu Met Ala
    290                 295                 300

Met Val Lys Arg Lys Asp Phe
305                 310

<210> SEQ ID NO 13
<211> LENGTH: 270
<212> TYPE: PRT
<213> ORGANISM: artificial
<220> FEATURE:
<223> OTHER INFORMATION: TCR alpha murC full length

<400> SEQUENCE: 13

Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Ser Leu Asn Cys Ser Tyr Thr Val
        35                  40                  45

Ser Gly Leu Arg Gly Leu Phe Trp Tyr Arg Gln Asp Pro Gly Lys Gly
    50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val His
            100                 105                 110

Ser Thr Ala Gln Ala Gly Thr Ala Leu Ile Phe Gly Lys Gly Thr Thr
        115                 120                 125

Leu Ser Val Ser Ser Asn Ile Gln Asn Pro Glu Pro Ala Val Tyr Gln
    130                 135                 140

Leu Lys Asp Pro Arg Ser Gln Asp Ser Thr Leu Cys Leu Phe Thr Asp
145                 150                 155                 160

Phe Asp Ser Gln Ile Asn Val Pro Lys Thr Met Glu Ser Gly Thr Phe
                165                 170                 175

Ile Thr Asp Lys Thr Val Leu Asp Met Lys Ala Met Asp Ser Lys Ser
            180                 185                 190

Asn Gly Ala Ile Ala Trp Ser Asn Gln Thr Ser Phe Thr Cys Gln Asp
        195                 200                 205

Ile Phe Lys Glu Thr Asn Ala Thr Tyr Pro Ser Ser Asp Val Pro Cys
    210                 215                 220

Asp Ala Thr Leu Thr Glu Lys Ser Phe Glu Thr Asp Met Asn Leu Asn
225                 230                 235                 240
```

Phe Gln Asn Leu Ser Val Met Gly Leu Arg Ile Leu Leu Lys Val
                    245                 250                 255

Ala Gly Phe Asn Leu Leu Met Thr Leu Arg Leu Trp Ser Ser
                260                 265                 270

<210> SEQ ID NO 14
<211> LENGTH: 307
<212> TYPE: PRT
<213> ORGANISM: artificial
<220> FEATURE:
<223> OTHER INFORMATION: TCR beta murC full length

<400> SEQUENCE: 14

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
                20                  25                  30

Ala Thr Gly Gln Arg Val Thr Leu Arg Cys Ser Pro Arg Ser Gly Asp
            35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Thr His Arg Gly Gln Thr Asn Tyr Gly Tyr Thr Phe Gly Ser Gly
        115                 120                 125

Thr Arg Leu Thr Val Val Glu Asp Leu Arg Asn Val Thr Pro Pro Lys
130                 135                 140

Val Thr Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Ala Tyr Lys Glu Ser Asn Tyr Ser Tyr Cys Leu Ser Ser
        195                 200                 205

Arg Leu Arg Val Ser Ala Thr Phe Trp His Asn Pro Arg Asn His Phe
210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr His Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Gly Leu Val Leu Met Ala Met Val Lys Lys
    290                 295                 300

Lys Asn Ser
305

-continued

```
<210> SEQ ID NO 15
<211> LENGTH: 134
<212> TYPE: PRT
<213> ORGANISM: homo sapiens
<220> FEATURE:
<221> NAME/KEY: MISC_feature
<223> OTHER INFORMATION: TCR alpha variable

<400> SEQUENCE: 15

Met Glu Lys Met Leu Glu Cys Ala Phe Ile Val Leu Trp Leu Gln Leu
1               5                   10                  15

Gly Trp Leu Ser Gly Glu Asp Gln Val Thr Gln Ser Pro Glu Ala Leu
            20                  25                  30

Arg Leu Gln Glu Gly Glu Ser Ser Leu Asn Cys Ser Tyr Thr Val
        35                  40                  45

Ser Gly Leu Arg Gly Leu Phe Trp Tyr Arg Gln Asp Pro Gly Lys Gly
    50                  55                  60

Pro Glu Phe Leu Phe Thr Leu Tyr Ser Ala Gly Glu Glu Lys Glu Lys
65                  70                  75                  80

Glu Arg Leu Lys Ala Thr Leu Thr Lys Lys Glu Ser Phe Leu His Ile
                85                  90                  95

Thr Ala Pro Lys Pro Glu Asp Ser Ala Thr Tyr Leu Cys Ala Val His
            100                 105                 110

Ser Thr Ala Gln Ala Gly Thr Ala Leu Ile Phe Gly Lys Gly Thr Thr
        115                 120                 125

Leu Ser Val Ser Ser Asn
    130

<210> SEQ ID NO 16
<211> LENGTH: 134
<212> TYPE: PRT
<213> ORGANISM: artificial
<220> FEATURE:
<223> OTHER INFORMATION: TCR beta variable
<220> FEATURE:
<221> NAME/KEY: MISC_feature
<223> OTHER INFORMATION: TCR beta variable

<400> SEQUENCE: 16

Met Gly Phe Arg Leu Leu Cys Cys Val Ala Phe Cys Leu Leu Gly Ala
1               5                   10                  15

Gly Pro Val Asp Ser Gly Val Thr Gln Thr Pro Lys His Leu Ile Thr
            20                  25                  30

Ala Thr Gly Gln Arg Val Thr Leu Arg Cys Ser Pro Arg Ser Gly Asp
        35                  40                  45

Leu Ser Val Tyr Trp Tyr Gln Gln Ser Leu Asp Gln Gly Leu Gln Phe
    50                  55                  60

Leu Ile Gln Tyr Tyr Asn Gly Glu Glu Arg Ala Lys Gly Asn Ile Leu
65                  70                  75                  80

Glu Arg Phe Ser Ala Gln Gln Phe Pro Asp Leu His Ser Glu Leu Asn
                85                  90                  95

Leu Ser Ser Leu Glu Leu Gly Asp Ser Ala Leu Tyr Phe Cys Ala Ser
            100                 105                 110

Ser Thr His Arg Gly Gln Thr Asn Tyr Gly Tyr Thr Phe Gly Ser Gly
        115                 120                 125

Thr Arg Leu Thr Val Val
    130
```

```
<210> SEQ ID NO 17
<211> LENGTH: 140
<212> TYPE: PRT
<213> ORGANISM: homo sapiens
<220> FEATURE:
<221> NAME/KEY: MISC_FEATURE
<223> OTHER INFORMATION: TCR alpha wt constant

<400> SEQUENCE: 17

Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
            20                  25                  30

Val Ser Gln Ser Lys Asp Ser Asp Val Tyr Ile Thr Asp Lys Thr Val
        35                  40                  45

Leu Asp Met Arg Ser Met Asp Phe Lys Ser Asn Ser Ala Val Ala Trp
    50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Pro Glu Ser Ser Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
    130                 135                 140

<210> SEQ ID NO 18
<211> LENGTH: 177
<212> TYPE: PRT
<213> ORGANISM: homo sapiens
<220> FEATURE:
<221> NAME/KEY: MISC_FEATURE
<223> OTHER INFORMATION: TCR beta wt constant

<400> SEQUENCE: 18

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160
```

```
Val Leu Val Ser Ala Leu Val Leu Met Ala Met Val Lys Arg Lys Asp
                165                 170                 175

Phe

<210> SEQ ID NO 19
<211> LENGTH: 140
<212> TYPE: PRT
<213> ORGANISM: artificial
<220> FEATURE:
<223> OTHER INFORMATION: TCR alpha minimal murinized constant
<220> FEATURE:
<221> NAME/KEY: MISC_feature
<223> OTHER INFORMATION: TCR alpha mmcys constant

<400> SEQUENCE: 19

Ile Gln Asn Pro Asp Pro Ala Val Tyr Gln Leu Arg Asp Ser Lys Ser
1               5                   10                  15

Ser Asp Lys Ser Val Cys Leu Phe Thr Asp Phe Asp Ser Gln Thr Asn
                20                  25                  30

Val Ser Gln Ser Lys Asp Ser Asp Val Tyr Ile Thr Asp Lys Cys Val
            35                  40                  45

Leu Asp Met Arg Ser Met Asp Phe Lys Ser Asn Ser Ala Val Ala Trp
50                  55                  60

Ser Asn Lys Ser Asp Phe Ala Cys Ala Asn Ala Phe Asn Asn Ser Ile
65                  70                  75                  80

Ile Pro Glu Asp Thr Phe Phe Pro Ser Ser Asp Val Pro Cys Asp Val
                85                  90                  95

Lys Leu Val Glu Lys Ser Phe Glu Thr Asp Thr Asn Leu Asn Phe Gln
            100                 105                 110

Asn Leu Ser Val Ile Gly Phe Arg Ile Leu Leu Leu Lys Val Ala Gly
        115                 120                 125

Phe Asn Leu Leu Met Thr Leu Arg Leu Trp Ser Ser
130                 135                 140

<210> SEQ ID NO 20
<211> LENGTH: 177
<212> TYPE: PRT
<213> ORGANISM: artificial
<220> FEATURE:
<223> OTHER INFORMATION: TCR beta minimally murinized C
<220> FEATURE:
<221> NAME/KEY: MISC_feature
<223> OTHER INFORMATION: TCR beta mmcys constant

<400> SEQUENCE: 20

Glu Asp Leu Asn Lys Val Phe Pro Pro Glu Val Ala Val Phe Glu Pro
1               5                   10                  15

Ser Lys Ala Glu Ile Ala His Thr Gln Lys Ala Thr Leu Val Cys Leu
                20                  25                  30

Ala Thr Gly Phe Phe Pro Asp His Val Glu Leu Ser Trp Trp Val Asn
            35                  40                  45

Gly Lys Glu Val His Ser Gly Val Cys Thr Asp Pro Gln Pro Leu Lys
50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110
```

Arg Ala Lys Pro Val Thr Gln Ile Val Ser Ala Glu Ala Trp Gly Arg
            115                 120                 125

Ala Asp Cys Gly Ile Thr Ser Ala Ser Tyr His Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 21
<211> LENGTH: 136
<212> TYPE: PRT
<213> ORGANISM: mus musculus
<220> FEATURE:
<221> NAME/KEY: MISC_FEATURE
<223> OTHER INFORMATION: TCR alpha murC constant

<400> SEQUENCE: 21

Ile Gln Asn Pro Glu Pro Ala Val Tyr Gln Leu Lys Asp Pro Arg Ser
1               5                   10                  15

Gln Asp Ser Thr Leu Cys Leu Phe Thr Asp Phe Asp Ser Gln Ile Asn
            20                  25                  30

Val Pro Lys Thr Met Glu Ser Gly Thr Phe Ile Thr Asp Lys Thr Val
        35                  40                  45

Leu Asp Met Lys Ala Met Asp Ser Lys Ser Asn Gly Ala Ile Ala Trp
50                  55                  60

Ser Asn Gln Thr Ser Phe Thr Cys Gln Asp Ile Phe Lys Glu Thr Asn
65                  70                  75                  80

Ala Thr Tyr Pro Ser Ser Asp Val Pro Cys Asp Ala Thr Leu Thr Glu
                85                  90                  95

Lys Ser Phe Glu Thr Asp Met Asn Leu Asn Phe Gln Asn Leu Ser Val
            100                 105                 110

Met Gly Leu Arg Ile Leu Leu Leu Lys Val Ala Gly Phe Asn Leu Leu
        115                 120                 125

Met Thr Leu Arg Leu Trp Ser Ser
    130                 135

<210> SEQ ID NO 22
<211> LENGTH: 173
<212> TYPE: PRT
<213> ORGANISM: mus musculus
<220> FEATURE:
<221> NAME/KEY: MISC_feature
<223> OTHER INFORMATION: TCR beta murC constant

<400> SEQUENCE: 22

Glu Asp Leu Arg Asn Val Thr Pro Pro Lys Val Thr Leu Phe Glu Pro
1               5                   10                  15

Ser Lys Ala Glu Ile Ala Asn Lys Gln Lys Ala Thr Leu Val Cys Leu
            20                  25                  30

Ala Arg Gly Phe Phe Pro Asp His Val Glu Leu Ser Trp Trp Val Asn
        35                  40                  45

Gly Lys Glu Val His Ser Gly Val Ser Thr Asp Pro Gln Ala Tyr Lys
    50                  55                  60

Glu Ser Asn Tyr Ser Tyr Cys Leu Ser Ser Arg Leu Arg Val Ser Ala
65                  70                  75                  80

Thr Phe Trp His Asn Pro Arg Asn His Phe Arg Cys Gln Val Gln Phe
                         85                  90                  95

His Gly Leu Ser Glu Glu Asp Lys Trp Pro Glu Gly Ser Pro Lys Pro
            100                 105                 110

Val Thr Gln Asn Ile Ser Ala Glu Ala Trp Gly Arg Ala Asp Cys Gly
                115                 120                 125

Ile Thr Ser Ala Ser Tyr His Gln Gly Val Leu Ser Ala Thr Ile Leu
        130                 135                 140

Tyr Glu Ile Leu Leu Gly Lys Ala Thr Leu Tyr Ala Val Leu Val Ser
145                 150                 155                 160

Gly Leu Val Leu Met Ala Met Val Lys Lys Lys Asn Ser
                165                 170

<210> SEQ ID NO 23
<211> LENGTH: 825
<212> TYPE: DNA
<213> ORGANISM: homo sapiens
<220> FEATURE:
<221> NAME/KEY: MISC_feature
<223> OTHER INFORMATION: TCR alpha wt

<400> SEQUENCE: 23
atggagaaaa tgttggagtg tgcattcata gtcttgtggc ttcagcttgg ctggttgagt      60
ggagaagacc aggtgacgca gagtcccgag ccctgagac tccaggaggg agagagtagc     120
agtcttaact gcagttacac agtcagcggt ttaagagggc tgttctggta taggcaagat    180
cctgggaaag ccctgaatt cctcttcacc ctgtattcag ctggggaaga aaaggagaaa    240
gaaaggctaa agccacatt aacaaagaag gaaagctttc tgcacatcac agcccctaaa    300
cctgaagact cagccactta tctctgtgct gtgcactcca cagcccaggc aggaactgct    360
ctgatctttg gaagggaac caccttatca gtgagttcca atatccagaa ccctgaccct    420
gccgtgtacc agctgagaga ctctaaatcc agtgacaagt ctgtctgcct attcaccgat    480
tttgattctc aaacaaatgt gtcacaaagt aaggattctg atgtgtatat cacagacaaa    540
actgtgctag acatgaggtc tatgacttc aagagcaaca gtgctgtggc ctggagcaac    600
aaatctgact tgcatgtgc aaacgccttc aacaacagca ttattccaga agacaccttc    660
ttccccagcc agaaagttc ctgtgatgtc aagctggtcg agaaaagctt tgaaacagat    720 acgaaccta acttttcaaaa cctgtcagtg attgggttcc gaatcctcct cctgaaagtg    780
gccgggttta atctgctcat gacgctgcgg ctgtggtcca gctga                    825

<210> SEQ ID NO 24
<211> LENGTH: 936
<212> TYPE: DNA
<213> ORGANISM: homo sapiens
<220> FEATURE:
<221> NAME/KEY: MISC_feature
<223> OTHER INFORMATION: TCR beta wt

<400> SEQUENCE: 24
atgggcttca ggctcctctg ctgtgtggcc ttttgtctcc tgggagcagg cccagtggat      60
tctggagtca cacaaacccc aaagcacctg atcacagcaa ctggacagcg agtgacgctg    120
agatgctccc ctaggtctgg agacctctct gtgtactggt accaacagag cctggaccag    180
ggcctccagt tcctcattca gtattataat ggagaagaga gagcaaaagg aaacattctt    240
gaacgattct ccgcacaaca gttccctgac ttgcactctg aactaaacct gagctctctg    300
gagctggggg actcagcttt gtatttctgt gccagcagca cacacagggg gcagactaac    360

| | |
|---|---|
| tatggctaca ccttcggttc ggggaccagg ttaaccgttg tagaggacct gaacaaggtg | 420 |
| ttcccacccg aggtcgctgt gtttgagcca tcagaagcag agatctccca cacccaaaag | 480 |
| gccacactgg tgtgcctggc cacaggcttc ttccccgacc acgtggagct gagctggtgg | 540 |
| gtgaatggga aggaggtgca cagtggggtc agcacggacc cgcagcccct caaggagcag | 600 |
| cccgccctca atgactccag atactgcctg agcagccgcc tgagggtctc ggccaccttc | 660 |
| tggcagaacc cccgcaacca cttccgctgt caagtccagt tctacgggct ctcggagaat | 720 |
| gacgagtgga cccaggatag ggccaaaccc gtcacccaga tcgtcagcgc cgaggcctgg | 780 |
| ggtagagcag actgtggctt tacctcggtg tcctaccagc aaggggtcct gtctgccacc | 840 |
| atcctctatg agatcctgct agggaaggcc accctgtatg ctgtgctggt cagcgccctt | 900 |
| gtgttgatgg ccatggtcaa gagaaaggat ttctga | 936 |

<210> SEQ ID NO 25
<211> LENGTH: 825
<212> TYPE: DNA
<213> ORGANISM: artificial
<220> FEATURE:
<223> OTHER INFORMATION: TCR alpha humC codon-optimized

<400> SEQUENCE: 25

| | |
|---|---|
| atggaaaaga tgctggaatg cgccttcatc gtgctgtggc tgcagctggg atggctgagc | 60 |
| ggagaggacc aagtgaccca gtctcccgag gccctgagac tgcaggaagg cgagagcagc | 120 |
| agcctgaact gcagctacac cgtgtccggc ctgagaggcc tgttctggta cagacaggac | 180 |
| cccggcaagg gccccgagtt cctgttcaca ctgtactctg ccggcgagga aaagagaaa | 240 |
| gagcggctga aggccaccct gaccaagaaa gagagcttcc tgcacatcac cgcccccaag | 300 |
| cctgaggaca cgccacata tctgtgcgcc gtgcactcta cagcccaggc cggaaccgcc | 360 |
| ctgatctttg caagggcac caccctgagc gtgtccagca catccagaa tccggaccct | 420 |
| gccgtgtacc agctgagaga ctctaaatcc agtgacaagt ctgtctgcct attcaccgat | 480 |
| tttgattctc aaacaaatgt gtcacaaagt aaggattctg atgtgtatat cacagacaaa | 540 |
| actgtgctag acatgaggtc tatggacttc aagagcaaca gtgctgtggc ctggagcaac | 600 |
| aaatctgact ttgcatgtgc aaacgccttc aacaacagca ttattccaga agacaccttc | 660 |
| ttccccagcc cagaaagttc ctgtgatgtc aagctggtcg agaaaagctt tgaaacagat | 720 |
| acgaacctaa actttcaaaa cctgtcagtg attggttcc gaatcctcct cctgaaagtg | 780 |
| gccgggttta atctgctcat gacgctgcgg ctgtggtcca gctga | 825 |

<210> SEQ ID NO 26
<211> LENGTH: 936
<212> TYPE: DNA
<213> ORGANISM: artificial
<220> FEATURE:
<223> OTHER INFORMATION: TCR beta humC codon-optimized

<400> SEQUENCE: 26

| | |
|---|---|
| atgggcttta gactgctgtg ctgcgtggcc ttctgcctgc tgggagctgg ccctgtggat | 60 |
| agcggcgtga cccagacacc caagcacctg atcacagcca ccggccagcg cgtgaccctg | 120 |
| agatgttctc ctagaagcgg cgacctgagc gtgtactggt atcagcagag cctggaccag | 180 |
| ggcctgcagt tcctgatcca gtactacaac ggcgaggaac gggccaaggg caacatcctg | 240 |
| gaacggttca gcgcccagca gttccccgat ctgcacagcg agctgaacct gagcagcctg | 300 |
| gaactgggcg acagcgccct gtacttctgt gccagcagca cccacagagg ccagaccaac | 360 |

| | |
|---|---:|
| tacggctaca ccttcggcag cggcaccaga ctgaccgtgg tggaggacct gaacaaagtg | 420 |
| ttccccaccg aggtcgctgt gtttgagcca tcagaagcag atatctccca cacccaaaag | 480 |
| gccacactgg tgtgcctggc cacaggcttc ttccccgacc acgtggagct gagctggtgg | 540 |
| gtgaatggga aggaggtgca cagtggggtc agcacggacc cgcagcccct caaggagcag | 600 |
| cccgccctca tgactccag atactgcctg agcagccgcc tgagggtctc ggccaccttc | 660 |
| tggcagaacc cccgcaacca cttccgctgt caagtccagt tctacgggct ctcggagaat | 720 |
| gacgagtgga cccaggatag ggccaaaccc gtcacccaga tcgtcagcgc cgaggcctgg | 780 |
| ggtagagcag actgtggctt tacctcggtg tcctaccagc aaggggtcct gtctgccacc | 840 |
| atcctctatg agatcctgct agggaaggcc accctgtatg ctgtgctggt cagcgccctt | 900 |
| gtgttgatgg ccatggtcaa gagaaaggat ttctga | 936 |

<210> SEQ ID NO 27
<211> LENGTH: 825
<212> TYPE: DNA
<213> ORGANISM: artificial
<220> FEATURE:
<223> OTHER INFORMATION: TCR alpha mmcys codon-optimized

<400> SEQUENCE: 27

| | |
|---|---:|
| atggaaaaga tgctggaatg cgccttcatc gtgctgtggc tgcagctggg atggctgagc | 60 |
| ggagaggacc aagtgaccca gtctcccgag gccctgagac tgcaggaagg cgagagcagc | 120 |
| agcctgaatt gcagctacac cgtgtccggc ctgcggggcc tgttctggta tagacaggac | 180 |
| cctggcaagg gccccgagtt cctgtttacc ctgtactctg ccggcgaaga aaagaaaaa | 240 |
| gagcggctga aggccacact gaccaagaaa gagagcttcc tgcacatcac cgcccccaag | 300 |
| cctgaggaca cgccacata tctgtgcgcc gtgcactcta cagcccaggc cggaaccgcc | 360 |
| ctgatcttcg gcaagggcac aaccctgtcc gtgtccagca catccagaa ccccgacccc | 420 |
| gccgtgtacc agctgagaga cagcaagagc agcgacaaga gcgtgtgcct gttcaccgac | 480 |
| ttcgacagcc agacaaacgt gtcccagagc aaggacagcg acgtgtacat caccgataag | 540 |
| tgcgtgctgg acatgcggag catggacttc aagagcaaca gcgccgtggc ctggtccaac | 600 |
| aagagcgatt tcgcctgcgc caacgccttc aacaacagca ttatccccga ggacacattc | 660 |
| ttccccagct ccgacgtgcc ctgcgacgtg aagctggtgg aaaagagctt cgagacagac | 720 |
| accaacctga acttccagaa tctgagcgtg atcggcttca gaatcctgct gctgaaggtg | 780 |
| gccggcttca atctgctgat gaccctgcgg ctgtggtcca gctga | 825 |

<210> SEQ ID NO 28
<211> LENGTH: 935
<212> TYPE: DNA
<213> ORGANISM: artificial
<220> FEATURE:
<223> OTHER INFORMATION: TCR beta mmcys codon-optimized

<400> SEQUENCE: 28

| | |
|---|---:|
| atgggcttcc ggctgctgtg ttgcgtggcc ttctgtctgc tgggagccgg ccctgtggat | 60 |
| agcggcgtga cacagacacc caagcacctg atcaccgcca ccggcagcg cgtgacactg | 120 |
| agatgtagcc ctagaagcgg cgacctgagc gtgtactggt atcagcagag cctggaccag | 180 |
| ggcctgcagt tcctgatcca gtactacaac ggcgaggaac gggccaaggg caacatcctg | 240 |
| gaacggttca gcgcccagca gttccccgat ctgcacagcg agctgaacct gagcagcctg | 300 |
| gaactgggcg acagcgccct gtacttctgt gccagcagca cccacagagg ccagaccaac | 360 |

| | |
|---|---|
| tacggctaca ccttcggcag cggcaccaga ctgaccgtgg tggaagatct gaacaaggtg | 420 |
| ttcccccag aggtggccgt gttcgagcct agcaaggccg agatcgccca cacccagaaa | 480 |
| gccaccctcg tgtgtctggc caccggcttt ttccccgacc acgtggaact gtcttggtgg | 540 |
| gtcaacggca agaggtgca ctccggcgtg tgcaccgatc cccagcctct gaaagaacag | 600 |
| cccgccctga cgacagccg gtactgcctg ccagcagac tgagagtgtc cgccaccttc | 660 |
| tggcagaacc cccggaacca cttcagatgc caggtgcagt tctacggcct gagcgagaac | 720 |
| gacgagtgga cccaggacag agccaagccc gtgacccaga tcgtgtctgc cgaagcctgg | 780 |
| ggcagagccg attgtggcat caccagcgcc agctaccatc agggcgtgct gagcgccacc | 840 |
| atcctgtacg agatcctgct gggcaaggcc accctgtacg ccgtgctggt gtctgccctg | 900 |
| gtgctgatgg ccatggtcaa gcggaaggac tttga | 935 |

<210> SEQ ID NO 29
<211> LENGTH: 813
<212> TYPE: DNA
<213> ORGANISM: artificial
<220> FEATURE:
<223> OTHER INFORMATION: TCR alpha murC codon-optimized

<400> SEQUENCE: 29

| | |
|---|---|
| atggaaaaga tgctggaatg cgccttcatc gtgctgtggc tgcagctggg atggctgagc | 60 |
| ggagaggacc aagtgaccca gtctcccgag ccctgagact gcaggaagg cgagagcagc | 120 |
| agcctgaact gcagctacac cgtgtccggc ctgagaggcc tgttctggta cagacaggac | 180 |
| cccgcaagg gccccgagtt cctgttcaca ctgtactctg ccggcgagga aaagagaaa | 240 |
| gagcggctga aggccaccct gaccaagaaa gagagcttcc tgcacatcac cgcccccaag | 300 |
| cctgaggaca cgccacata tctgtgcgcc gtgcactcta cagcccaggc cggaaccgcc | 360 |
| ctgatctttg caagggcac caccctgagc gtgtccagca acatccagaa ccccgagccc | 420 |
| gccgtgtacc agctgaagga ccctagaagc caggacagca ccctgtgcct gttcaccgac | 480 |
| ttcgacagcc agatcaacgt gcccaagacc atggaaagcg gcaccttcat caccgacaag | 540 |
| acagtgctgg acatgaaggc catggacagc aagagcaacg gcgccattgc ctggtccaac | 600 |
| cagaccagct tcacatgcca ggacatcttc aaagagacaa acgccaccta ccccagcagc | 660 |
| gacgtgccct gcgacgccac cctgaccgag aagagcttcg agacagacat gaacctgaat | 720 |
| ttccagaacc tgagcgtgat gggcctgcgg atcctgctgc tgaaggtggc cggcttcaac | 780 |
| ctgctgatga ccctgcggct gtggagcagc tga | 813 |

<210> SEQ ID NO 30
<211> LENGTH: 924
<212> TYPE: DNA
<213> ORGANISM: artificial
<220> FEATURE:
<223> OTHER INFORMATION: TCR beta murC codon-optimized

<400> SEQUENCE: 30

| | |
|---|---|
| atgggcttta gactgctgtg ctgcgtggcc ttctgcctgc tgggagctgg ccctgtggat | 60 |
| agcggcgtga cccagacacc caagcacctg atcacagcca ccggccagcg cgtgaccctg | 120 |
| agatgttctc ctagaagcgg cgacctgagc gtgtactggt atcagcagag cctggaccag | 180 |
| ggcctgcagt tcctgatcca gtactacaac ggcgaggaac gggccaaggg caacatcctg | 240 |
| gaacggttca gcgcccagca gttccccgat ctgcacagcg agctgaacct gagcagcctg | 300 |
| gaactgggcg acagcgccct gtacttctgt gccagcagca cccacagagg ccagaccaac | 360 |

-continued

```
tacggctaca ccttcggcag cggcaccaga ctgaccgtgg tggaagatct gcggaacgtg    420 accccccca aggtgaccct gttcgagccc agcaaggccg agatcgccaa caagcagaaa     480
gccaccctgg tctgcctggc caggggcttc ttccccgacc acgtggagct gtcttggtgg    540
gtgaacggca agaggtgca cagcggagtc agtaccgacc cccaggccta caaagagagc     600
aactacagct actgcctgag cagcaggctg agagtgagcg ccaccttctg cacaacccc     660 cggaaccact tccggtgcca ggtgcagttc cacggcctga gcgaagagga caagtggcct    720
gagggcagcc ccaagcccgt gacccagaac atcagcgccg aggcctgggg cagagccgac    780
tgcggcatca ccagcgccag ctaccaccag ggcgtgctgt ccgccaccat cctgtacgag    840
atcctgctgg gcaaggccac cctgtacgcc gtgctggtgt ccggcctggt gctgatggcc    900
atggtgaaga agaagaacag ctga                                          924
```

```
<210> SEQ ID NO 31
<211> LENGTH: 9
<212> TYPE: PRT
<213> ORGANISM: artificial
<220> FEATURE:
<223> OTHER INFORMATION: MINIMAL RECOGNITION SEQUENCE
<220> FEATURE:
<221> NAME/KEY: MISC_FEATURE
<222> LOCATION: (1)..(1)
<223> OTHER INFORMATION: X can be selected from any amino acid
<220> FEATURE:
<221> NAME/KEY: MISC_FEATURE
<222> LOCATION: (3)..(3)
<223> OTHER INFORMATION: X can be selected from any amino acid
<220> FEATURE:
<221> NAME/KEY: MISC_FEATURE
<222> LOCATION: (7)..(7)
<223> OTHER INFORMATION: X can be selected from any amino acid

<400> SEQUENCE: 31

Xaa Leu Xaa Gly Leu Asp Xaa Leu Leu
1               5

<210> SEQ ID NO 32
<211> LENGTH: 9
<212> TYPE: PRT
<213> ORGANISM: homo sapiens

<400> SEQUENCE: 32

Val Leu Asp Gly Leu Asp Val Leu Leu
1               5

<210> SEQ ID NO 33
<211> LENGTH: 509
<212> TYPE: PRT
<213> ORGANISM: homo sapiens

<400> SEQUENCE: 33

Met Glu Arg Arg Arg Leu Trp Gly Ser Ile Gln Ser Arg Tyr Ile Ser
1               5                   10                  15

Met Ser Val Trp Thr Ser Pro Arg Arg Leu Val Glu Leu Ala Gly Gln
                20                  25                  30

Ser Leu Leu Lys Asp Glu Ala Leu Ala Ile Ala Ala Leu Glu Leu Leu
            35                  40                  45

Pro Arg Glu Leu Phe Pro Pro Leu Phe Met Ala Ala Phe Asp Gly Arg
        50                  55                  60

His Ser Gln Thr Leu Lys Ala Met Val Gln Ala Trp Pro Phe Thr Cys
65                  70                  75                  80
```

```
Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
            100                 105                 110

Arg Pro Arg Arg Trp Lys Leu Gln Val Leu Asp Leu Arg Lys Asn Ser
        115                 120                 125

His Gln Asp Phe Trp Thr Val Trp Ser Gly Asn Arg Ala Ser Leu Tyr
    130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Lys Asn Val Leu Arg Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255

Gly Gln Met Ile Asn Leu Arg Arg Leu Leu Leu Ser His Ile His Ala
            260                 265                 270

Ser Ser Tyr Ile Ser Pro Glu Lys Glu Gln Tyr Ile Ala Gln Phe
        275                 280                 285

Thr Ser Gln Phe Leu Ser Leu Gln Cys Leu Gln Ala Leu Tyr Val Asp
    290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
        355                 360                 365

Leu Gln Ala Leu Leu Glu Arg Ala Ser Ala Thr Leu Gln Asp Leu Val
    370                 375                 380

Phe Asp Glu Cys Gly Ile Thr Asp Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
            420                 425                 430

Leu Ser Asn Leu Thr His Val Leu Tyr Pro Val Pro Leu Glu Ser Tyr
        435                 440                 445

Glu Asp Ile His Gly Thr Leu His Leu Glu Arg Leu Ala Tyr Leu His
    450                 455                 460

Ala Arg Leu Arg Glu Leu Leu Cys Glu Leu Gly Arg Pro Ser Met Val
465                 470                 475                 480
```

Trp Leu Ser Ala Asn Pro Cys Pro His Cys Gly Asp Arg Thr Phe Tyr
            485                 490                 495

Asp Pro Glu Pro Ile Leu Cys Pro Cys Phe Met Pro Asn
        500                 505

<210> SEQ ID NO 34
<211> LENGTH: 6
<212> TYPE: PRT
<213> ORGANISM: Homo sapiens

<400> SEQUENCE: 34

Thr Ser Gly Phe Tyr Gly
1               5

<210> SEQ ID NO 35
<211> LENGTH: 6
<212> TYPE: PRT
<213> ORGANISM: Homo sapiens

<400> SEQUENCE: 35

Thr Ser Gly Phe Asn Gly
1               5

<210> SEQ ID NO 36
<211> LENGTH: 6
<212> TYPE: PRT
<213> ORGANISM: Homo sapiens

<400> SEQUENCE: 36

Val Ser Asn Ala Tyr Asn
1               5

<210> SEQ ID NO 37
<211> LENGTH: 6
<212> TYPE: PRT
<213> ORGANISM: Homo sapiens

<400> SEQUENCE: 37

Val Ser Gly Asn Pro Tyr
1               5

<210> SEQ ID NO 38
<211> LENGTH: 7
<212> TYPE: PRT
<213> ORGANISM: Homo sapiens

<400> SEQUENCE: 38

Asn Ile Ala Thr Asn Asp Tyr
1               5

<210> SEQ ID NO 39
<211> LENGTH: 6
<212> TYPE: PRT
<213> ORGANISM: Homo sapiens

<400> SEQUENCE: 39

Asp Ser Ser Ser Thr Tyr
1               5

<210> SEQ ID NO 40
<211> LENGTH: 6
<212> TYPE: PRT
<213> ORGANISM: Homo sapiens

```
<400> SEQUENCE: 40

Asn Tyr Ser Pro Ala Tyr
1               5

<210> SEQ ID NO 41
<211> LENGTH: 6
<212> TYPE: PRT
<213> ORGANISM: Homo sapiens

<400> SEQUENCE: 41

Val Ser Arg Phe Asn Asn
1               5

<210> SEQ ID NO 42
<211> LENGTH: 6
<212> TYPE: PRT
<213> ORGANISM: Homo sapiens

<400> SEQUENCE: 42

Tyr Gly Gly Thr Val Asn
1               5

<210> SEQ ID NO 43
<211> LENGTH: 6
<212> TYPE: PRT
<213> ORGANISM: Homo sapiens

<400> SEQUENCE: 43

Ser Ser Tyr Ser Pro Ser
1               5

<210> SEQ ID NO 44
<211> LENGTH: 6
<212> TYPE: PRT
<213> ORGANISM: Homo sapiens

<400> SEQUENCE: 44

Tyr Gly Ala Thr Pro Tyr
1               5

<210> SEQ ID NO 45
<211> LENGTH: 6
<212> TYPE: PRT
<213> ORGANISM: Homo sapiens

<400> SEQUENCE: 45

Ser Ser Val Pro Pro Tyr
1               5

<210> SEQ ID NO 46
<211> LENGTH: 6
<212> TYPE: PRT
<213> ORGANISM: Homo sapiens

<400> SEQUENCE: 46

Ser Ser Val Ser Val Tyr
1               5

<210> SEQ ID NO 47
<211> LENGTH: 6
<212> TYPE: PRT
<213> ORGANISM: Homo sapiens
```

```
<400> SEQUENCE: 47

Thr Thr Gln Tyr Pro Ser
1               5

<210> SEQ ID NO 48
<211> LENGTH: 6
<212> TYPE: PRT
<213> ORGANISM: Homo sapiens

<400> SEQUENCE: 48

Ala Thr Gly Tyr Pro Ser
1               5

<210> SEQ ID NO 49
<211> LENGTH: 6
<212> TYPE: PRT
<213> ORGANISM: Homo sapiens

<400> SEQUENCE: 49

Val Ser Pro Phe Ser Asn
1               5

<210> SEQ ID NO 50
<211> LENGTH: 6
<212> TYPE: PRT
<213> ORGANISM: Homo sapiens

<400> SEQUENCE: 50

Glu Arg Thr Leu Phe Asn
1               5

<210> SEQ ID NO 51
<211> LENGTH: 6
<212> TYPE: PRT
<213> ORGANISM: Homo sapiens

<400> SEQUENCE: 51

Asn Ser Ala Ser Gln Ser
1               5

<210> SEQ ID NO 52
<211> LENGTH: 6
<212> TYPE: PRT
<213> ORGANISM: Homo sapiens

<400> SEQUENCE: 52

Asp Arg Gly Ser Gln Ser
1               5

<210> SEQ ID NO 53
<211> LENGTH: 6
<212> TYPE: PRT
<213> ORGANISM: Homo sapiens

<400> SEQUENCE: 53

Asn Ser Ala Phe Gln Tyr
1               5

<210> SEQ ID NO 54
<211> LENGTH: 6
<212> TYPE: PRT
<213> ORGANISM: Homo sapiens
```

```
<400> SEQUENCE: 54

Asp Ser Ala Ser Asn Tyr
1               5

<210> SEQ ID NO 55
<211> LENGTH: 6
<212> TYPE: PRT
<213> ORGANISM: Homo sapiens

<400> SEQUENCE: 55

Asn Ser Ala Ser Asp Tyr
1               5

<210> SEQ ID NO 56
<211> LENGTH: 7
<212> TYPE: PRT
<213> ORGANISM: Homo sapiens

<400> SEQUENCE: 56

Thr Ser Asp Pro Ser Tyr Gly
1               5

<210> SEQ ID NO 57
<211> LENGTH: 6
<212> TYPE: PRT
<213> ORGANISM: Homo sapiens

<400> SEQUENCE: 57

Tyr Ser Gly Ser Pro Glu
1               5

<210> SEQ ID NO 58
<211> LENGTH: 5
<212> TYPE: PRT
<213> ORGANISM: Homo sapiens

<400> SEQUENCE: 58

Thr Ser Ile Asn Asn
1               5

<210> SEQ ID NO 59
<211> LENGTH: 6
<212> TYPE: PRT
<213> ORGANISM: Homo sapiens

<400> SEQUENCE: 59

Ser Ser Tyr Ser Thr Phe
1               5

<210> SEQ ID NO 60
<211> LENGTH: 7
<212> TYPE: PRT
<213> ORGANISM: Homo sapiens

<400> SEQUENCE: 60

Thr Arg Asp Thr Thr Tyr Tyr
1               5

<210> SEQ ID NO 61
<211> LENGTH: 6
<212> TYPE: PRT
<213> ORGANISM: Homo sapiens
```

```
<400> SEQUENCE: 61

Val Ser Gly Leu Arg Gly
1               5

<210> SEQ ID NO 62
<211> LENGTH: 6
<212> TYPE: PRT
<213> ORGANISM: Homo sapiens

<400> SEQUENCE: 62

Asp Ser Ala Ile Tyr Asn
1               5

<210> SEQ ID NO 63
<211> LENGTH: 5
<212> TYPE: PRT
<213> ORGANISM: Homo sapiens

<400> SEQUENCE: 63

Asp Ser Val Asn Asn
1               5

<210> SEQ ID NO 64
<211> LENGTH: 6
<212> TYPE: PRT
<213> ORGANISM: Homo sapiens

<400> SEQUENCE: 64

Asn Thr Ala Phe Asp Tyr
1               5

<210> SEQ ID NO 65
<211> LENGTH: 6
<212> TYPE: PRT
<213> ORGANISM: Homo sapiens

<400> SEQUENCE: 65

Ser Ser Asn Phe Tyr Ala
1               5

<210> SEQ ID NO 66
<211> LENGTH: 5
<212> TYPE: PRT
<213> ORGANISM: Homo sapiens

<400> SEQUENCE: 66

Thr Thr Leu Ser Asn
1               5

<210> SEQ ID NO 67
<211> LENGTH: 7
<212> TYPE: PRT
<213> ORGANISM: Homo sapiens

<400> SEQUENCE: 67

Thr Ile Ser Gly Asn Glu Tyr
1               5

<210> SEQ ID NO 68
<211> LENGTH: 7
<212> TYPE: PRT
<213> ORGANISM: Homo sapiens
```

```
<400> SEQUENCE: 68

Thr Ile Ser Gly Thr Asp Tyr
1               5

<210> SEQ ID NO 69
<211> LENGTH: 5
<212> TYPE: PRT
<213> ORGANISM: Homo sapiens

<400> SEQUENCE: 69

Ser Val Phe Ser Ser
1               5

<210> SEQ ID NO 70
<211> LENGTH: 6
<212> TYPE: PRT
<213> ORGANISM: Homo sapiens

<400> SEQUENCE: 70

Asn Ser Met Phe Asp Tyr
1               5

<210> SEQ ID NO 71
<211> LENGTH: 5
<212> TYPE: PRT
<213> ORGANISM: Homo sapiens

<400> SEQUENCE: 71

Lys Ala Leu Tyr Ser
1               5

<210> SEQ ID NO 72
<211> LENGTH: 5
<212> TYPE: PRT
<213> ORGANISM: Homo sapiens

<400> SEQUENCE: 72

Lys Thr Leu Tyr Gly
1               5

<210> SEQ ID NO 73
<211> LENGTH: 5
<212> TYPE: PRT
<213> ORGANISM: Homo sapiens

<400> SEQUENCE: 73

Ser Ile Phe Asn Thr
1               5

<210> SEQ ID NO 74
<211> LENGTH: 6
<212> TYPE: PRT
<213> ORGANISM: Homo sapiens

<400> SEQUENCE: 74

Val Thr Asn Phe Arg Ser
1               5

<210> SEQ ID NO 75
<211> LENGTH: 7
<212> TYPE: PRT
<213> ORGANISM: Homo sapiens
```

```
<400> SEQUENCE: 75

Thr Ser Glu Asn Asn Tyr Tyr
1               5

<210> SEQ ID NO 76
<211> LENGTH: 7
<212> TYPE: PRT
<213> ORGANISM: Homo sapiens

<400> SEQUENCE: 76

Thr Ser Glu Ser Asp Tyr Tyr
1               5

<210> SEQ ID NO 77
<211> LENGTH: 5
<212> TYPE: PRT
<213> ORGANISM: Homo sapiens

<400> SEQUENCE: 77

Thr Thr Ser Asp Arg
1               5

<210> SEQ ID NO 78
<211> LENGTH: 6
<212> TYPE: PRT
<213> ORGANISM: Homo sapiens

<400> SEQUENCE: 78

Ser Thr Gly Tyr Pro Thr
1               5

<210> SEQ ID NO 79
<211> LENGTH: 5
<212> TYPE: PRT
<213> ORGANISM: Homo sapiens

<400> SEQUENCE: 79

Val Gly Ile Ser Ala
1               5

<210> SEQ ID NO 80
<211> LENGTH: 5
<212> TYPE: PRT
<213> ORGANISM: Homo sapiens

<400> SEQUENCE: 80

Ser Asn His Leu Tyr
1               5

<210> SEQ ID NO 81
<211> LENGTH: 5
<212> TYPE: PRT
<213> ORGANISM: Homo sapiens

<400> SEQUENCE: 81

Leu Gly His Asp Thr
1               5

<210> SEQ ID NO 82
<211> LENGTH: 5
<212> TYPE: PRT
<213> ORGANISM: Homo sapiens
```

```
<400> SEQUENCE: 82

Met Gly His Arg Ala
1               5

<210> SEQ ID NO 83
<211> LENGTH: 5
<212> TYPE: PRT
<213> ORGANISM: Homo sapiens

<400> SEQUENCE: 83

Leu Gly His Asn Ala
1               5

<210> SEQ ID NO 84
<211> LENGTH: 5
<212> TYPE: PRT
<213> ORGANISM: Homo sapiens

<400> SEQUENCE: 84

Leu Gly His Asn Ala
1               5

<210> SEQ ID NO 85
<211> LENGTH: 5
<212> TYPE: PRT
<213> ORGANISM: Homo sapiens

<400> SEQUENCE: 85

Ser Gly His Arg Ser
1               5

<210> SEQ ID NO 86
<211> LENGTH: 5
<212> TYPE: PRT
<213> ORGANISM: homo sapiens

<400> SEQUENCE: 86

Ser Gly His Asn Thr
1               5

<210> SEQ ID NO 87
<211> LENGTH: 5
<212> TYPE: PRT
<213> ORGANISM: Homo sapiens

<400> SEQUENCE: 87

Ser Gly His Lys Ser
1               5

<210> SEQ ID NO 88
<211> LENGTH: 5
<212> TYPE: PRT
<213> ORGANISM: Homo sapiens

<400> SEQUENCE: 88

Ser Gly His Asp Thr
1               5

<210> SEQ ID NO 89
<211> LENGTH: 5
<212> TYPE: PRT
<213> ORGANISM: Homo sapiens
```

<400> SEQUENCE: 89

Ser Gly His Thr Ser
1               5

<210> SEQ ID NO 90
<211> LENGTH: 5
<212> TYPE: PRT
<213> ORGANISM: homo sapiens

<400> SEQUENCE: 90

Met Asn His Asn Ser
1               5

<210> SEQ ID NO 91
<211> LENGTH: 5
<212> TYPE: PRT
<213> ORGANISM: Homo sapiens

<400> SEQUENCE: 91

Met Asn His Glu Tyr
1               5

<210> SEQ ID NO 92
<211> LENGTH: 5
<212> TYPE: PRT
<213> ORGANISM: Homo sapiens

<400> SEQUENCE: 92

Met Asn His Glu Tyr
1               5

<210> SEQ ID NO 93
<211> LENGTH: 5
<212> TYPE: PRT
<213> ORGANISM: homo sapiens

<400> SEQUENCE: 93

Met Arg His Asn Ala
1               5

<210> SEQ ID NO 94
<211> LENGTH: 5
<212> TYPE: PRT
<213> ORGANISM: Homo sapiens

<400> SEQUENCE: 94

Met Asn His Glu Tyr
1               5

<210> SEQ ID NO 95
<211> LENGTH: 5
<212> TYPE: PRT
<213> ORGANISM: Homo sapiens

<400> SEQUENCE: 95

Met Asn His Asn Tyr
1               5

<210> SEQ ID NO 96
<211> LENGTH: 5
<212> TYPE: PRT
<213> ORGANISM: Homo sapiens

<400> SEQUENCE: 96

Met Asn His Gly Tyr
1               5

<210> SEQ ID NO 97
<211> LENGTH: 5
<212> TYPE: PRT
<213> ORGANISM: Homo sapiens

<400> SEQUENCE: 97

Met Asn His Gly Tyr
1               5

<210> SEQ ID NO 98
<211> LENGTH: 5
<212> TYPE: PRT
<213> ORGANISM: Homo sapiens

<400> SEQUENCE: 98

Ser Gly His Thr Ala
1               5

<210> SEQ ID NO 99
<211> LENGTH: 5
<212> TYPE: PRT
<213> ORGANISM: Homo sapiens

<400> SEQUENCE: 99

Ser Gly His Thr Ala
1               5

<210> SEQ ID NO 100
<211> LENGTH: 5
<212> TYPE: PRT
<213> ORGANISM: Homo sapiens

<400> SEQUENCE: 100

Ser Gly His Val Thr
1               5

<210> SEQ ID NO 101
<211> LENGTH: 5
<212> TYPE: PRT
<213> ORGANISM: Homo sapiens

<400> SEQUENCE: 101

Ser Gly His Val Ser
1               5

<210> SEQ ID NO 102
<211> LENGTH: 5
<212> TYPE: PRT
<213> ORGANISM: Homo sapiens

<400> SEQUENCE: 102

Ser Ser His Ala Thr
1               5

<210> SEQ ID NO 103
<211> LENGTH: 5
<212> TYPE: PRT
<213> ORGANISM: Homo sapiens

```
<400> SEQUENCE: 103

Ser Gly His Val Ser
1               5

<210> SEQ ID NO 104
<211> LENGTH: 5
<212> TYPE: PRT
<213> ORGANISM: Homo sapiens

<400> SEQUENCE: 104

Ser Glu His Asn Arg
1               5

<210> SEQ ID NO 105
<211> LENGTH: 5
<212> TYPE: PRT
<213> ORGANISM: Homo sapiens

<400> SEQUENCE: 105

Ser Gly Asp Leu Ser
1               5

<210> SEQ ID NO 106
<211> LENGTH: 5
<212> TYPE: PRT
<213> ORGANISM: Homo sapiens

<400> SEQUENCE: 106

Trp Asn His Asn Asn
1               5

<210> SEQ ID NO 107
<211> LENGTH: 5
<212> TYPE: PRT
<213> ORGANISM: Homo sapiens

<400> SEQUENCE: 107

Trp Ser His Ser Tyr
1               5

<210> SEQ ID NO 108
<211> LENGTH: 5
<212> TYPE: PRT
<213> ORGANISM: Homo sapiens

<400> SEQUENCE: 108

Glu Asn His Arg Tyr
1               5

<210> SEQ ID NO 109
<211> LENGTH: 5
<212> TYPE: PRT
<213> ORGANISM: Homo sapiens

<400> SEQUENCE: 109

Ser Gly His Ala Thr
1               5

<210> SEQ ID NO 110
<211> LENGTH: 5
<212> TYPE: PRT
<213> ORGANISM: Homo sapiens
```

```
<400> SEQUENCE: 110

Ser Gly His Ala Thr
1               5

<210> SEQ ID NO 111
<211> LENGTH: 5
<212> TYPE: PRT
<213> ORGANISM: Homo sapiens

<400> SEQUENCE: 111

Ser Gly His Asn Thr
1               5

<210> SEQ ID NO 112
<211> LENGTH: 5
<212> TYPE: PRT
<213> ORGANISM: Homo sapiens

<400> SEQUENCE: 112

Ser Gly His Asn Asp
1               5

<210> SEQ ID NO 113
<211> LENGTH: 5
<212> TYPE: PRT
<213> ORGANISM: Homo sapiens

<400> SEQUENCE: 113

Phe Gly His Asn Phe
1               5

<210> SEQ ID NO 114
<211> LENGTH: 5
<212> TYPE: PRT
<213> ORGANISM: Homo sapiens

<400> SEQUENCE: 114

Ser Gly His Asn Ser
1               5

<210> SEQ ID NO 115
<211> LENGTH: 5
<212> TYPE: PRT
<213> ORGANISM: Homo sapiens

<400> SEQUENCE: 115

Ser Gly His Asp Tyr
1               5

<210> SEQ ID NO 116
<211> LENGTH: 5
<212> TYPE: PRT
<213> ORGANISM: Homo sapiens

<400> SEQUENCE: 116

Leu Gly His Asn Thr
1               5

<210> SEQ ID NO 117
<211> LENGTH: 5
<212> TYPE: PRT
<213> ORGANISM: Homo sapiens
```

```
<400> SEQUENCE: 117

Pro Arg His Asp Thr
1               5

<210> SEQ ID NO 118
<211> LENGTH: 5
<212> TYPE: PRT
<213> ORGANISM: Homo sapiens

<400> SEQUENCE: 118

Ser Gly His Asp Asn
1               5

<210> SEQ ID NO 119
<211> LENGTH: 5
<212> TYPE: PRT
<213> ORGANISM: Homo sapiens

<400> SEQUENCE: 119

Leu Asn His Asn Val
1               5

<210> SEQ ID NO 120
<211> LENGTH: 5
<212> TYPE: PRT
<213> ORGANISM: Homo sapiens

<400> SEQUENCE: 120

Lys Gly His Ser Tyr
1               5

<210> SEQ ID NO 121
<211> LENGTH: 5
<212> TYPE: PRT
<213> ORGANISM: Homo sapiens

<400> SEQUENCE: 121

Lys Gly His Ser His
1               5

<210> SEQ ID NO 122
<211> LENGTH: 5
<212> TYPE: PRT
<213> ORGANISM: Homo sapiens

<400> SEQUENCE: 122

Leu Asn His Asp Ala
1               5

<210> SEQ ID NO 123
<211> LENGTH: 6
<212> TYPE: PRT
<213> ORGANISM: Homo sapiens

<400> SEQUENCE: 123

Asp Phe Gln Ala Thr Thr
1               5

<210> SEQ ID NO 124
<211> LENGTH: 5
<212> TYPE: PRT
<213> ORGANISM: homo sapiens
```

```
<400> SEQUENCE: 124

Lys Gly His Asp Arg
1               5

<210> SEQ ID NO 125
<211> LENGTH: 5
<212> TYPE: PRT
<213> ORGANISM: Homo sapiens

<400> SEQUENCE: 125

Met Gly His Asp Lys
1               5

<210> SEQ ID NO 126
<211> LENGTH: 5
<212> TYPE: PRT
<213> ORGANISM: Homo sapiens

<400> SEQUENCE: 126

Met Asn His Glu Tyr
1               5

<210> SEQ ID NO 127
<211> LENGTH: 5
<212> TYPE: PRT
<213> ORGANISM: Homo sapiens

<400> SEQUENCE: 127

Met Asp His Glu Asn
1               5

<210> SEQ ID NO 128
<211> LENGTH: 5
<212> TYPE: PRT
<213> ORGANISM: Homo sapiens

<400> SEQUENCE: 128

Ser Gln Val Thr Met
1               5

<210> SEQ ID NO 129
<211> LENGTH: 6
<212> TYPE: PRT
<213> ORGANISM: Homo sapiens

<400> SEQUENCE: 129

Gly Thr Ser Asn Pro Asn
1               5

<210> SEQ ID NO 130
<211> LENGTH: 6
<212> TYPE: PRT
<213> ORGANISM: Homo sapiens

<400> SEQUENCE: 130

Asn Ala Leu Asp Gly Leu
1               5

<210> SEQ ID NO 131
<211> LENGTH: 6
<212> TYPE: PRT
<213> ORGANISM: Homo sapiens
```

```
<400> SEQUENCE: 131

Asn Val Leu Asp Gly Leu
1               5

<210> SEQ ID NO 132
<211> LENGTH: 4
<212> TYPE: PRT
<213> ORGANISM: Homo sapiens

<400> SEQUENCE: 132

Gly Ser Lys Pro
1

<210> SEQ ID NO 133
<211> LENGTH: 8
<212> TYPE: PRT
<213> ORGANISM: Homo sapiens

<400> SEQUENCE: 133

Tyr Ile Thr Gly Asp Asn Leu Val
1               5

<210> SEQ ID NO 134
<211> LENGTH: 5
<212> TYPE: PRT
<213> ORGANISM: Homo sapiens

<400> SEQUENCE: 134

Gly Tyr Lys Thr Lys
1               5

<210> SEQ ID NO 135
<211> LENGTH: 7
<212> TYPE: PRT
<213> ORGANISM: homo sapiens

<400> SEQUENCE: 135

Ile Phe Ser Asn Met Asp Met
1               5

<210> SEQ ID NO 136
<211> LENGTH: 7
<212> TYPE: PRT
<213> ORGANISM: Homo sapiens

<400> SEQUENCE: 136

Ile Arg Glu Asn Glu Lys Glu
1               5

<210> SEQ ID NO 137
<211> LENGTH: 7
<212> TYPE: PRT
<213> ORGANISM: Homo sapiens

<400> SEQUENCE: 137

Met Tyr Ser Ala Gly Tyr Glu
1               5

<210> SEQ ID NO 138
<211> LENGTH: 8
<212> TYPE: PRT
<213> ORGANISM: Homo sapiens
```

```
<400> SEQUENCE: 138

Tyr Phe Ser Gly Asp Pro Leu Val
1               5

<210> SEQ ID NO 139
<211> LENGTH: 8
<212> TYPE: PRT
<213> ORGANISM: Homo sapiens

<400> SEQUENCE: 139

Tyr Thr Ser Ala Ala Thr Leu Val
1               5

<210> SEQ ID NO 140
<211> LENGTH: 8
<212> TYPE: PRT
<213> ORGANISM: Homo sapiens

<400> SEQUENCE: 140

Tyr Phe Ser Gly Asp Thr Leu Val
1               5

<210> SEQ ID NO 141
<211> LENGTH: 8
<212> TYPE: PRT
<213> ORGANISM: Homo sapiens

<400> SEQUENCE: 141

Tyr Thr Ser Ala Ala Thr Leu Val
1               5

<210> SEQ ID NO 142
<211> LENGTH: 8
<212> TYPE: PRT
<213> ORGANISM: Homo sapiens

<400> SEQUENCE: 142

Tyr Leu Ser Gly Ser Thr Leu Val
1               5

<210> SEQ ID NO 143
<211> LENGTH: 7
<212> TYPE: PRT
<213> ORGANISM: Homo sapiens

<400> SEQUENCE: 143

Ala Met Lys Ala Asn Asp Lys
1               5

<210> SEQ ID NO 144
<211> LENGTH: 7
<212> TYPE: PRT
<213> ORGANISM: Homo sapiens

<400> SEQUENCE: 144

Ala Thr Lys Ala Asp Asp Lys
1               5

<210> SEQ ID NO 145
<211> LENGTH: 7
<212> TYPE: PRT
<213> ORGANISM: Homo sapiens
```

```
<400> SEQUENCE: 145

Met Thr Phe Ser Glu Asn Thr
1               5

<210> SEQ ID NO 146
<211> LENGTH: 7
<212> TYPE: PRT
<213> ORGANISM: Homo sapiens

<400> SEQUENCE: 146

Ile Gln Ser Ser Gln Lys Glu
1               5

<210> SEQ ID NO 147
<211> LENGTH: 6
<212> TYPE: PRT
<213> ORGANISM: Homo sapiens

<400> SEQUENCE: 147

Val Tyr Ser Ser Gly Asn
1               5

<210> SEQ ID NO 148
<211> LENGTH: 6
<212> TYPE: PRT
<213> ORGANISM: Homo sapiens

<400> SEQUENCE: 148

Ile Tyr Ser Asn Gly Asp
1               5

<210> SEQ ID NO 149
<211> LENGTH: 6
<212> TYPE: PRT
<213> ORGANISM: Homo sapiens

<400> SEQUENCE: 149

Thr Tyr Ser Ser Gly Asn
1               5

<210> SEQ ID NO 150
<211> LENGTH: 7
<212> TYPE: PRT
<213> ORGANISM: Homo sapiens

<400> SEQUENCE: 150

Ile Arg Ser Asn Val Gly Glu
1               5

<210> SEQ ID NO 151
<211> LENGTH: 7
<212> TYPE: PRT
<213> ORGANISM: Homo sapiens

<400> SEQUENCE: 151

Ile Arg Ser Asn Met Asp Lys
1               5

<210> SEQ ID NO 152
<211> LENGTH: 8
<212> TYPE: PRT
<213> ORGANISM: Homo sapiens
```

```
<400> SEQUENCE: 152

Gln Gly Ser Tyr Asp Gln Gln Asn
1               5

<210> SEQ ID NO 153
<211> LENGTH: 4
<212> TYPE: PRT
<213> ORGANISM: Homo sapiens

<400> SEQUENCE: 153

His Ile Ser Arg
1

<210> SEQ ID NO 154
<211> LENGTH: 7
<212> TYPE: PRT
<213> ORGANISM: Homo sapiens

<400> SEQUENCE: 154

Ile Arg Ser Asn Glu Arg Glu
1               5

<210> SEQ ID NO 155
<211> LENGTH: 6
<212> TYPE: PRT
<213> ORGANISM: Homo sapiens

<400> SEQUENCE: 155

Ser Ser Glu Asn Gln Glu
1               5

<210> SEQ ID NO 156
<211> LENGTH: 8
<212> TYPE: PRT
<213> ORGANISM: Homo sapiens

<400> SEQUENCE: 156

Arg Asn Ser Phe Asp Glu Gln Asn
1               5

<210> SEQ ID NO 157
<211> LENGTH: 7
<212> TYPE: PRT
<213> ORGANISM: Homo sapiens

<400> SEQUENCE: 157

Leu Tyr Ser Ala Gly Glu Glu
1               5

<210> SEQ ID NO 158
<211> LENGTH: 7
<212> TYPE: PRT
<213> ORGANISM: Homo sapiens

<400> SEQUENCE: 158

Ile Gln Ser Ser Gln Arg Glu
1               5

<210> SEQ ID NO 159
<211> LENGTH: 5
<212> TYPE: PRT
<213> ORGANISM: Homo sapiens
```

```
<400> SEQUENCE: 159

Ile Pro Ser Gly Thr
1               5

<210> SEQ ID NO 160
<211> LENGTH: 7
<212> TYPE: PRT
<213> ORGANISM: homo sapiens

<400> SEQUENCE: 160

Ile Arg Pro Asp Val Ser Glu
1               5

<210> SEQ ID NO 161
<211> LENGTH: 7
<212> TYPE: PRT
<213> ORGANISM: Homo sapiens

<400> SEQUENCE: 161

Met Thr Leu Asn Gly Asp Glu
1               5

<210> SEQ ID NO 162
<211> LENGTH: 7
<212> TYPE: PRT
<213> ORGANISM: Homo sapiens

<400> SEQUENCE: 162

Leu Val Lys Ser Gly Glu Val
1               5

<210> SEQ ID NO 163
<211> LENGTH: 5
<212> TYPE: PRT
<213> ORGANISM: Homo sapiens

<400> SEQUENCE: 163

Gly Leu Lys Asn Asn
1               5

<210> SEQ ID NO 164
<211> LENGTH: 5
<212> TYPE: PRT
<213> ORGANISM: homo sapiens

<400> SEQUENCE: 164

Gly Leu Thr Ser Asn
1               5

<210> SEQ ID NO 165
<211> LENGTH: 7
<212> TYPE: PRT
<213> ORGANISM: Homo sapiens

<400> SEQUENCE: 165

Val Val Thr Gly Gly Glu Val
1               5

<210> SEQ ID NO 166
<211> LENGTH: 7
<212> TYPE: PRT
<213> ORGANISM: Homo sapiens
```

```
<400> SEQUENCE: 166

Ile Ser Ser Ile Lys Asp Lys
1               5

<210> SEQ ID NO 167
<211> LENGTH: 7
<212> TYPE: PRT
<213> ORGANISM: Homo sapiens

<400> SEQUENCE: 167

Leu Leu Lys Gly Gly Glu Gln
1               5

<210> SEQ ID NO 168
<211> LENGTH: 7
<212> TYPE: PRT
<213> ORGANISM: Homo sapiens

<400> SEQUENCE: 168

Leu Gln Lys Gly Gly Glu Glu
1               5

<210> SEQ ID NO 169
<211> LENGTH: 7
<212> TYPE: PRT
<213> ORGANISM: Homo sapiens

<400> SEQUENCE: 169

Leu Tyr Lys Ala Gly Glu Leu
1               5

<210> SEQ ID NO 170
<211> LENGTH: 7
<212> TYPE: PRT
<213> ORGANISM: Homo sapiens

<400> SEQUENCE: 170

Leu Thr Ser Ser Gly Ile Glu
1               5

<210> SEQ ID NO 171
<211> LENGTH: 8
<212> TYPE: PRT
<213> ORGANISM: homo sapiens

<400> SEQUENCE: 171

Gln Glu Ala Tyr Lys Gln Gln Asn
1               5

<210> SEQ ID NO 172
<211> LENGTH: 8
<212> TYPE: PRT
<213> ORGANISM: Homo sapiens

<400> SEQUENCE: 172

Gln Glu Ala Tyr Lys Gln Gln Asn
1               5

<210> SEQ ID NO 173
<211> LENGTH: 7
<212> TYPE: PRT
<213> ORGANISM: Homo sapiens
```

<400> SEQUENCE: 173

Leu Leu Ser Asn Gly Ala Val
1               5

<210> SEQ ID NO 174
<211> LENGTH: 4
<212> TYPE: PRT
<213> ORGANISM: Homo sapiens

<400> SEQUENCE: 174

Glu Thr Met Glu
1

<210> SEQ ID NO 175
<211> LENGTH: 5
<212> TYPE: PRT
<213> ORGANISM: Homo sapiens

<400> SEQUENCE: 175

Leu Ser Ser Gly Lys
1               5

<210> SEQ ID NO 176
<211> LENGTH: 6
<212> TYPE: PRT
<213> ORGANISM: Homo sapiens

<400> SEQUENCE: 176

Phe Tyr Asn Asn Glu Ile
1               5

<210> SEQ ID NO 177
<211> LENGTH: 6
<212> TYPE: PRT
<213> ORGANISM: Homo sapiens

<400> SEQUENCE: 177

Tyr Asn Asn Lys Glu Leu
1               5

<210> SEQ ID NO 178
<211> LENGTH: 6
<212> TYPE: PRT
<213> ORGANISM: Homo sapiens

<400> SEQUENCE: 178

Tyr Ser Tyr Glu Lys Leu
1               5

<210> SEQ ID NO 179
<211> LENGTH: 6
<212> TYPE: PRT
<213> ORGANISM: Homo sapiens

<400> SEQUENCE: 179

Tyr Asn Phe Lys Glu Gln
1               5

<210> SEQ ID NO 180
<211> LENGTH: 6
<212> TYPE: PRT
<213> ORGANISM: homo sapiens

```
<400> SEQUENCE: 180

Tyr Ser Leu Glu Glu Arg
1               5

<210> SEQ ID NO 181
<211> LENGTH: 6
<212> TYPE: PRT
<213> ORGANISM: Homo sapiens

<400> SEQUENCE: 181

Tyr Phe Ser Glu Thr Gln
1               5

<210> SEQ ID NO 182
<211> LENGTH: 6
<212> TYPE: PRT
<213> ORGANISM: Homo sapiens

<400> SEQUENCE: 182

Tyr Tyr Arg Glu Glu Glu
1               5

<210> SEQ ID NO 183
<211> LENGTH: 6
<212> TYPE: PRT
<213> ORGANISM: Homo sapiens

<400> SEQUENCE: 183

Tyr Tyr Glu Lys Glu Glu
1               5

<210> SEQ ID NO 184
<211> LENGTH: 6
<212> TYPE: PRT
<213> ORGANISM: Homo sapiens

<400> SEQUENCE: 184

Tyr Tyr Glu Glu Glu Glu
1               5

<210> SEQ ID NO 185
<211> LENGTH: 6
<212> TYPE: PRT
<213> ORGANISM: Homo sapiens

<400> SEQUENCE: 185

Tyr Asp Glu Gly Glu Glu
1               5

<210> SEQ ID NO 186
<211> LENGTH: 6
<212> TYPE: PRT
<213> ORGANISM: Homo sapiens

<400> SEQUENCE: 186

Ser Ala Ser Glu Gly Thr
1               5

<210> SEQ ID NO 187
<211> LENGTH: 6
<212> TYPE: PRT
<213> ORGANISM: Homo sapiens
```

```
<400> SEQUENCE: 187

Ser Val Gly Glu Gly Thr
1               5

<210> SEQ ID NO 188
<211> LENGTH: 6
<212> TYPE: PRT
<213> ORGANISM: Homo sapiens

<400> SEQUENCE: 188

Ser Val Gly Glu Gly Thr
1               5

<210> SEQ ID NO 189
<211> LENGTH: 6
<212> TYPE: PRT
<213> ORGANISM: Homo sapiens

<400> SEQUENCE: 189

Ser Asn Thr Ala Gly Thr
1               5

<210> SEQ ID NO 190
<211> LENGTH: 6
<212> TYPE: PRT
<213> ORGANISM: Homo sapiens

<400> SEQUENCE: 190

Ser Val Gly Ala Gly Ile
1               5

<210> SEQ ID NO 191
<211> LENGTH: 6
<212> TYPE: PRT
<213> ORGANISM: Homo sapiens

<400> SEQUENCE: 191

Ser Val Gly Ala Gly Ile
1               5

<210> SEQ ID NO 192
<211> LENGTH: 6
<212> TYPE: PRT
<213> ORGANISM: Homo sapiens

<400> SEQUENCE: 192

Ser Ala Ala Ala Gly Thr
1               5

<210> SEQ ID NO 193
<211> LENGTH: 6
<212> TYPE: PRT
<213> ORGANISM: Homo sapiens

<400> SEQUENCE: 193

Ser Val Ala Ala Gly Ile
1               5

<210> SEQ ID NO 194
<211> LENGTH: 6
<212> TYPE: PRT
<213> ORGANISM: Homo sapiens
```

```
<400> SEQUENCE: 194

Phe Gln Gly Asn Ser Ala
1               5

<210> SEQ ID NO 195
<211> LENGTH: 6
<212> TYPE: PRT
<213> ORGANISM: Homo sapiens

<400> SEQUENCE: 195

Phe Gln Gly Thr Gly Ala
1               5

<210> SEQ ID NO 196
<211> LENGTH: 6
<212> TYPE: PRT
<213> ORGANISM: Homo sapiens

<400> SEQUENCE: 196

Ser Gln Ser Asp Ala Gln
1               5

<210> SEQ ID NO 197
<211> LENGTH: 6
<212> TYPE: PRT
<213> ORGANISM: Homo sapiens

<400> SEQUENCE: 197

Phe Asn Tyr Glu Ala Gln
1               5

<210> SEQ ID NO 198
<211> LENGTH: 6
<212> TYPE: PRT
<213> ORGANISM: Homo sapiens

<400> SEQUENCE: 198

Phe Asn Tyr Glu Ala Gln
1               5

<210> SEQ ID NO 199
<211> LENGTH: 6
<212> TYPE: PRT
<213> ORGANISM: homo sapiens

<400> SEQUENCE: 199

Phe Gln Asn Glu Ala Gln
1               5

<210> SEQ ID NO 200
<211> LENGTH: 6
<212> TYPE: PRT
<213> ORGANISM: Homo sapiens

<400> SEQUENCE: 200

Phe Gln Asn Glu Ala Gln
1               5

<210> SEQ ID NO 201
<211> LENGTH: 6
<212> TYPE: PRT
<213> ORGANISM: Homo sapiens
```

```
<400> SEQUENCE: 201

Tyr Tyr Asn Gly Glu Glu
1               5

<210> SEQ ID NO 202
<211> LENGTH: 6
<212> TYPE: PRT
<213> ORGANISM: Homo sapiens

<400> SEQUENCE: 202

Ser Tyr Gly Val Gln Asp
1               5

<210> SEQ ID NO 203
<211> LENGTH: 6
<212> TYPE: PRT
<213> ORGANISM: Homo sapiens

<400> SEQUENCE: 203

Ser Ala Ala Ala Asp Ile
1               5

<210> SEQ ID NO 204
<211> LENGTH: 6
<212> TYPE: PRT
<213> ORGANISM: Homo sapiens

<400> SEQUENCE: 204

Ser Tyr Gly Val Lys Asp
1               5

<210> SEQ ID NO 205
<211> LENGTH: 6
<212> TYPE: PRT
<213> ORGANISM: Homo sapiens

<400> SEQUENCE: 205

Phe Gln Asp Glu Ser Val
1               5

<210> SEQ ID NO 206
<211> LENGTH: 6
<212> TYPE: PRT
<213> ORGANISM: Homo sapiens

<400> SEQUENCE: 206

Phe Gln Asn Asn Gly Val
1               5

<210> SEQ ID NO 207
<211> LENGTH: 6
<212> TYPE: PRT
<213> ORGANISM: Homo sapiens

<400> SEQUENCE: 207

Tyr Glu Asn Glu Glu Ala
1               5

<210> SEQ ID NO 208
<211> LENGTH: 6
<212> TYPE: PRT
<213> ORGANISM: Homo sapiens
```

```
<400> SEQUENCE: 208

Phe Cys Ser Trp Thr Leu
1               5

<210> SEQ ID NO 209
<211> LENGTH: 5
<212> TYPE: PRT
<213> ORGANISM: Homo sapiens

<400> SEQUENCE: 209

Phe Arg Ser Ser Ile
1               5

<210> SEQ ID NO 210
<211> LENGTH: 6
<212> TYPE: PRT
<213> ORGANISM: Homo sapiens

<400> SEQUENCE: 210

Phe Asn Asn Asn Val Pro
1               5

<210> SEQ ID NO 211
<211> LENGTH: 6
<212> TYPE: PRT
<213> ORGANISM: Homo sapiens

<400> SEQUENCE: 211

Phe Asn Asn Asn Val Pro
1               5

<210> SEQ ID NO 212
<211> LENGTH: 6
<212> TYPE: PRT
<213> ORGANISM: Homo sapiens

<400> SEQUENCE: 212

Phe Arg Asn Arg Ala Pro
1               5

<210> SEQ ID NO 213
<211> LENGTH: 6
<212> TYPE: PRT
<213> ORGANISM: homo sapiens

<400> SEQUENCE: 213

Phe Tyr Glu Lys Met Gln
1               5

<210> SEQ ID NO 214
<211> LENGTH: 6
<212> TYPE: PRT
<213> ORGANISM: Homo sapiens

<400> SEQUENCE: 214

Phe Val Lys Glu Ser Lys
1               5

<210> SEQ ID NO 215
<211> LENGTH: 6
<212> TYPE: PRT
<213> ORGANISM: Homo sapiens
```

```
<400> SEQUENCE: 215

Phe Val Lys Glu Ser Lys
1               5

<210> SEQ ID NO 216
<211> LENGTH: 6
<212> TYPE: PRT
<213> ORGANISM: Homo sapiens

<400> SEQUENCE: 216

Phe Gln Asn Glu Asn Val
1               5

<210> SEQ ID NO 217
<211> LENGTH: 6
<212> TYPE: PRT
<213> ORGANISM: Homo sapiens

<400> SEQUENCE: 217

Leu Gln Lys Glu Asn Ile
1               5

<210> SEQ ID NO 218
<211> LENGTH: 6
<212> TYPE: PRT
<213> ORGANISM: Homo sapiens

<400> SEQUENCE: 218

Ser Gln Ile Val Asn Asp
1               5

<210> SEQ ID NO 219
<211> LENGTH: 7
<212> TYPE: PRT
<213> ORGANISM: Homo sapiens

<400> SEQUENCE: 219

Ser Asn Glu Gly Ser Lys Ala
1               5

<210> SEQ ID NO 220
<211> LENGTH: 6
<212> TYPE: PRT
<213> ORGANISM: Homo sapiens

<400> SEQUENCE: 220

Ser Phe Asp Val Lys Asp
1               5

<210> SEQ ID NO 221
<211> LENGTH: 6
<212> TYPE: PRT
<213> ORGANISM: Homo sapiens

<400> SEQUENCE: 221

Ser Tyr Gly Val Asn Ser
1               5

<210> SEQ ID NO 222
<211> LENGTH: 6
<212> TYPE: PRT
<213> ORGANISM: Homo sapiens
```

```
<400> SEQUENCE: 222

Ser Met Asn Val Glu Val
1               5

<210> SEQ ID NO 223
<211> LENGTH: 6
<212> TYPE: PRT
<213> ORGANISM: Homo sapiens

<400> SEQUENCE: 223

Ser Tyr Asp Val Lys Met
1               5

<210> SEQ ID NO 224
<211> LENGTH: 5
<212> TYPE: PRT
<213> ORGANISM: Homo sapiens

<400> SEQUENCE: 224

Ser Val Gly Ile Gly
1               5

<210> SEQ ID NO 225
<211> LENGTH: 5
<212> TYPE: PRT
<213> ORGANISM: Artificial
<220> FEATURE:
<223> OTHER INFORMATION: Linker

<400> SEQUENCE: 225

Gly Gly Gly Gly Ser
1               5

<210> SEQ ID NO 226
<211> LENGTH: 18
<212> TYPE: PRT
<213> ORGANISM: artificial
<220> FEATURE:
<223> OTHER INFORMATION: linker

<400> SEQUENCE: 226

Lys Glu Ser Gly Ser Val Ser Ser Glu Gln Leu Ala Gln Phe Arg Ser
1               5                   10                  15

Leu Asp

<210> SEQ ID NO 227
<211> LENGTH: 14
<212> TYPE: PRT
<213> ORGANISM: artificial
<220> FEATURE:
<223> OTHER INFORMATION: linker

<400> SEQUENCE: 227

Glu Gly Lys Ser Ser Gly Ser Gly Ser Glu Ser Lys Ser Thr
1               5                   10

<210> SEQ ID NO 228
<211> LENGTH: 12
<212> TYPE: PRT
<213> ORGANISM: artificial
<220> FEATURE:
<223> OTHER INFORMATION: linker
```

```
<400> SEQUENCE: 228

Gly Ser Ala Gly Ser Ala Ala Gly Ser Gly Glu Phe
1               5                   10

<210> SEQ ID NO 229
<211> LENGTH: 9
<212> TYPE: PRT
<213> ORGANISM: artificial
<220> FEATURE:
<223> OTHER INFORMATION: SLL peptide

<400> SEQUENCE: 229

Ser Leu Leu Gln His Leu Ile Gly Leu
1               5

<210> SEQ ID NO 230
<211> LENGTH: 10
<212> TYPE: PRT
<213> ORGANISM: artificial
<220> FEATURE:
<223> OTHER INFORMATION: ALY peptide

<400> SEQUENCE: 230

Ala Leu Tyr Val Asp Ser Leu Phe Phe Leu
1               5                   10

<210> SEQ ID NO 231
<211> LENGTH: 10
<212> TYPE: PRT
<213> ORGANISM: artificial
<220> FEATURE:
<223> OTHER INFORMATION: ELA peptide

<400> SEQUENCE: 231

Glu Leu Ala Gly Ile Gly Ile Leu Thr Val
1               5                   10
```